US009556455B2

(12) United States Patent
Healey et al.

(10) Patent No.: US 9,556,455 B2
(45) Date of Patent: *Jan. 31, 2017

(54) MATURE DENDRITIC CELL COMPOSITIONS AND METHODS FOR CULTURING SAME

(71) Applicant: Argos Therapeutics, Inc., Durham, NC (US)

(72) Inventors: Don Healey, Rougemont, NC (US); Irina Tcherepanova, Rougemont, NC (US); Melissa Adams, Chapel Hill, NC (US)

(73) Assignee: Argos Therapeutics, Inc., Durham, NC (US)

( * ) Notice: Subject to any disclaimer, the term of this patent is extended or adjusted under 35 U.S.C. 154(b) by 34 days.

This patent is subject to a terminal disclaimer.

(21) Appl. No.: 14/473,868

(22) Filed: Aug. 29, 2014

(65) Prior Publication Data

US 2015/0072431 A1  Mar. 12, 2015

Related U.S. Application Data

(63) Continuation of application No. 11/246,387, filed on Oct. 7, 2005, now Pat. No. 8,822,223.

(60) Provisional application No. 60/522,512, filed on Oct. 7, 2004.

(51) Int. Cl.
| | |
|---|---|
| *C12N 15/87* | (2006.01) |
| *C12N 5/00* | (2006.01) |
| *C12N 5/071* | (2010.01) |
| *A61K 39/00* | (2006.01) |
| *C12N 5/02* | (2006.01) |
| *A01N 3/00* | (2006.01) |
| *C12N 5/0784* | (2010.01) |

(52) U.S. Cl.
CPC ............. *C12N 15/87* (2013.01); *C12N 5/0639* (2013.01); *A61K 2039/5154* (2013.01); *C12N 2500/36* (2013.01); *C12N 2501/02* (2013.01); *C12N 2501/22* (2013.01); *C12N 2501/23* (2013.01); *C12N 2501/24* (2013.01); *C12N 2501/52* (2013.01); *C12N 2510/00* (2013.01)

(58) Field of Classification Search
CPC ........ C12N 5/0639; C12N 5/064; C12N 15/87
USPC ......................................................... 435/325
See application file for complete search history.

(56) References Cited

U.S. PATENT DOCUMENTS

| | | | |
|---|---|---|---|
| 5,962,406 A | 10/1999 | Armitage et al. | |
| 6,107,527 A | 8/2000 | Stec et al. | |
| 6,410,711 B1 | 6/2002 | Armitage et al. | |
| 6,482,411 B1 * | 11/2002 | Ahuja ............. | C07K 14/70575 424/178.1 |
| 6,531,453 B1 | 3/2003 | Taniguchi et al. | |
| 6,555,372 B1 | 4/2003 | Motoki | |
| 6,747,010 B2 | 6/2004 | Taniguchi et al. | |
| 7,029,671 B1 | 4/2006 | Koezuka et al. | |
| 7,252,996 B2 | 8/2007 | Boccaccio et al. | |
| 7,405,076 B2 | 7/2008 | Goldman et al. | |
| 7,488,491 B2 | 2/2009 | Tsuji et al. | |
| 8,513,008 B2 | 8/2013 | Tcherepanova et al. | |
| 8,822,223 B2 | 9/2014 | Healey et al. | |
| 2002/0115624 A1 | 8/2002 | Behar et al. | |
| 2002/0164331 A1 | 11/2002 | Exley et al. | |
| 2003/0077263 A1 | 4/2003 | Maraskovsky et al. | |
| 2003/0095957 A1 | 5/2003 | Crystal et al. | |
| 2003/0153073 A1 | 8/2003 | Rogers et al. | |
| 2004/0146948 A1 | 7/2004 | Britton et al. | |
| 2004/0241147 A1 | 12/2004 | Nardin et al. | |

(Continued)

FOREIGN PATENT DOCUMENTS

| | | |
|---|---|---|
| EP | 0 922 758 B1 | 4/2009 |
| WO | WO 93/08207 A1 | 4/1993 |

(Continued)

OTHER PUBLICATIONS

Onaitis et al 2003, Surgery 134:300-305.*
Luft et al 2002, Int Immunol. 14:367-380.*
Zhang et al 2003, Proc. Natl. Acad. Sci. 100:15101-15106.*
Attwood, T. K., "The Babel of Bioinformatics," *Science* 290(5491):471-473, American Association for the Advancement of Science, United States (2000).
Blaeser, F., et al., "Critical function of the CD40 pathway in parvovirus B19 infection revealed by a hypomorphic CD40 ligand mutation," Clinical Immunology 117(3):231-237, Academic Press, United States (2005).

(Continued)

*Primary Examiner* — Christopher M Babic
*Assistant Examiner* — Kelaginamane T Hiriyanna
(74) *Attorney, Agent, or Firm* — Sterne, Kessler, Goldstein & Fox P.L.L.C.

(57) ABSTRACT

This invention provides methods to prepare and use immunostimulatory cells for enhancing an immune response. The invention provides a method for preparing mature dendritic cells (DCs), comprising the sequential steps of: (a) signaling isolated immature dendritic cells (iDCs) with a first signal comprising an interferon gamma receptor (IFN-γR) agonist and/or a tumor necrosis factor alpha receptor (TNF-αR) agonist to produce signaled dendritic cells; and (b) signaling said signaled dendritic cells with a second transient signal comprising an effective amount of a CD40 agonist to produce CCR7+ mature dendritic cells. Also provided by this invention are enriched populations of dendritic cells prepared by the methods of the invention. Such dendritic cells have enhanced immunostimulatory properties and increased IL-12 secretion and/or decreased IL-10 secretion. CD40 signaling can be initiated by one or more of polypeptide translated from an exogenous polynucleotide encoding CD40L (e.g., mRNA or DNA), an agonistic antibody to CD40 receptor or by CD40 ligand polypeptide. The enriched populations can be further modified by the administration of an immunogen to the DC. The DC will take up and process the immunogen on its cell surface.

19 Claims, 23 Drawing Sheets

(56) References Cited

U.S. PATENT DOCUMENTS

| | | | |
|---|---|---|---|
| 2005/0003533 A1* | 1/2005 | Kalinski | C12N 5/0639 |
| | | | 435/372 |
| 2005/0159365 A1 | 7/2005 | Serizawa et al. | |
| 2005/0222048 A1 | 10/2005 | Tsuji et al. | |
| 2006/0121003 A1* | 6/2006 | Gilboa | A61K 39/0011 |
| | | | 424/93.7 |
| 2008/0145931 A1 | 6/2008 | Healey et al. | |
| 2012/0269832 A1 | 10/2012 | Healey et al. | |
| 2014/0017788 A1 | 1/2014 | Healey et al. | |

FOREIGN PATENT DOCUMENTS

| | | |
|---|---|---|
| WO | WO 98/01538 A1 | 1/1998 |
| WO | WO 99/61051 A1 | 12/1999 |
| WO | WO 02/36141 A2 | 5/2002 |
| WO | WO 02/074345 A2 | 9/2002 |
| WO | WO 02/088186 A1 | 11/2002 |
| WO | WO 03/000907 A2 | 1/2003 |
| WO | WO 2004/009615 A2 | 1/2004 |
| WO | WO 2004/031276 A2 | 4/2004 |
| WO | WO 2004/089413 A1 | 10/2004 |
| WO | WO 2006/042177 A2 | 4/2006 |
| WO | WO 2007/117682 A2 | 10/2007 |

OTHER PUBLICATIONS

Bonehill, A., et al., "Messenger RNA-electroporated dendritic cells presenting MAGE-A3 simultaneously in HLA class I and class II molecules," Journal of Immunology 172(11):6649-6657, The American Association of Immunologists, Inc., United States (2004).

Calderhead, D.M., et al., "Cytokine maturation followed by CD40L mRNA electroporation results in a clinically relevant dendritic cell product capable of inducing a potent proinflammatory CTL response," Journal of Immunotherapy 31(8):731-741, Lippincott Williams & Wilkins, United States (2008).

Chang, D.H., et al., "Sustained expansion of NKT cells and antigen-specific T cells after injection of alpha-galactosyl-ceramide loaded mature dendritic cells in cancer patients," The Journal of Experimental Medicine 201(9):1503-1517, Rockefeller University Press, United States (2005).

Chung, Y., et al., "NKT cell ligand [alpha]-galactosylceramide blocks the induction of oral tolerance by triggering dendritic cell maturation," European Journal of Immunology 34(9):2471-2479, Wiley-VCH Verlag GmbH & Co. KGaA, Germany (2004).

Corish, P. and Tyler-Smith, C., "Attenuation of green fluorescent protein half-life in mammalian cells," Protein Engineering 12(12):1035-1040, Oxford University Press, England (1999).

Dauer, M., et al., "Mature dendritic cells derived from human monocytes within 48 hours: a novel strategy for dendritic cell differentiation from blood precursors," The Journal of Immunology 170(8):4069-4076, The American Association of Immunologists, Inc., United States (2003).

Debenedette, M.A., et aL, "Priming of a novel subset of CD28+ rapidly expanding high-avidity effector memory CTL by post maturation electroporation-CD40L dendritic cells is IL-12 dependent," The Journal of Immunology 181(8):5296-5305, The American Association of Immunologists, Inc., United States (2008).

EMBL: P27548; Aug. 14, 2001.

EMBL:P29965; Aug. 1, 1993.

Examiner's search strategy and results, USPTO Sequence Search, U.S. Appl. No. 11/400,774, Nov. 17, 2008.

Faries, M.B., et al., "Calcium signaling inhibits interleukin-12 production and activates CD83(+) dendritic cells that induce Th2 cell development," Blood 98(8):2489-2497, American Society of Hematology, United States (2000).

Gallie, D.R., et al., "The tobacco etch viral 5' leader and poly(A) tail are functionally synergistic regulators of translation," Gene 165(2):233-238, Elsevier Science B.V., Netherlands (1995).

Gallie, D.R., "Cap-independent translation conferred by the 5' leader of tobacco etch virus is eukaryotic initiation factor 4G dependent," Journal of Virology 75(24):12141-12152, American Society for Microbiology, United States (2001).

Gamberg, J., et al., "Lack of CD28 expression on HIV-specific cytotoxic T lymphocytes is associated with disease progression," Immunology and Cell Biology 82(1):38-46, University of Adelaide, Australia (2004).

Gerosa, F., et al., "Reciprocal activating interaction between natural killer cells and dendritic cells," The Journal of Experimental Medicine 195(3):327-333, Rockefeller University Press, United States (2002).

Holtkamp, S., et al., "Modification of antigen-encoding RNA increases stability, translational efficacy, and T-cell stimulatory capacity of dendritic cells," Blood 108(13):4009-4017, American Society of Hematology, United States (2006).

Hsu, Y.M., et al., "Heteromultimeric complexes of CD40 ligand are present on the cell surface of human T lymphocytes," The Journal of Biological Chemistry 272(2):911-915, The American Society for Biochemistry and Molecular Biology, Inc., United States (1997).

Hwu, P., et al., "Indoleamine 2,3-dioxygenase production by human dendritic cells results in the inhibition of T cell proliferation," The American Association of Immunologists, United States (2000).

International Search Report for International Application No. PCT/US2005/036304, European Patent Office, Netherlands, mailed Nov. 13, 2006.

Ishikawa, A., et al., "A phase I study of alpha-galactosylceramide (KRN7000)-pulsed dendritic cells in patients with advanced and recurrent non-small cell lung cancer," Clinical Cancer Research 11(5):1910-1917, American Association for Cancer Research, United States (2005).

Ishikawa, E., et al., "Dendritic cell maturation by CD11c-T cells and Valpha24+ natural killer T-cell activation by alpha-galactosylceramide," International Journal of Cancer 117(2):265-273, Wiley-Liss, United States (2005).

Janeway, C.A., et al., Immunolobiology: the immune system in health and disease, 6th Edition, p. 175, figure 5.6, Garland Science Publishing, United States (2005).

Javorovic, M., et al., "RNA transfer by electroporation into mature dendritic cells leading to reactivation of effector-memory cytotoxic T lymphocytes: a quantitative analysis," Molecular Therapy 12(4):734-743, The American Society of Gene Therapy, United States (2005).

Jonuleit, H., et al., "Pro-inflammatory cytokines and prostaglandins induce maturation of potent immunostimulatory dendritic cells under fetal calf serum-free conditions," European Journal of Immunology 27(12):3135-3142, Wiley-VCH Verlag GmbH, Germany (1997).

Kalady, M.F., et al, "Sequential maturation stimuli enhance antigen-specific immunogenicity of RNA-transfected dendritic cells" Immunology/Experimental and Preclinical 43:677, Abstract #3356, Proceedings of the American Association for Cancer Research, United States (2002).

Kalady, M.F., et al., "Sequential delivery of maturation stimuli increases human dendritic cell IL-12 production and enhances tumor antigen-specific immunogenicity," The Journal of Surgical Research 116(1):24-31, Academic Press, United States (2004).

Kikuchi, T.,et al., "Dendritic cells modified to express CD40 ligand elicit therapeutic immunity against preexisting murine tumors," Blood 96(1):91-99, American Society of Hematology, United States (2000).

Kikuchi, T., et al., "Dendritic cells genetically modified to express CD40 ligand and pulsed with antigen can initiate antigen-specific humoral immunity independent of CD4+ T cells," Nature Medicine 6(10):1154-1159, Nature Publishing Company, United States (2000).

Kimura, T., et al., Treatment with α-Galactosylceramide Attenuates the Development of Bleomycin-Induced Pulmonary Fibrosis, *The Journal of Immunology* 172:5782-5789, The American Association of Immunologists, Inc., United States (2004).

Koya, R.C., et al., "Potent Maturation of Monocyte-Derived Dendritic Cells After CD40L Lentiviral Gene Delivery," *Journal of Immunotherapy* 26(5):451-460, Lippincott Williams & Wilkins, Inc., United States (2003).

Kuniyoshi, J.S., et al., "Dendritic Cell Secretion of IL-15 is Induced by Recombinant huCD40LT and Augments the Stimulation of

(56) References Cited

OTHER PUBLICATIONS

Antigen-Specific Cytolytic T cells," *Cellular Immunology* 193(1):48-58, Academic Press, United States (1999).

Ledbetter, J.A., et al., "Agonistic Activity of a CD40-Specific Single-Chain Fv Constructed from the Variable Regions of mAb G28-5," *Critical Reviews in Immunology* 17(5-6):427-435, Begell House, United States (1997).

Lee, J.-J., et al., "The Role of $PGE_2$ in the Differentiation of Dendritic Cells: How Do Dendritic Cells Influence T-Cell Polarization and Chemokine Receptor Expression?" *Stem Cells* 20(5):448-459, AlphaMed Press, United States (2002).

Lemoine, R., et al., "Interferon gamma licensing of human dendritic cells in T-helper-independent $CD8^+$ alloimmunity" *Blood* 116(16):3089-3098, The American Society of Hematology, United States (2010).

Liao, X., et al., "Transfection of RNA Encoding Tumor Antigens Following Maturation of Dendritic Cells Leads to Prolonged Presentation of Antigen and the Generation of High-Affinity Tumor-Reactive Cytotoxic T Lymphocytes," *Molecular Therapy* 9(5):757-763, Academic Press, United States (2004).

Lieberman, J., et al., "Dressed to Kill? A review of why antiviral CD8 T lymphocytes fail to prevent progressive immunodeficiency in HIV-infection," *Blood* 98(6):1667-1677, The American Society of Hematology, United States (2001).

Liu, et al., "Experimental study on the function of natural killer T cell activated by α-galactosylceramide," *J Appln. Clin. Pediatr.* 19(1):52-54 (2004).

Luft, T., et al., "IFN-alpha enhances CD40 ligand-mediated activation of immature monocyte-derived dendritic cells," *International Immunology* 14(4):367-380, Oxford University Press, England (2002).

Luft, T., et al., "Tuning the volume of the immune response: strength and persistence of stimulation determine migration and cytokine secretion of dendritic cells," *Blood* 104(4):1066-1074, American Society of Hematology, United States (2004).

Lutz, M.B. and Schuler, G., "Immature, semi-mature and fully mature dendritic cells: which signals induce tolerance or immunity?" *TRENDS in Immunology* 23(9):445-449, Elsevier, England (2002).

Mazzei, G.J., et al., "Recombinant Soluble Trimeric CD40 Ligand is Biologically Active" *Journal of Biological Chemistry* 270(13):7025-7028, The American Society for Biochemistry and Molecular Biology, Inc., United States (1995).

Michiels, A., et al., "Electroporation of immature and mature dendritic cells: implications for dendritic cell-based vaccines" *Gene Therapy* 12(9):772-782, Nature Publishing Group, England (2005).

Mosca, P.J., et al., A subset of human monocyte-derived dendritic cells expresses high levels of interleukin-12 in response to combined CD40 ligand and interferon-γ treatment, *Blood* 96(10):3499-3504, The American Society of Hematology, United States (2000).

Niepel, M., et al., "Identification and Characterization of the Functional Elements within the Tobacco Etch Virus 5' Leader Required for Cap-Independent Translation," *Journal of Virology* 73(11):9080-9088, American Society for Microbiology, United States (1999).

Office Action mailed Jun. 24, 2008, in U.S. Appl. No. 11/400,774, inventors Tcherepanova, T., filed Apr. 7, 2006.

Office Action mailed Nov. 17, 2008, in U.S. Appl. No. 11/400,774, inventors Tcherepanova, T., filed Apr. 7, 2006.

Office Action mailed Jul. 10, 2009, in U.S. Appl. No. 11/400,774, inventors Tcherepanova, T., filed Apr. 7, 2006.

Office Action mailed Mar. 31, 2010, in U.S. Appl. No. 11/400,774, inventors , Tcherepanova, I., et al., filed Apr. 7, 2006.

Office Action mailed Apr. 12, 2011, in U.S. Appl. No. 11/400,774, inventors Tcherepanova, T., filed Apr. 7, 2006.

Office Action mailed Oct. 26, 2011, in U.S. Appl. No. 11/400,774, inventors Tcherepanova, T., filed Apr. 7, 2006.

Office Action mailed Mar. 31, 2010, in U.S. Appl. No. 11/664,899, inventors Healey, D., et al., international filing date: Oct. 7, 2005.

Office Action mailed Oct. 28, 2010, in U.S. Appl. No. 11/664,899, inventors Healey, D., et al., international filing date: Sep. 28, 2007.

Office Action mailed Jul. 19, 2011, in U.S. Appl. No. 11/664,899, inventors Healey, D., et al., international filing date: Oct. 7, 2005.

Office Action mailed Jan. 5, 2012, in U.S. Appl. No. 11/664,899, inventors Healey, D., et al., international filing date: Oct. 7, 2005.

Office Action mailed Jun. 6, 2012, in U.S. Appl. No. 11/664,899, inventors Healey, D., et al., international filing date: Sep. 28, 2007.

Office Action mailed Sep. 25, 2012, in U.S. Appl. No. 12/226,092, inventors Healey, D., et al., § 371(c) date: Nov. 12, 2009.

Office Action mailed May 6, 2013, in U.S. Appl. No. 12/226,092, inventors Healey, D., et al., § 371(c) date: Nov. 12, 2009.

Onaitis, M.W., et al., "CD40 ligand is essential for generation of specific cytotoxic T cell responses in RNA-pulsed dendritic cell immunotherapy," *Surgery* 134(2):300-305, Mosby, United States (2003).

Osada, T., et al., "Dendritic Cells Cultured in Anti-CD40 Antibody-Immobilized Plates Elicit a Highly Efficient Peptide-Specific T-Cell Response," *Journal of Immunotherapy* 25(2):176-184, Lippincott Williams & Wilkins, Inc., United States (2002).

Parekh, V.V., et al., "Quantitative and Qualitative Differences in the In Vivo Response of NKT Cells to Distinct α- and β-Anomeric Glycolipids," *The Journal of Immunology* 173(6):3693-3706, American Association of Immunologists, United States (2004).

Penna, G., et al., "Cutting Edge: Selective Usage of Chemokine Receptors by Plasmacytoid Dendritic Cells," *The Journal of Immunology* 167(4):1862-1866, American Association of Immunologists, United States (2001).

Pereboev, A.V., et al., "Enhanced Gene Transfer to Mouse Dendritic Cells Using Adenoviral Vectors Coated with a Novel Adapter Molecule," *Molecular Therapy* 9(5):712-720, Academic Press, United States (2004).

Pietravalle, F., et al., "Human Native Soluble CD40L is a Biologically Active Trimer, Processed Inside Microsomes," *The Journal of Biological Chemistry* 271(11):5965-5967, The American Society for Biochemistry and Molecular Biology, Inc., United States (1996).

Ponsaerts, P., et al., "Cancer immunotherapy using RNA-loaded dendritic cells," *Clinical and Experimental Immunology* 134(3):378-384, Blackwell Publishing Ltd., England (2003).

Popesou, I., et al., "Ex Vivo Priming of Naïve T Cells Into EBV-Specific Th1/Tc1 Effector Cells by Mature Autologous DC Loaded with Apoptotic/Necrotic LCL," *American Journal of Transplantation* 3:1369-1377, Blackwell Munksgaard, Denmark (2003).

Qin, H. and Gunning, P., "The 3'-end of the human β-actin gene enhances activity of the β-actin expression vector system: construction of improved vectors," *Journal of Biochemical and Biophysical Methods* 36(1):63-72, Elsevier, Netherlands (1997).

Response to Office Action in European Patent Application No. EP05804341.5, European Patent Office, Germany, mailed Dec. 21, 2007.

Response to Office Action in European Patent Application No. EP05804341.5, European Patent Office, Germany, mailed Feb. 11, 2009.

Response to Office Action in European Patent Application No. EP05804341.5, European Patent Office, Germany, mailed Mar. 11, 2010.

Response to Office Action in European Patent Application No. EP07755113.3, European Patent Office, Germany, mailed Feb. 12, 2010.

Response to Office Action in European Patent Application No. EP07755113.3, European Patent Office, Germany, mailed Jun. 22, 2010.

Roberts, T.M., et al., "The 5' RNA Terminus of Spleen Necrosis Virus Stimulates Translation of Nonviral mRNA," *Journal of Virology* 74(17):8111-8118, American Society for Microbiology, United States (2000).

Rouard, H., et al., "IL-12 secreting dendritic cells are required for optimum activation of human secondary lymphoid tissue T cells," *Journal of Immunotherapy* 25(4):324-333, Raven Press/Lippincott Williams & Wilkins, United States (2002).

Rubio, M.T., et al., "Maturation of human monocyte-derived dendritic cells (MoDCs) in the presence of prostaglandin $E_2$ optimizes CD4 and CDS T cell-mediated responses to protein antigens:

(56) References Cited

OTHER PUBLICATIONS role of PGE$_2$ in chemokine and cytokine expression by MoDCs," *International Immunology* 17(12):1561-1572, Oxford University Press, England (2005).

Sallusto, F., et al., "Rapid and coordinated switch in chemokine receptor expression during dendritic cell maturation," *European Journal of Immunology* 28(9):2760-2769, Wiley-VCH Verlag GmbH, Germany (1998).

Scandella, E., et al., "Prostaglandin E2 is a key factor for CCR7 surface expression and migration of monocyte-derived dendritic cells," *Blood* 100(4):1354-1361, The American Society of Hematology, United States (2002).

Schaft, N., et al., "Generation of an Optimized Polyvalent Monocyte-Derived Dendritic Cell Vaccine by Transfecting Defined RNAs after Rather Than before Maturation" *The Journal of Immunology* 174(5):3087-3097, The American Association of Immunologists, Inc., United States (2005).

Seyama, K., et al., "CD40 Ligand Mutants Responsible for X-linked Hyper-IgM Syndrome Associate with Wild Type CD40 Ligand," *The Journal of Biological Chemistry* 274(16):11310-11320, The American Society for Biochemistry and Molecular Biology, Inc., United States (1999).

Singh, N., et al., "Cutting Edge: Activation of NK T Cells by CD1d and α-Galactosylceramide Directs Conventional T Cells to the Acquisition of a Th2 Phenotype," *The Journal of Immunology* 163:2373-2377, The American Association of Immunologists, United States (1999).

Skolnick, J., et al., "From genes to protein structure and function: novel applications of computational approaches in the genomic era," *Trends in Biotechnology* 18:34-39 Elsevier Science Ltd., England (2000).

Stein, I., et al., "Translation of Vascular Endothelial Growth Factor mRNA by Internal Ribosome Entry: Implications for Translation under Hypoxia," *Molecular and Cellular Biology* 18(6):3112-3119, American Society for Microbiology, United States (1998).

Tcherepanova, I.Y., et al., "Ectopic expression of a truncated CD40L protein from synthetic post-transcriptionally capped RNA in dendritic cells induces high levels of IL-12 secretion," *BMC Molecular Biology* 9(1):90, BioMed Central, England (2008).

Tomiyama, H., et al., "Differentiation of Human CD8$^+$ T Cells from a Memory to Memory/Effector Phenotype[1]," *The Journal of Immunology* 168(11):5538-5550, The American Association of Immunologists, United States (2002).

Topp, M.S., et al., "Restoration of CD28 Expression in CD28$^-$ CD8$^+$ Memory Effector T Cells Reconstitutes Antigen-induced IL-2 Production," *The Journal of Experimental Medicine* 198(6):947-955, The Rockefeller University Press, United States (2003).

Torosantucci, A., et al., "*Candida albicans* Yeast and Germ Tube Forms Interfere Differently with Human Monocyte Differentiation into Dendritic Cells: a Novel Dimorphism-Dependent Mechanism to Escape the Host's Immune Response," *Infection and Immunity* 72(2):833-843, American Society for Microbiology, United States (2004).

Van Der Vliet, H.J.J., et al., "Potent expansion of human natural killer T cells using α-galactosylceramide (KRN7000)-loaded monocyte-derived dendritic cells, cultured in the presence of IL-7 and IL-15," *Journal of Immunological Methods* 247(1-2):61-72, Elsevier, Netherlands (2001).

Van Tendeloo, F.I., et al., "Highly efficient gene delivery by mRNA electroporation in human hematopoietic cells: superiority to lipofection and passive pulsing of mRNA and to electroporation of plasmid cDNA for tumor antigen loading of dendritic cells," *Blood* 98(1):49-56, The American Society of Hematology, United States (2001).

Vieira, P.L., et al., "Development of Th1-Inducing Capacity in Myeloid Dendritic Cells Requires Environmental Instruction," *The Journal of Immunology* 164(9):4507-4512, The American Association of Immunologists, Inc., United States (2000).

Vivinus, S., et al, "An element within the 5' untranslated region of human *Hsp70* mRNA which acts as a general enhancer of mRNA translation," *European Journal of Biochemistry* 268(7):1908-1907, FEBS, England(2001).

Wang, B., et al., "Multiple Paths for Activation of Naïve CD8$^+$ T cells: CD4-Independent Help[1]," *The Journal of Immunology* 167(3):1283-1289, The American Association of Immunologists, Inc., United States (2001).

Wang, X-Y., et al., "Inducing the Immune function of dendritic cells from patients with chronic hepatitis B by cytokines," *World Chin J Digestol* 11(12):1870-1873 (2003).

Weekes, M.P., et al., "Human CD28$^-$ CD8$^+$ T Cells Contain Greatly Expanded Functional Virus-Specific Memory CTL Clones[1]," *The Journal of Immunology* 162:7569-7577, The American Association of Immunologists, Inc., United States (1999).

Weissman, D., et al., "HIV Gag mRNA Transfection of Dendritic Cells (DC) Delivers Encoded Antigen to MHC Class 1 and II Molecules, Causes DC Maturation, and Induces a Potent Human In Vitro Primary Immune Response[1]," *The Journal of Immunology* 165(8):4710-4717, The American Association of Immunologists, Inc., United States (2000).

Written Opinion for International Application No. PCT/US07/08734, United States Patent Office, Alexandria, United States, mailed on Jul. 25, 2008.

Xu, S., et al., "Rapid High Efficiency Sensitization of CD8$^+$ T Cells to Tumor Antigens by Dendritic Cells Leads to Enhanced Functional Avidity and Direct Tumor Recognition Through an IL-12-Dependent Mechanism," *The Journal of Immunology* 171:2251-2261, The American Association of Immunologists, Inc., United States (2003).

Yang, A-D., et al., "Translation enhancer in the 3'-untranslated region of rotavirus gene 6 mRNA promotes expression of the major capsid protein VP6," *Archives of Virology* 149(2): 303-321, Springer-Verlag, Austria (2004).

Yoshida, S., et al., "Generation of dendritic cells from the ventricular fluid in patients with meningeal carcinomatosis" *Journal of Neuroimmunology* 140(1-2):172-176, Elsevier, Netherlands (2003).

Yu, Q., et al., "The Role of the p38 Mitogen-Activated Protein Kinase, Extracellular Signal-Regulated Kinase, and Phosphoinositide-3-0H Kinase Signal Transduction Pathways in CD40 Ligand-Induced Dendritic Cell Activation and Expansion of Virus-Specific CD8$^+$ T Cell Memory Responses[1]," *The Journal of Immunology* 172:6047-6056, The American Association of Immunologists, Inc., United States (2004).

Yu, K.O.A., et al., "Modulation of CD1d-restricted NKT cell responses by using N-acyl variants of alpha-galactosylceramides," *Proceedings of the National Academy of Sciences U.S.A.* 102(9):3383-3388, National Academy of Sciences, United States (2005).

Zaliauskiene, L., et al., "Down-Regulation of Cell Surface Receptors is Modulated by Polar Residues within the Transmembrane Domain," *Molecular Biology of the Cell* 11(8):2643-2655, American Society for Cell Biology, United States (2000).

Zhang, et al., "In Vitro Generation of Human Blood Dendritic Cells and Anti-Tumor Immunotherapy Induced Thereby" *J. Fourth Mil Med Univ.* 22(19):1777-1780 (2001).

Zhang, L., et al., "An adenoviral vector cancer vaccine that delivers a tumor-associated antigen/CD40-ligand fusion protein to dendritic cells," *Proceedings of the National Academy of Sciences U.S.A.* 100(25):15101-15106, National Academy of Sciences, United States (2003).

Zimmerli, S.C., et al., "HIV-1-specific IFN-γ/IL-2-secreting CD8 T cells support CD4-independent proliferation of HIV-1-specific CD8 T Cells," *Proceedings of the National Academy of Sciences U.S.A.* 102(20):7239-7244, National Academy of Sciences, United States (2005).

Office Action mailed Nov. 1, 2013, in U.S. Appl. No. 13/941,627, Healey, D., et al., filed Jul. 15, 2013.

Office Action mailed May 9, 2014, in U.S. Appl. No. 13/941,627, Healey, D., et al., filed Jul. 15, 2013.

(56) References Cited

OTHER PUBLICATIONS

Office Action mailed May 27, 2014, in U.S. Appl. No. 12/226,092, inventors Healey, D., et al., § 371(c) date: Nov. 12, 2009.

* cited by examiner

```
# Program:  needle
# Rundate:  Tue Oct 05 21:36:57 2004
# Align_format: srspair
# Report_file: /ebi/extserv/old-work/needle-20041005-21365334534448.output
########################################
#=======================================

# Aligned_sequences: 2
# 1: EMBOSS_001
# 2: EMBOSS_001
# Matrix: EDNAFULL
# Gap_penalty: 10.0
# Extend_penalty: 0.5

# Length: 1836
# Identity:    1033/1836 (56.3%)
# Similarity:  1033/1836 (56.3%)
# Gaps:         606/1836 (33.0%)
# Score: 4085.5

#=======================================
```

| | | | |
|---|---|---|---|
| HUMAN CD40L | 1 | cttctctgccagaagataccatttcaactttaacacagcatgatcgaaac | 50 |
| | | \|\|\|\|.\|..\|\|\|\|\|\|\|\|\|\|.:\|\|\|\| | |
| MOUSE CD40L | 1 | ctttcagtcagcatgatagaaac | 23 |
| EMBOSS_001 | 51 | atacaaccaaacttctccccgatctgcggccactggactgccatc-agc | 99 |
| | | \|\|\|\|.\|\|\|\|:.\|\|\|\|.\|\|\|.:\|\|\|:.\|.\|\|\|.\|\|\|\|\|\|\|\| .\|\|\|.\| \|\|\| | |
| EMBOSS_001 | 24 | atacagccaaccttccccagatccgtggcaactggact-tccagcgagc | 72 |
| EMBOSS_001 | 100 | atgaaaatttttatgtatttacttactgttttcttatcacccagatgat | 149 |
| | | \|\|\|\|.\|\|\|\|\|\|\|\|\|\|\|\|\|\|\|\|\|\|\|\|\|\|:\|\|\|\|\|\|.\|\|\|\|\|\|\|\|\|\|\|.\|\|\|\|\| | |
| EMBOSS_001 | 73 | atgaagatttttatgtatttacttactgttttccttatcacccaaatgat | 122 |
| EMBOSS_001 | 150 | tgggtcagcacttttgctgtgtatcttcatagaaggttggacaagatag | 199 |
| | | \|:\|.\|\|.\|...\|\|\|\|\|\|\|\|\|\|\|\|\|\|\|:\|\|\|\|\|\|\|\|\|.\|\|\|\|\|.\|\|\|.\|.\| | |
| EMBOSS_001 | 123 | tggatctgtgcttttgctgtgtatcttcatagaagattggataaggtcg | 172 |
| EMBOSS_001 | 200 | aagatgaaaggaatcttcatgaagattttgtattcatgaaaacgatacag | 249 |
| | | \|\|\|\|.\|\|\|...\|\|.\|\|\|\|\|\|\|\|\|\|\|\|\|\|:\|\|\|\|\|\|\|\|\|\|\|.\|\|\|\|.\|.\|\|.\|\| | |
| EMBOSS_001 | 173 | aagaggaagtaaaccttcatgaagattttgtattcataaaaaagctaaag | 222 |
| EMBOSS_001 | 250 | agatgcaacacaggagaaagatccttatccttactgaactgtgaggagat | 299 |
| | | \|:\|\|\|\|\|\|\|\|:.\|\|\|\|\|\|.\|\|\|\|.\|\|\|\|\|\|.\|\|\|\|\|\|\|\|\|\|\|\|\|\|\|\|\| | |
| EMBOSS_001 | 223 | agatgcaacaaggagaaggatcttatccttgctgaactgtgaggagat | 272 |
| EMBOSS_001 | 300 | taaaagccagtttgaaggctttgtgaaggatataatgttaaacaaagagg | 349 |
| | | .:.\|\|\|.\|\|.\|\|\|\|\|\|.\|.:\|\|\|.:\|\|\|\|\|\|\|\|.\|\|\|\|\|\|\|\|\|\|\|.\| | |
| EMBOSS_001 | 273 | gagaaggcaatttgaagaccttgtcaaggatataacgttaaacaaagaag | 322 |
| EMBOSS_001 | 350 | agacgaagaaagaaaacagctttgaaatgcaaaagggtgatcagaatcct | 399 |
| | | \| \|\|\|.\|:\|\|\|\|\|\|\|\|\|\|\|\|\|\|\|:\|\|\|\|\|\|\|\|.\|\|\|\|\|\|.\|\|.\|\|\|\|\| | |
| EMBOSS_001 | 323 | a---gaaaaagaaaacagctttgaaatgcaaagaggtgatgaggatcct | 369 |

FIG. 16A

```
EMBOSS_001    400  caaattgcggcacatgtcataagtgaggccagcagtaaaacaacatctgt    449
                   ||||||||.|||||.||..||||.||.||||.|||||||..||.||||.||
EMBOSS_001    370  caaattgcagcacacgttgtaagcgaagccaacagtaatgcagcatccgt    419

EMBOSS_001    450  gttacagtgggctgaaaaaggatactacaccatgagcaacaacttggtaa    499
                   ..|||||||||..|.||||||||||.||.||||||||..|.|||||||||
EMBOSS_001    420  tctacagtgggccaagaaaggatattataccatgaaaagcaacttggtaa    469

EMBOSS_001    500  ccctggaaaatgggaaacagctgaccgttaaaagacaaggactctattat    549
                   ..||.|||||||||||||||||||||.|||||||||.|||||||||||||
EMBOSS_001    470  tgcttgaaaatgggaaacagctgacggttaaaagagaaggactctattat    519

EMBOSS_001    550  atctatgcccaagtcaccttctgttccaatcgggaagcttcgagtcaa-g    598
                   .||||..|.|||||||||||||||.||.||||||||..|||||||||| |
EMBOSS_001    520  gtctacactcaagtcaccttctgctctaatcgggagccttcgagtcaacg    569

EMBOSS_001    599  ctccatttatagccagcctctgcctaaagtcccccgtagattcgagaga    648
                   | |||||.||.|.|.||||||.||.|||.||..||.||.|||..||||||
EMBOSS_001    570  c-ccattcatcgtcggcctctggctgaagcccagcagtggatctgagaga    618

EMBOSS_001    649  atcttactcagagctgcaaatacccacagttccgccaaaccttgcgggca    698
                   ||||||||||..||.|||||||||||||||||.||.|.|.|||||.|||
EMBOSS_001    619  atcttactcaaggcggcaaatacccacagttcctcccagctttgcgagca    668

EMBOSS_001    699  acaatccattcacttgggaggagtatttgaattgcaaccaggtgcttcgg    748
                   .||.||..|||||||||||.||||||||||||.|||.|.|.|||||||.|
EMBOSS_001    669  gcagtctgttcacttgggcggagtgtttgaattacaagctggtgcttctg    718

EMBOSS_001    749  tgtttgtcaatgtgactgatccaagccaagtgagccatggcactggcttc    798
                   ||||||||||.|||||.|||||||..|||||||||.|||.|...|||||||
EMBOSS_001    719  tgtttgtcaacgtgactgaagcagccaagtgatccacagagttggcttc    768

EMBOSS_001    799  acgtcctttggcttactcaaactctgaacagtg---tcaccttgcaggct    845
                   .|.||.||||||||||||||||||||||||||||    |..|||    |||||
EMBOSS_001    769  tcatcttttggcttactcaaactctgaacagtgcgctgtcct----aggct    815

EMBOSS_001    846  gtggtggagctgacgctggagtcttcataatacagcacag-cggttaag    894
                   |...|..|.|||||.|||||.|||||.|||...|||||||| ||.|||||.|
EMBOSS_001    816  gcagcagggctgatgctggcagtcttccctatacagca-agtcagttagg    864

EMBOSS_001    895  --ccacccctgtt-aactgcctatttataaccctaggatcctccttatg    942
                   ||..|||..|||| |||||||||||||||||||||||||||||||.|||
EMBOSS_001    865  acctgccctgtgttgaactgcctatttataaccctaggatcctcctcatg    914

EMBOSS_001    943  gagaactatttatta-tacactccaaggcatgtagaactgtaataagtg    990
                   ||||||||||||||  |||.|..|||||||..|||||.|||.|||||.|
EMBOSS_001    915  gagaactatttattatgtac-cccaaggcacatagagctggaataagag    963

EMBOSS_001    991  aattacaggtca-catgaaaccaaaacggg-ccctgctccataagagct   1037
                   ||||||||.||  ||..||.||.|| ||||.|||||||||.|||||||
EMBOSS_001    964  aattacagggcaggcaaaaatcccaa-gggaccctgctccctaagaact   1011

EMBOSS_001   1038  tatatatctgaagcagcaacccactgatgcagacatccagagagtccta   1087
                   ||.| |||||||.||||||||||||||||.|||||||.||||||
EMBOSS_001   1012  taca-atctgaaacagcaacccactgattcagacaacca----------   1050

EMBOSS_001   1088  tgaaaagacaaggccattatgcacaggt----tgaattctgagtaaacagc   1134
                   ||||||||||.|||||.||.|||||.|     .||..|||||..|||||.|
```

FIG. 16B

```
EMBOSS_001      1051 -gaaaagacaaagccataatacacagatgacagagctctgatgaaacaac   1099

EMBOSS_001      1135 agataact-tgccaagttcagtttttgt-ttctttgcgtgcagtgtctt   1180
                     ||||||||  ||    ||..|||||||||| ||.|.||.||   |||||.|
EMBOSS_001      1100 agataactaatg---agcacagttttgttgtttatgggt---gtgtcgt   1143

EMBOSS_001      1181 tccatggataatgcatttgatttatcagtgaagatgcagaagggaaatgg   1230
                     ||.|||||.|.||.|.||||.|||.|||.||||||||||||||||.||..|
EMBOSS_001      1144 tcaatggacagtgtacttgacttaccagggaagatgcagaagggcaactg   1193

EMBOSS_001      1231 ggagcctcagctcacattcagttatggttgactctgggttcctatggcct   1280
                     .||||||||||||||.||.|||||||||||| ||||||||         |||
EMBOSS_001      1194 tgagcctcagctcacaatctgttatggttgac-ctgggctc-------cct   1236

EMBOSS_001      1281 tgttggaggggccaggctctagaacgtctaacacagtggagaaccgaaa   1330
                             || |||.||||.|.|
EMBOSS_001      1237 ------------gc-ggccctagtagg                        1250

EMBOSS_001      1331 cccccccccccccgccaccctctcggacagttattcattctctttc      1380

EMBOSS_001      1251                                                     1250

EMBOSS_001      1381 aatctctctctccatctctctctttcagtctctctctctcaacctctt    1430

EMBOSS_001      1251                                                     1250

EMBOSS_001      1431 tcttccaatctctctttctcaatctctctgtttcccttgtcagtctctt    1480

EMBOSS_001      1251                                                     1250

EMBOSS_001      1481 ccctccccagtctctcttctcaatcccccttctaacacacacacac    1530

EMBOSS_001      1251                                                     1250

EMBOSS_001      1531 acacacacacacacacacacacacacacacacacacacacacacac    1580

EMBOSS_001      1251                                                     1250

EMBOSS_001      1581 agagtcaggccgttgctagtcagttctcttctttccaccctgtccctatc   1630

EMBOSS_001      1251                                                     1250

EMBOSS_001      1631 tctaccactatagatgagggtgaggagtagggagtgcagccctgagcctg   1680

EMBOSS_001      1251                                                     1250

EMBOSS_001      1681 cccactcctcattacgaaatgactgtatttaaaggaaatctattgtatct   1730

EMBOSS_001      1251                                                     1250

EMBOSS_001      1731 acctgcagtctccattgtttccagagtgaacttgtaattatcttgttatt   1780

EMBOSS_001      1251                                                     1250

EMBOSS_001      1781 tattttttgaataataaagacctcttaacattaaaa    1816

EMBOSS_001      1251                                                     1250
```

FIG. 16C

```
########################################
# Program:  needle
# Rundate:  Tue Oct 05 21:40:43 2004
# Align_format: srspair
# Report_file: /ebi/extserv/old-work/needle-20041005-21404327122895.output
########################################
#=======================================

# Aligned_sequences: 2
# 1: EMBOSS_001
# 2: EMBOSS_001
# Matrix: EBLOSUM62
# Gap_penalty: 10.0
# Extend_penalty: 0.5

# Length: 261
# Identity:     202/261 (77.4%)
# Similarity:   225/261 (86.2%)
# Gaps:           1/261 ( 0.4%)
# Score: 1032.0

#=======================================
```

| | | |
|---|---|---|
| HUMAN CD4OL | 1   MIETYNQTSPRSAATGLPISMKIFMYLLTVFLITQMIGSALFAVYLHRRL | 50 |
| | ||||:|.||||.|||||.||||||||||||||||||.||||||||| | |
| MOUSE CD4OL | 1   MIETYSQPSPRSVATGLPASMKIFMYLLTVFLITQMIGSVLFAVYLHRRL | 50 |
| EMBOSS_001 | 51  DKIEDERNLHEDFVFMKTIQRCNTGERSLSLLNCEEIKSQFEGFVKDIML | 100 |
| | ||:|:|.||||||||:|.::|||.||.|||||||||::.|||..||||.| | |
| EMBOSS_001 | 51  DKVEEEVNLHEDFVFIKKLKRCNKGEGSLSLLNCEEMRRQFEDLVKDITL | 100 |
| EMBOSS_001 | 101 NKEETKKENSFEMQKGDQNPQIAAHVISEASSKTTSVLQWAEKGYYTMSN | 150 |
| | |||| |:|||||||:||::|||||||:||:|...||||||:|||||||.: | |
| EMBOSS_001 | 101 NKEE-KKENSFEMQRGDEDPQIAAHVVSEANSNAASVLQWAKKGYYTMKS | 149 |
| EMBOSS_001 | 151 NLVTLENGKQLTVKRQGLYYIYAQVTFCSNREASSQAPFIASLCLKSPGR | 200 |
| | |||.||:||||||||:|||:|.|||||||||.|||.:|||..|.||.... | |
| EMBOSS_001 | 150 NLVMLENGKQLTVKREGLYYVYTQVTFCSNREPSSQRPFIVGLWLKPSSG | 199 |
| EMBOSS_001 | 201 FERILLRAANTHSSAKPCGQQSIHLGGVFELQPGASVFVNVTDPSQVSHG | 250 |
| | .|||||:|||||||::.|.|||:||||||||.||||||||||:.|||.|. | |
| EMBOSS_001 | 200 SERILLKAANTHSSSQLCEQQSVHLGGVFELQAGASVFVNVTEASQVIHR | 249 |
| EMBOSS_001 | 251 TGFTSFGLLKL     261 | |
| | .||:||||||| | |
| EMBOSS_001 | 250 VGFSSFGLLKL     260 | |

FIG. 17

MATURE DENDRITIC CELL COMPOSITIONS AND METHODS FOR CULTURING SAME

CROSS REFERENCE TO RELATED APPLICATIONS

This application is a continuation of U.S. application Ser. No. 11/246,387, filed 7 Oct. 2005 (now U.S. Pat. No. 8,822,223, issued 2 Sep. 2014), which claims priority to U.S. provisional application 60/522,512, filed 7 Oct. 2004, the contents of each of which are hereby incorporated by reference.

FIELD OF THE INVENTION

The present invention relates to the generation of mature dendritic cells and their use in cell therapy and to educate immune effector cells. The mature dendritic cells can be generated from immature dendritic cells.

BACKGROUND

Cell therapy utilizes modified antigen presenting cells (APCs) or immune effector cells to initiate an immune response in a patient. Antigen presenting cells are central to cell therapy because they initiate the immune response. Indeed, they are the only cells capable of inducing a primary immune response from the T lymphocytes.

Dendritic cells (DC) are the most potent APCs involved in adaptive immunity. They coordinate the initiation of immune responses by naive T cells and B cells and induce antigen-specific cytotoxic T lymphocyte (CTL) responses. DCs are specialized in several ways to prime helper and killer T cells in vivo. For example, immature DCs that reside in peripheral tissues are equipped to capture antigens and to produce immunogenic MHC-peptide complexes. In response to maturation-inducing stimuli such as inflammatory cytokines, immature DCs develop into potent T cell stimulators by upregulating adhesion and costimulatory molecules. At the same time, they migrate into secondary lymphoid organs to select and stimulate rare antigen-specific T cells. However, potent stimulation of T cells occurs only after DC maturation, a process that increases the availability of MHC/peptide complexes on the cell surface, in addition to co-stimulatory molecules, that direct the effector function of the responding T-cells. Indeed, immature DCs may be harmful in anti-tumor and other immunotherapies because they can induce immunotolerance rather than immunostimulation.

Co-stimulation is typically necessary for a T cell to produce sufficient cytokine levels that induce clonal expansion. One characteristic of dendritic cells which makes them potent antigen presenting cells is that they are rich in co-stimulatory molecules of the immune response, such as the molecules CD80 and CD86, which activate the molecule CD28, on T lymphocytes. In return, T-helper cells express CD40L, which ligates CD40 on DCs. These mutual interactions between DCs and T-cells leads to 'maturation' of the former, and the development of effector function in the latter. The expression of adhesion molecules, like the molecule CD54 or the molecule CD11a/CD18, facilitate the co-operation between the dendritic cells and the T-cells. Another special characteristic of dendritic cells is to deploy different functions depending on their stage of differentiation. Thus, the capture of the antigen and its transformation are the two principal functions of the immature dendritic cell, whereas its capacities to present the antigen in order to stimulate the T cells increases as the dendritic cells migrate into the tissues and the lymphatic ganglia. This change of functionality corresponds to a maturation of the dendritic cell. Thus, the passage of the immature dendritic cell to the mature dendritic cell represents a fundamental step in the initiation of the immune response. Traditionally, this maturation was followed by monitoring the change of the surface markers on the DCs during this process. Some of the more important cell surface markers characteristic of the different stages of maturation of the dendritic cells are summarized in Table I, below. However, the surface markers can vary depending upon the maturation process.

TABLE I

| Cell type | Surface markers |
|---|---|
| Hematopoietic stem cell | CD34+ |
| Monocytes | CD14++, DR+, CD86+, CD16+/−, CD54+, CD40+ |
| Immature dendritic cell | CD14+/−, CD16−, CD80+/−, CD83−, CD86+, CD1a+, CD54+, DQ+, DR++ |
| Mature dendritic cell | CD14−, CD83++, CD86++, CD80++, DR+++, DQ++, CD40++, CD54++, CD1a +/− |

Mature DCs are currently preferred to immature DCs for immunotherapy. Only fully mature DC progeny lack GM-CSF Receptor (GM-CSF-R) and remain stably mature upon removal/in the absence of GM-CSF. Also, mature DCs have been shown to be superior in inducing T cell responses in vitro and in vivo. In contrast, immature DCs are reported to induce tolerance in vitro (Jonuleit et al. (2000) Exp. Med. 192:1213) as well as in vivo (Dhodapkar et al. (2001) Exp. Med. 193:233) by inducing regulatory T cells. Mature dendritic cells also are useful to take up and present antigen to T-lymphocytes in vitro or in vivo. The modified, antigen presenting DCs and/or T cells educated from these modified DCs have many applications, including diagnostic, therapy, vaccination, research, screening and gene delivery.

It is difficult to isolate mature dendritic cells from peripheral blood because less than 1% of the white blood cells belongs to this category. Mature DCs are also difficult to extract from tissues. This difficulty, in combination with the potential therapeutic benefit of DCs in cell therapy, has driven research and development toward new methods to generate mature dendritic cells using alternative sources. Several methods are reported to produce mature DCs from immature dendritic cells.

For example, Jonuleit et al. (Eur J Immunol (1997) 12:3135-3142) disclose maturation of immature human DCs by culture in medium containing a cytokine cocktail (IL-1β, TNF-α, IL-6 and PGE$_2$).

WO 95/28479 discloses a process for preparing dendritic cells by isolating peripheral blood cells and enriching for CD34$^+$ blood precursor cells, followed by expansion with a combination of hematopoietic growth factors and cytokines.

European Patent Publication EP-A-0 922 758 discloses the production of mature dendritic cells from immature dendritic cells derived from pluripotential cells having the potential of expressing either macrophage or dendritic cell characteristics. The method requires contacting the immature dendritic cells with a dendritic cell maturation factor containing IFN-γ.

European Patent Publication EP-B-0 633930 teaches the production of human dendritic cells by first culturing human CD34$^+$ hematopoietic cells (i) with GM-CSF, (ii) with TNF-α and IL-3, or (iii) with GM-CSF and TNF-α to induce the formation of CD1a+ hematopoietic cells.

Patent Publication No. 2004/0152191 discloses the maturation of dendritic cells by contacting them with RU 41740.

U.S. Patent Publication No. 2004/0146492 teaches a process for producing recombinant dendritic cells by transforming hematopoietic stem cells followed by differentiation of the stem cells into dendritic cells by culture in medium containing GM-CSF.

U.S. Patent Publication No. 2004/0038398 discloses methods for the preparation of substantially purified populations of DCs and monocytes from the peripheral blood of mammals. Myeloid cells are isolated from the mammal and DCs are separated from this population to yield an isolated subpopulation of monocytes. DCs are then enriched by negative selection with anti-CD2 antibodies to remove T cells.

Although mature DCs are functionally competent and are therefore useful to induce antigen-specific T cells, not all mature DCs are optimized to induce these responses. It has been shown that some mature DCS may also stimulate T helper cells by secreting IL-12. Macatonia et al. (1995) Immunol. 154:507 1; Ahuja et al. (1998) Immunol. 161:868 and Unintford et al. (1999) Immunol. 97:588. IL-12 also has been shown to enhance antigen-specific CD8+ T cell response to antigen in an animal model. Schmidt et al. (1999) Immunol. 163:2561.

Mosca et al. (2000) Blood 96:3499, disclose that culture of DC in AIM V medium containing both soluble CD40L trimer and IFNγ 1b results in increased IL-12 expression in comparison to culture in medium containing only soluble CD40L trimer.

Koya et al. (2003) J. Immunother. 26(5):451 report that IL-12 expression can be enhanced by tranducing immature DCs, in the presence of IFNγ, with a lentiviral vector encoding CD40 Ligand. Greater than 90% of the CD40L transduced DCs expressed CD83 on their cell surface. Unfortuantely, lentiviral transduced cells are not suitable for therapeutic purposes, and proviral integration into the genome of the transduced cell can result in leukemia. Furthermore, persistant expression of CD40L may have detrimental effects on APC function and viability.

This work supplemented the earlier work of Mackey, et al. (1998) J. Immunol. 161:2094 who reported that in vivo, DCs require maturation via CD40 to generate anti-tumor immunity. Similarly, Kuniyoshi, J. S. et al. (1999) Cell Immunol. 193:48 have shown that DCs treated with soluble trimeric CD40 Ligand plus IFN-γ stimulated potent T-cell proliferation and induced T cells with augmented antigen-specific lysis. Kalady, M. F. et al. (2004) J. Surg. Res. 116:24, reported that human monocytederived DCs transfected with mRNA encoding melanoma antigen MART-1 or influenza M1 matrix protein exposed to different maturation stimuli added either simultaneously or sequentially showed variability in antigen presentation, IL-12 secretion and immunogenicity of effector T cells raised in the presence of these DCs. Most importantly, this study showed that the application of a 'cytokine cocktail' consisting of IL-1β, TNF-α, IL-6 and PGE$_2$, followed by extracellular soluble CD40L protein was superior to applying all the agents simultaneously. However, these authors did not study the combination of IFN-γ signaling with transient CD40L signalling in a sequential process. Moreover, despite the production of IL-12 when IFN-γ and CD40L are concomitantly added to the culture medium, the recent prior art shows that the resulting DCs are actually immunosuppressive, rather than pro-inflammatory (Hwu et al. (2000) J. Immunol. 164: 3596; Munn et al. (2002) 297:1867; and Grohmann et al. (2003) Trends Immunol. 24:242) due to the induction of an enzyme that metabolized tryptophan resulting in the starvation of responder T-cells that then fail to proliferate. Thus, current literature suggests that the combination of IFN-γ and CD40L should not increase immunopotency. The present invention addresses the long-felt need to provide improved methods for DC maturation and mature DCs with enhanced immunopotentcy.

SUMMARY OF THE INVENTION

Applicants have discovered that potent immunostimulation occurs when immature dendritic cells are sequentially signaled with a first signal comprising an interferon gamma receptor (IFN-γR) agonist followed by a second signal comprising a CD40 agonist. Accordingly, this invention provides a method for preparing mature dendritic cells (DCs), comprising the sequential steps of: (a) signaling isolated immature dendritic cells (iDCs) with a first signal comprising an interferon gamma receptor (IFN-γR) agonist, and optionally a TNF-αR agonist, to produce signaled dendritic cells; and (b) signaling said signaled dendritic cells with a second transient signal comprising an effective amount of a CD40 agonist to produce CCR7+ mature dendritic cells.

In preferred embodiments, the immature DCs are further contacted with PGE$_2$ and optionally with TNF-α. In alternative embodiments the method further comprises contacting the immature DCs, signaled DCs and/or CCR7+ mature dendritic cells with a compound selected from the group consisting of: galactosylceramides, glycosylceramides, galactofuranosylceramides, arabinopyranosylceramides, α-C-galactosylceramides and α-S-galactosylceramides. Preferably the compound is a galactosylceramide. Most preferably, the galactosylceramide is (2S,3S,4R)-1-O-(alpha-D-galactopyranosyl)-2-(N-hexacosanoylamino)-1,3,4-octadecanetriol (KRN7000).

In another embodiment of the invention, the IFN-γR agonist can be replaced by a tumor necrosis factor alpha receptor (TNF-αR) agonist. Thus, the invention provides a method for preparing an enriched population of mature dendritic cells (DCs), comprising sequentially signaling immature dendritic cells with a first signal comprising a tumor necrosis factor alpha receptor (TNF-αR) agonist followed by a second signal comprising a CD40 agonist, thereby preparing an enriched population of mature dendritic cells, wherein said signaling is in the absence of an effective amount of IL-1β or IL-6. Preferably, the immature DCs are further contacted with PGE$_2$.

Preferred IFN-γR agonists are mammalian IFN-γ, preferably human IFN-γ and active fragments thereof. Preferred TNF-αR agonists are mammalian TNF-α, preferably human TNF-α and active fragments thereof. Preferred CD40 agonists are mammalian CD40 Ligands (CD40L), preferably human CD40L and active fragments and variants thereof, as well as agonistic antibodies to CD40 receptor. Signaling can be initiated by providing the signaling agonist in the culture medium, introduction of the agonist into the cell, and/or upon translation within the dendritic cell of an mRNA encoding an agonistic polypeptide. The method can be practiced in vivo or ex vivo. Dendritic cells matured ex vivo according to the methods of the invention can then be administered to the subject to induce or enhance an immune response.

Each of the dendritic cells can be further modified by the administration of an immunogen to the DC. The DC will take up and process the immunogen, and display it on its cell surface. The immunogen can be delivered in vivo or ex vivo. The matured, cultured DCs can be administered to a subject to induce or enhance an immune response. In yet a further embodiment, the antigen loaded mature DCs are used to educate naïve immune effector cells.

In another aspect, the invention provides a composition comprising in vitro matured dendritic cells, such as $CD83^+$ $CCR7^-$ mature DCs and $CD83^+$ $CCR7^+$ mature DCs. Mature dendritic cells of the invention express increased levels of IL-12 in comparison to immature dendritic cells, and/or express less than 500 pg IL-10 per million dendritic cells. The compositions of the invention are useful to raise an immune response in a subject by administering to the subject an effective amount of the population.

BRIEF DESCRIPTION OF THE SEQUENCE LISTING

SEQ ID NO:1 is a human CD40L cDNA. Nucleotides 40 to 825 represent the coding region, including the ATG translation start codon and the TGA translational stop codon.

SEQ ID NO:2 is an amino acid sequence for full length human CD40L protein.

SEQ ID NO:3 is a human CD40 cDNA. Nucleotides 67 to 522 represent the coding region, including the ATG translation start codon and the TAG translational stop codon.

SEQ ID NO:4 is an amino acid sequence for human CD40 (the receptor for CD40L).

SEQ ID NO:5 is a human IFN-γ cDNA. Nucleotides 109 to 609 represent the coding region, including the ATG translation start codon and the translational stop codon.

SEQ ID NO:6 is an amino acid sequence for human IFN-γ.

SEQ ID NO:7 is a human TNF-α cDNA. Nucleotides 170 to 971 represent the coding region, including the ATG translation start codon and the TGA translational stop codon.

SEQ ID NO:8 is an amino acid sequence for human TNF-α.

SEQ ID NO:9 is a mouse CD40L cDNA. Nucleotides 13 to 795 represent the coding region, including the ATG translation start codon and the TGA translational stop codon.

SEQ ID NO:10 is an amino acid sequence for full length mouse CD40L protein.

SEQ ID NO:11 is a CD40L 5' primer.

SEQ ID NO:12 is a CD40L 3' primer.

SEQ ID NO:13 is the DNA sequence corresponding to an optimized human CD40L mRNA.

SEQ ID NO:14 is the CD40 Receptor 3'UTR.

SEQ ID NO:15 is the untranslated region of final exon of the human beta-actin 3' UTR.

SEQ ID NO:16 is the minimal functional element of the human beta-actin 3' UTR.

SEQ ID NO:17 is the simian rotavirus Gene 6 3'UTR.

SEQ ID NO:18 is the minimal functional element of the simian rotavirus Gene 6 3'UTR.

SEQ ID NO:19 is the human Hsp70 5'UTR (HSPA1A).

SEQ ID NO:20 is the mouse VEGF 5'UTR.

SEQ ID NO:21 is the minimal functional element of the mouse VEGF 5'UTR.

SEQ ID NO:22 is the Spleen Necrosis Virus LTR RU5 Region.

SEQ ID NO:23 is the Tobacco Etch Virus 5' Leader sequence.

SEQ ID NOs:24-25 are HLA-A201 restricted MART-APL peptide, native peptide and PSA-1 peptide, respectively.

BRIEF DESCRIPTION OF THE FIGURES

In FIG. 6A, DCs were transfected with 4 μg CD40L mRNA per million cells and analyzed at various time points. The majority of CD40L is localized within an intracellular compartment as demonstrated by a 4 hour time point where surface expression is considerably lower. FIG. 6B shows that significant intracellular expression is evident at 60 minutes with 27% positive DCs and increasing to 79% by 3 hours.

FIG. 11A shows that maturation of DCs using co-transfection with MART-APL mRNA as source of antigen, and CD40L mRNA, with the addition of soluble interferon-γ/$PGE_2$ invokes an effective CTL response, whereas FIG. 11B shows that DCs transfected with MART-APL mRNA, but matured with a 'cytokine cocktail', do not. T2-PSA: T2 cells pulsed with an HLA-A2 restricted peptide from prostate-specific antigen (PSA) as a negative control target. MART-T2: T2 cells pulsed with the HLA-A2 restricted MART epitope in its native sequence. MART-APL-T2: T2 cells pulsed with the HLA-A2 restricted MART epitope as the preferred 'altered peptide ligand'.

FIGS. 16A, 16B and 16C show the alignment of the human (SEQ ID NO:1) and mouse (SEQ ID NO:9) CD40L cDNAs. FIGS. 16A, 16B and 16C represent 3 consecutive pages of the alignment of SEQ ID NOs:1 and 9.

FIG. 17 shows the alignment of the human (SEQ ID NO:2) and mouse (SEQ ID NO:10) CD40L proteins.

MODES FOR CARRYING OUT THE INVENTION

Figure 1:
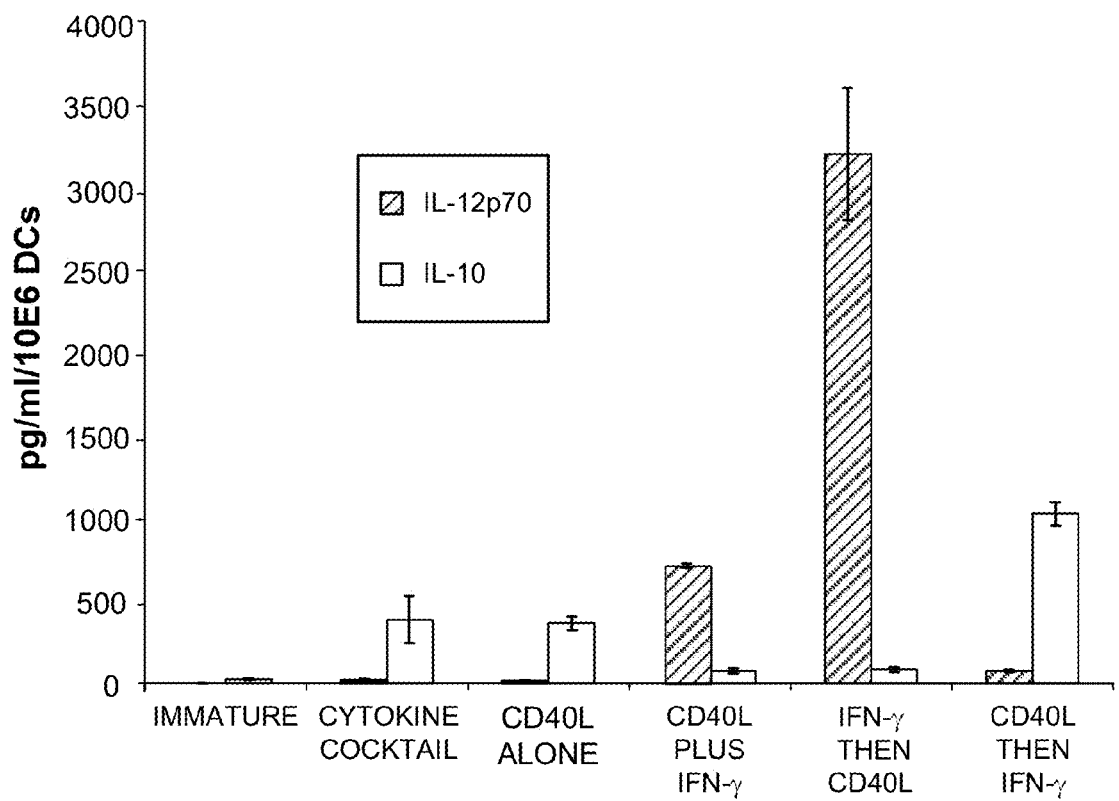
FIG. 1 shows that sequential maturation of DCs with IFN-γ then soluble CD40L results in optimal IL-12p70 secretion. DCs were matured with cytokine cocktail, soluble CD40L alone, or with soluble CD40L plus IFN-γ. Pre-incubation of immature DCs with 1000 U/ml of IFN-γ for 18 hrs, followed by addition of soluble CD40L for a further 18 hrs results in maximum IL-12p70 release. Applying soluble CD40L first, followed by IFN-γ is perceived as a negative signal, with minimal IL-12p70 release, accompanied by IL-10.

Throughout this disclosure, various publications, patents and published patent specifications are referenced by an identifying citation. The disclosures of these publications, patents and published patent specifications are hereby specifically incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. MOLECULAR CLONING: A LABORATORY MANUAL, $2^{nd}$ edition (1989); CURRENT PROTOCOLS IN MOLECULAR BIOLOGY (Ausubel et al. eds. (1987)); the series METHODS IN ENZYMOLOGY (Academic Press, Inc.); PCR: A PRACTICAL APPROACH (M. MacPherson et al. IRL Press at Oxford University Press (1991)); PCR 2: A PRACTICAL APPROACH (MacPherson, Hames and Taylor eds. (1995)); ANTIBODIES, A LABORATORY MANUAL (Harlow and Lane eds. (1988)); USING ANTIBODIES, A LABORATORY MANUAL (Harlow and Lane eds. (1999)); and ANIMAL CELL CULTURE (Freshney ed. (1987)).

Definitions

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated, that the reagents described herein are merely exemplary and that equivalents of such are known in the art.

The term "antigen" is well understood in the art and includes substances which are immunogenic, i.e., immunogen. It will be appreciated that the use of any antigen is envisioned for use in the present invention and thus includes, but is not limited to a self-antigen (whether normal or disease-related), an infectious antigen (e.g., a microbial antigen, viral antigen, etc.), or some other foreign antigen (e.g., a food component, pollen, etc.). The term "antigen" or alternatively, "immunogen" applies to collections of more than one immunogen, so that immune responses to multiple immunogens may be modulated simultaneously. Moreover, the term includes any of a variety of different formulations of immunogen or antigen.

A "native" or "natural" or "wild-type" antigen is a polypeptide, protein or a fragment which contains an epitope, which has been isolated from a natural biological source, and which can specifically bind to an antigen receptor, when presented as an MHC/peptide complex, in particular a T cell antigen receptor (TCR), in a subject.

The term "tumor associated antigen" or "TAA" refers to an antigen that is associated with a tumor. Examples of well known TAAs include gp100, MART and MAGE.

The terms "major histocompatibility complex" or "MHC" refers to a complex of genes encoding cell-surface molecules that are required for antigen presentation to T cells and for rapid graft rejection. In humans, the MHC is also known as the "human leukocyte antigen" or "HLA" complex. The proteins encoded by the MHC are known as "MHC molecules" and are classified into Class I and Class II MHC molecules. Class I MHC molecules include membrane heterodimeric proteins made up of an a chain encoded in the MHC noncovalently linked with the $\beta_2$-microglobulin. Class I MHC molecules are expressed by nearly all nucleated cells and have been shown to function in antigen presentation to $CD8^+$ T cells. Class I molecules include HLA-A, B, and C in humans. Class II MHC molecules also include membrane heterodimeric proteins consisting of noncovalently associated α and β chains. Class II MHC molecules are known to function in $CD4^+$ T cells and, in humans, include HLA-DP, -DQ, and -DR.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B-cells, endothelial cells, activated T-cells, and dendritic cells; or other molecules, naturally occurring or synthetic, such as purified MHC Class I molecules complexed to β2-microglobulin. While many types of cells may be capable of presenting antigens on their cell surface for T-cell recognition, only dendritic cells have the capacity to present antigens in an efficient amount to activate naive T-cells for cytotoxic T-lymphocyte (CTL) responses.

The term "dendritic cells (DCs)" refers to a diverse population of morphologically similar cell types found in a variety of lymphoid and non-lymphoid tissues, Steinman (1991) Ann. Rev. Immunol. 9:271-296. Dendritic cells constitute the most potent and preferred APCs in the organism. While the dendritic cells can be differentiated from monocytes, they possess distinct phenotypes. For example, a particular differentiating marker, CD14 antigen, is not found in dendritic cells but is possessed by monocytes. Also, mature dendritic cells are not phagocytic, whereas the monocytes are strongly phagocytosing cells. It has been shown that mature DCs can provide all the signals necessary for T cell activation and proliferation.

The term "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates.

A "naïve" immune effector cell is an immune effector cell that has never been exposed to an antigen capable of activating that cell. Activation of naive immune effector cells requires both recognition of the peptide:MHC complex and the simultaneous delivery of a costimulatory signal by a professional APC in order to proliferate and differentiate into antigen-specific armed effector T cells.

"Immune response" broadly refers to the antigen-specific responses of lymphocytes to foreign substances. Any substance that can elicit an immune response is said to be "immunogenic" and is referred to as an "immunogen". All immunogens are antigens, however, not all antigens are immunogenic. An immune response of this invention can be humoral (via antibody activity) or cell-mediated (via T cell activation).

As used herein, the term "educated, antigen-specific immune effector cell", is an immune effector cell as defined above, which has previously encountered an antigen. In contrast to its naïve counterpart, activation of an educated, antigen specific immune effector cell does not require a costimulatory signal. Recognition of the peptide:MHC complex is sufficient.

"Activated", when used in reference to a T cell, implies that the cell is no longer in $G_0$ phase, and begins to produce one or more of cytotoxins, cytokines and other related membrane-associated proteins characteristic of the cell type (e.g., $CD8^+$ or $CD4^+$), and is capable of recognizing and binding any target cell that displays the particular peptide/MHC complex on its surface, and releasing its effector molecules.

As used herein, the term "inducing an immune response in a subject" is a term understood in the art and refers to an increase of at least about 2-fold, or alternatively at least about 5-fold, or alternatively at least about 10-fold, or alternatively at least about 100-fold, or alternatively at least about 500-fold, or alternatively at least about 1000-fold or more in an immune response to an antigen (or epitope) which can be detected or measured, after introducing the antigen (or epitope) into the subject, relative to the immune response (if any) before introduction of the antigen (or epitope) into the subject. An immune response to an antigen (or epitope), includes but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody).

"Co-stimulatory molecules" are involved in the interaction between receptor-ligand pairs expressed on the surface of antigen presenting cells and T cells. Research accumulated over the past several years has demonstrated convincingly that resting T cells require at least two signals for induction of cytokine gene expression and proliferation (Schwartz, R. H. (1990) Science 248: 1349-1356 and Jenkins, M. K. (1992) Immunol. Today 13:69-73). One signal, the one that confers specificity, can be produced by interaction of the TCR/CD3 complex with an appropriate MHC/peptide complex. The second signal is not antigen specific and is termed the "co-stimulatory" signal. This signal was originally defined as an activity provided by bone-marrow-derived accessory cells such as macrophages and dendritic cells, the so called "professional" APCs. Several molecules have been shown to enhance co-stimulatory activity. These are heat stable antigen (HSA) (Liu, Y. et al. (1992) 3. Exp. Med. 175:437-445), chondroitin sulfate-modified MHC invariant chain (li-CS) (Naujokas, M. F. et al. (1993) Cell 74:257-268), intracellular adhesion molecule 1 (ICAM-1) (Van Seventer, G. A. (1990)]. Immunol. 144:4579-4586), B7-1, and B7-2/B70 (Schwartz, R. H. (1992) Cell 71:1065-1068). These molecules each appear to assist co-stimulation by interacting with their cognate ligands on the T cells.

Co-stimulatory molecules mediate co-stimulatory signal(s), which are necessary, under normal physiological conditions, to achieve full activation of naïve T cells. One exemplary receptor-ligand pair is the B7 family of co-stimulatory molecule on the surface of APCS and its counterreceptor CD28 or CTLA-4 on T cells (Freeman, et al. (1993) Science 262:909-911; Young, et al. (1992)]. Clin. Invest. 90:229 and Nabavi, et al. (1992) Nature 360:266-268). Other important co-stimulatory molecules are CD40, and CD54. The term "costimulatory molecule" encompasses any single molecule or combination of molecules which, when acting together with a MHC/peptide complex bound by a TCR on the surface of a T cell, provides a co-stimulatory effect which achieves activation of the I cell that binds the peptide. The term thus encompasses B7, or other co-stimulatory molecule (s) on an antigen-presenting matrix such as an APC, fragments thereof (alone, complexed with another molecule(s), or as part of a fusion protein) which, together with MHC complex, binds to a cognate ligand and results in activation of the T cell when the TCR on the surface of the T cell specifically binds the peptide. It is intended, although not always explicitly stated, that molecules having similar biological activity as wild-type or purified co-stimulatory molecules (e.g., recombinantly produced or muteins thereof) are intended to be used within the spirit and scope of the invention.

As used herein, the term "cytokine" refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin-3 (IL-3), interleukin-6 (IL-6), interleukin-12 (IL-12), G-CSF, granulocyte macrophage-colony stimulating factor (GM-CSF), interleukin-1 alpha (IL-1α), interleukin-1L (IL-11), MIP-11, leukemia inhibitory factor (LIF), c-kit ligand, thrombopoietin (TPO) and flt3 ligand. One embodiment of the present invention includes culture conditions in which an effective amount of IL-1β and/or IL-6 is excluded from the medium. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The terms "polynucleotide", "nucleic acid" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules. As used herein, mRNA refers to an RNA that can be translated in a dendritic cell. Such mRNAs typically are capped and have a ribosome binding site (Kozak sequence) and a translational initiation codon.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein.

The term "genetically modified" means containing and/or expressing a foreign gene or nucleic acid sequence which in turn, modifies the genotype or phenotype of the cell or its progeny. In other words, it refers to any addition, deletion or disruption to a cell's endogenous nucleotides.

As used herein, "expression" refers to the processes by which polynucleotides are transcribed into mRNA and mRNA is translated into peptides, polypeptides, or proteins. If the polynucleotide is derived from genomic DNA of an appropriate eukaryotic host expression may include splicing of the mRNA. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al. (1989) supra). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods known in the art, for example, the methods herein below for constructing vectors in general.

"Under transcriptional control" is a term understood in the art and indicates that transcription of a polynucleotide sequence, usually a DNA sequence, depends on its being operatively linked to an element which contributes to the initiation of, or promotes, transcription. "Operatively linked" refers to a juxtaposition wherein the elements are in an arrangement allowing them to function.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

"Gene delivery," "gene transfer," "transfection" and the like as used herein, are terms referring to the introduction of an exogenous polynucleotide into a host cell, irrespective of the method used for the introduction. Transfection refers to delivery of any nucleic acid to the interior of a cell. Gene delivery refers to the delivery of a nucleic acid that may be integrated into the host cell's genome, or that may replicate independently of the host cell genome. Gene delivery or gene transfer does not refer to introduction of an mRNA into a cell. Transfection methods include a variety of techniques such as electroporation, protein-based, lipid-based and cationic ion based nucleic acid delivery complexes, viral vectors, "gene gun" delivery and various other techniques known to those of skill in the art. The introduced polynucleotide can be stably maintained in the host cell or may be transiently expressed. In preferred embodiments, an mRNA is introduced into a DC and is transiently expressed. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Zaks et al. (1999) Nat. Med. 7:823-827. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, "retroviral vector" refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad), pseudo adenoviral or adeno-associated virus (MV), vector construct refers to the polynucleotide comprising the viral genome or part thereof, and a transgene. Adenoviruses (Ads) are a relatively well characterized, homogenous group of viruses, including over 50 serotypes. (See, e.g., WO 95/27071). Ads are easy to grow and do not require integration into the host cell genome. Recombinant Ad-derived vectors, particularly those that reduce the potential for recombination and generation of wild-type virus, have also been constructed. (See, WO 95/00655 and WO 95/11984). Wild-type MV has high infectivity and specificity integrating into the host cell's genome. (See, Hermonat and Muzyczka (1984) Proc. Natl. Acad. Sci. USA 81:6466-6470 and Lebkowski et al. (1988) Mol. Cell. Biol. 8:3988-3996).

Vectors that contain both a promoter and a cloning site into which a polynucleotide can be operatively linked are known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, nucleic acids or proteins of this invention can be conjugated to antibodies or binding fragments thereof which bind cell surface antigens, e.g., TCR, CD3 or CD4.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Stringent hybridization conditions are as follows: Prehybridization of filters containing a nucleic acid of interest is carried out for 8 hrs to overnight at 65° C. in buffer composed of 6×SSC, 50 mM Tris-HCl (pH 7.5), 1 mM EDTA, 0.02% Ficoll, 0.02% BSA, and 500 µg/ml denatured salmon sperm DNA. Filters are hybridized for 48 hrs at 65° C., the preferred hybridization temperature, in prehybridization mixture containing 100 µg/ml denatured salmon sperm DNA and 5-20×$10^6$ cpm of $^{32}$P-labeled probe. Subsequently, filter washes are performed at 37° C. for 1 h in a solution containing 2×SSC, 0.01% Ficoll, and 0.01% BSA, followed by a wash in 0.1×SSC at 50° C. for 45 min. Following the wash steps, the hybridized probes are detectable by autoradiography. Such methods are well known in the art and cited in Sambrook et al., 1989; and Ausubel et al., 1989.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity is be determined using the well known BLAST alignment program and the default parameters. Alternative programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+ EMBL+DDBJ+PDB+GenBank CDS translations+SwissProtein+SPupdate+PIR. Details of these programs can be found at the following world wide web address: ncbi.nlm.nih.gov/cgi-bin/BLAST.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragment(s) thereof, does not require "isolation" to distinguish it from its naturally occurring counterpart. In addition, a "concentrated", "separated" or "diluted" polynucleotide, peptide, polypeptide, protein, antibody, or fragment(s) thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragment(s) thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as its glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature. A mammalian cell, such as dendritic cell is isolated if it is removed from the anatomical site from which it is found in an organism.

"Host cell," "target cell" or "recipient cell" are intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

A "subject" is a vertebrate, preferably a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation of an immune response with a particular culture condition, it is generally preferable to use a positive control and a negative control.

By "cancer" is meant the abnormal presence of cells which exhibit relatively autonomous growth, so that a cancer cell exhibits an aberrant growth phenotype characterized by a significant loss of cell proliferation control. Cancerous cells can be benign or malignant. In various embodiments, the cancer affects cells of the bladder, blood, brain, breast, colon, digestive tract, lung, ovaries, pancreas, prostate gland, or skin. The definition of a cancer cell, as used herein, includes not only a primary cancer cell, but also any cell derived from a cancer cell ancestor. This includes metastasized cancer cells, and in vitro cultures and cell lines derived from cancer cells. Cancer includes, but is not limited to, solid tumors, liquid tumors, hematologic malignancies, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemias, myelomas, lymphomas, hepatoma, adenomas, sarcomas, carcinomas, blastomas, etc. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

The term "culturing" refers to the in vitro maintenance, differentiation, and/or propagation of cells or in suitable media. By "enriched" is meant a composition comprising cells present in a greater percentage of total cells than is found in the tissues where they are present in an organism. For example, the enriched cultures and preparations of $CD83^+$ $CCR7^-$ DCs and $CD83^+$ $CCR7^+$ DCs made by the methods of the invention are present in a higher percentage of total cells as compared to their percentage in the tissues where they are present in an organism (e.g., blood, skin, lymph nodes, etc.).

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 18th Ed. (Mack Publ. Co., Easton (1990)).

An "effective amount" is an amount sufficient to effect beneficial or desired results, such as enhanced immune response, treatment, prevention or amelioration of a medical condition (disease, infection, etc). An effective amount can be administered in one or more administrations, applications or dosages. Suitable dosages will vary depending on body weight, age, health, disease or condition to be treated and route of administration.

As used herein, "signaling" means contacting an immature or mature dendritic cell with an IFN-γ receptor agonist, a TNF-α receptor agonist, a CD40L polypeptide or other CD40 agonist. In one embodiment, such agonists are provided externally, (e.g., in the cell culture medium). In another embodiment, the polypeptide agonist is provided via transfection of an immature or mature dendritic cell with a nucleic acid encoding the polypeptide. Alternatively, a nucleic acid aptamer agonist could be provided in the medium or by transfection. In cases where the polypeptide (s) is provided by transfecting a dendritic cell with a nucleic acid encoding the polypeptide, signaling is effected upon translation of an mRNA encoding the polypeptide, rather than upon transfection with the nucleic acid. In one aspect, this invention provides methods for preparing enriched populations of mature dendritic cells (DCs) that induce potent immunostimulatory responses in vivo and/or in vitro. As used herein, the term "mature dendritic cells" means dendritic cells that demonstrate elevated cell surface expression of co-stimulator molecule CD83, compared to immature DCs (iDCs). Mature DCs of the invention include both $CD83^+$ $CCR7^-$ DCs and $CD83^+$ $CCR7^+$ DCs. The second signal, a CD40 agonist, can be given to either immature $CD83^-$ $CCR7^-$ DCs, or to $CD83^+$ $CCR7^-$ mature DCs.

The literature (Schaft 2005, Bonehill 2004) suggests that post maturation electroporation of DCs with antigen-encoding RNA resulted in DCs with greater potency to invoke immune responses. Therefore, methods were developed to alter the 'CD40L base process' (sequential IFN-γ signaling and CD40L signaling of $CD83^-$ iDCs), by altering the timing of the CD40L signaling to $CD83^+$ $CCR7^-$ mature DCs (post phenotypic maturation). In this embodiment, DCs were first phenotypically matured by adding 'inflammatory mediators', IFN-γ and TNF-α, and optionally $PGE_2$, to the culture medium, and then electroporating with CD40L mRNA, and optionally antigen-encoding mRNA approximately 12-30 hours (preferably about 18 hrs) later. This novel process was named 'PME-CD40L', for Post Maturation Electroporation with CD40L to produce $CD83^+$ $CCR7^+$ mature DCs. Cells harvested 4 hrs post electroporation and formulated as a vaccine were shown to mediate maximum immunopotency in in vitro assays (see examples). As yet a further enhancement, DCs can be pulsed with an activation ligand for NKT-cells, namely α-galactosylceramide, so as to recruit this population of effector cells to the immune response. NKT-cells display facets of both T-helper and T-cytotoxic cells: NKT-cells can secrete IFN-γ, display CD40L, and can secrete granzyme B, the latter to induce apoptosis in target cells. Thus, NKT-cell recruitment can lead to enhanced DC function by virtue of additional NKT-cell CD40L/DC-CD40 interactions, or amplify cell mediated immune responses by secreting helper cytokines, and/or contributing to a direct lytic effect on target cells.

After sequential signaling with the first signal (an IFN-γ receptor agonist and/or a TNF-α receptor agonist) to iDCs, and the second signal (a CD40 agonist) to either $CD83^-$ $CCR7^-$ iDCs, or to $CD83^+$ $CCR7^-$ mature DCs, the resulting DCs demonstrate (i) elevated cell surface expression of co-stimulator molecules CD80, CD83, and CD86, ii) are $CCR7^+$, and iii) secrete IL-12 p70 polypeptide or protein, and/or secrete significantly reduced levels (0 to 500 pg/per million DCs) of IL-10. In preferred embodiments, the mature $CD83^+$ $CCR7^+$ DCs of the invention produce at least 1000 pg IL-12/$10^6$ DCs, preferably at least 2000, 3000, 4000, 5000, or 6000 pg IL-12/$10^6$ DCs, more preferably at least 7000, 8000, 9000 or 10,000 pg IL-12/$10^6$ DCs, and most preferably at least 12,000, 15,000, 17,000 or 20,000 pg IL-12/$10^6$ DCs. IL-10 and IL-12 levels can be determined by ELISA of culture supernatants collected at up to 36 hrs post induction of DC maturation from immature DCs. Wierda et al. (2000) Blood 96:2917. Ajdary et al. (2000) Infection and Immunity 68:1760.

Immature DCs can be isolated or prepared from a suitable tissue source containing DC precursor cells and differentiated in vitro to produce immature DC. For example, a suitable tissue source can be one or more of bone marrow cells, peripheral blood progenitor cells (PBPCs), peripheral blood stem cells (PBSCs), and cord blood cells. Preferably, the tissue source is a peripheral blood mononuclear cell (PBMC). The tissue source can be fresh or frozen. In another aspect, the cells or tissue source are pre-treated with an effective amount of a growth factor that promotes growth and differentiation of non-stem or progenitor cells, which are then more easily separated from the cells of interest. These methods are known in the art and described briefly in Romani, et al. (1994) Exp. Med. 180:83 and Caux, C. et al. (1996) Exp. Med. 184:695. In one aspect, the immature DCS are isolated from peripheral blood mononuclear cells (PB-MCs). In a preferred embodiment, the PBMCs are treated with an effective amount of granulocyte macrophage colony stimulating factor (GM-CSF) in the presence or absence of interleukin 4 (IL-4) and/or IL-13, so that the PBMCs differentiate into immature DCs. Most preferably, PBMCs are cultured in the presence of GM-CSF and IL-4 for about 4-7 days, preferably about 5-6 days, to produce immature DCs. In preferred embodiments, the first signal is given at day 4, 5, 6, or 7, and most preferably at day 5 or 6. In addition, GM-CSF as well as IL-4 and/or IL-13 may be present in the medium at the time of the first and/or second signaling.

To increase the number of dendritic precursor cells in animals, including humans, one can pre-treat subjects with substances which stimulate hematopoiesis. Such substances include, but are not limited to G-CSF, and GM-CSF. The amount of hematopoietic factor to be administered may be determined by one skilled in the art by monitoring the cell differential of individuals to whom the factor is being administered. Typically, dosages of factors such as G-CSF and GM-CSF will be similar to the dosage used to treat individuals recovering from treatment with cytotoxic agents. As an example, GM-CSF or G-CSF can be administered for 4 to 7 days at standard doses prior to removal of source tissue to increase the proportion of dendritic cell precursors. U.S. Pat. No. 6,475,483 teaches that dosages of G-CSF of 300 micrograms daily for 5 to 13 days and dosages of GM-CSF of 400 micrograms daily for 4 to 19 days result in significant yields of dendritic cells.

The methods of the invention produce an enriched population of mature CD83$^+$ CCR7$^+$ dendritic cells that are potent immunostimulatory agents. Specifically, the invention provides a method for preparing mature dendritic cells (DCs), comprising the sequential steps of: (a) signaling isolated immature dendritic cells (iDCs) with a first signal comprising an interferon gamma receptor (IFN-γR) agonist, and optionally a TNF-αR agonist, to produce IFN-γR agonist signaled dendritic cells; and (b) signaling said IFN-γR agonist signaled dendritic cells with a second transient signal comprising an effective amount of a CD40 agonist to produce CCR7$^+$ mature dendritic cells. The invention further provides CD83$^+$ CCR7$^-$ mature DCs and CD83$^+$ CCR7$^+$ mature DCs. In preferred embodiments, the CD83$^+$ CCR7$^+$ mature DCs and/or the CD83$^+$ CCR7$^-$ mature DCs of the invention transiently express CD40L polypeptide. Preferrably, CD40L is predominantly localized intracellularly, rather than on the cell surface. Most preferably, at least 60%, at least 70%, at least 80% or at least 90% of CD40L polypeptide is localized intracellularly.

In an alternative embodiment, the immature dendritic cells are signaled with an effective amount of a TNF-α receptor agonist followed by signaling with a CD40 agonist. Thus, the invention provides a method for preparing mature dendritic cells (DCs), comprising sequentially signaling isolated immature dendritic cells with a first signal comprising a tumor necrosis factor alpha receptor (TNF-αR) agonist followed by a second signal comprising a CD40 agonist, wherein said signaling is in the absence of an effective amount of IL-1β and/or IL-6.

For either embodiment (IFN-γR agonist or TNF-αR agonist as a first signal), the second CD40 agonist signal can be given to either CD83$^-$ CCR7$^-$ iDCs, or to CD83$^+$ CCR7$^-$ mature DCs. In a preferred embodiment, the immature DCs and/or mature DCs are contacted with PGE$_2$. Preferably the cells are contacted with PGE$_2$ at about the same time that they receive the first signal (an IFN-γR agonist or TNF-αR agonist). In preferred embodiments, GM-CSF and at least one of IL-4 or IL-13 is present in the medium at the time the dendritic cells receive the first and second signals. In further embodiments, the method further comprises contacting the immature dendritic cells, signaled dendritic cells, and/or CCR7$^+$ dendritic cells with a NKT cell ligand that can activate CD1d-restricted NKT cells and consequently potentiate innate and adoptive immunity. In preferred embodiments, the NKT cell ligand is a compound selected from the group consisting of: α-galactosylceramides, α-glucosylceramides, α-6-deoxygalactosylceramides, α-6-deoxygalactofuranosylceramides, β-6-deoxygalactofuranosylceramides, β-arabinosylceramides, α-C-galactosylceramides and α-S-galactosylceramides. A preferred compound is the α-galactosylceramide known as KRN7000 ((2S,3S,4R)-1-O-(alpha-D-galactopyranosyl)-2-(N-hexacosanoylamino)-1,3,4-octadecanetriol).

Agelasphins, disclosed in JP patent 3068910, are a class of compounds originally discovered in a marine sponge which have an α-galactosylceramide (α-GalCer) structure and immunostimulating and anti-tumor activity. KRN7000 is a potent synthetic analog of agelasphins, disclosed in U.S. Pat. No. 5,767,092, the contents of which is incorporated by reference. Additional useful analogs of agelasphins are disclosed U.S. Pat. No. 5,936,076, the contents of which is incorporated by reference. The structure of KRN7000 is shown below:

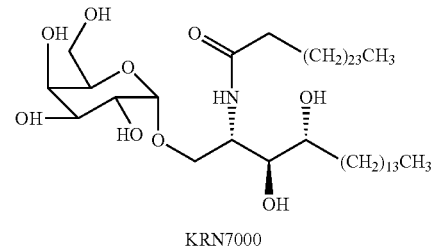

KRN7000

Glycosylceramide analogs of KRN7000 (e.g, α-galactosylceramides, α-glucosylceramides, α-6-deoxygalactosylceramides, α-6-deoxygalactofuranosylceramides, β-6-deoxygalactofuranosylceramides, β-arabinosylceramides) are disclosed in U.S. Pat. No. 5,849,716, the contents of which is incorporated by reference. U.S. Pat. No. 5,780,441, the contents of which is incorporated by reference, discloses oligosaccharide (di-, tri-, tetra-, penta-) derivatives of KRN7000. Methods for using KRN7000 and related analogs to produce KRN7000 antigen loaded DCs, and to activate human NKT cells are disclosed in U.S. Ser. No. 09/721,768 and U.S. Pat. No. 6,531,453, the contents of each are specifically incorporated by reference.

U.S. Pat. No. 5,936,076, the contents of which is incorporated by reference, discloses α-galactosylceramide compounds represented by the following formula:

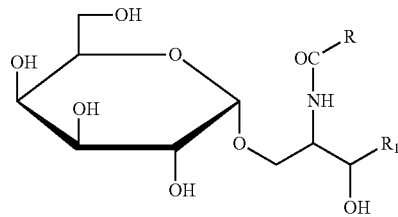

wherein the fatty acid chain, R represents:

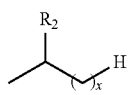

where $R_2$ represents H or OH and X denotes an integer of 0-26 or R represents —$(CH_2)_7CH=CH(CH_2)_7CH_3$ and $R_1$ represents any one of the substituents defined by the following (a)-(e)
 (a) —$CH_2(CH_2)_yCH_3$
 (b) —$CH(OH)(CH_2)_yCH_3$
 (c) —$CH(OH)(CH_2)_yCH(CH_3)_2$
 (d) —$CH=CH(CH_2)_yCH$
 (e) —$CH(OH)(CH_2)_yCH(CH_3)CH_2CH_3$
Wherein Y denotes an integer 5-17.

WO 03/105769, U.S. 2004/0127429, the contents of which are incorporated by reference, and Shimieg J. et al., (2003) J. Exp. Med. 198:1631-1641 disclose the structure of α-C-glycolipids, where the oxygen atom on glycoside bond of α-glycosylceramides such as α-galactosylceramide and α-glucosylceramides is replaced by carbon atom. The structure of a representative compound is shown below.

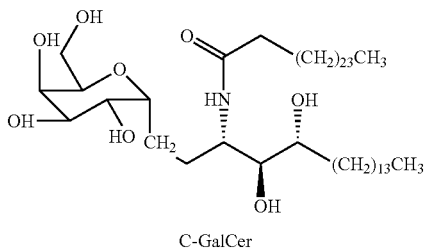

C-GalCer

WO 03/016326, the contents of which is incorporated, disclose KRN7000 analogs with truncated ceramide such as "C4" or "OCH" having the following structure:

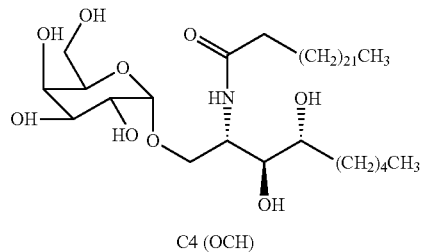

C4 (OCH)

U.S. Pat. No. 6,635,622, the contents of which is incorporated by reference, discloses α-C—, N, or S-Glycolipids, wherein the oxygen atom on glycoside bond of a galactosylceramide is replaced by —$(CH_2)_a$—$CH=CH$—$(CH_2)_{a'}$—, —$(CH_2)_a$—$S(O)_{0-2}$—$CH_2$—, or —$NHCH_2$—, wherein a and a' each denote an integer of 0-5 and a+a' is 5 or less.

In preferred embodiments, the IFN-γR agonist is IFNγ or a biologically active fragment thereof. Preferably, the IFNγ is a mammalian IFNγ, most preferably a human IFNγ. The cDNA and amino acid sequence of human IFNγ are shown in SEQ ID NOs: 5 and 6, respectively. Preferably, the IFNγ has the sequence shown in SEQ ID NO:6, or a fragment thereof. In one embodiment, the IFN-γR comprises a polypeptide having at least 80% sequence identity with SEQ ID NO:6. Preferably, the IFN-γR agonist has at least 85%, 90%, 95%, 97%, 98% or 99% sequence identity with SEQ ID NO:6. Methods for testing the activity of IFN-γR agonists are known to those of skill in the art, and some of these methods are described below. Immature DCs can be signaled by adding an IFN-γR agonist the culture medium, or by expressing the IFN-γR agonist in the dendritic cell. In one embodiment, the DC is transfected with an mRNA encoding an IFN-γR agonist, such as SEQ ID NO:6, or a biologically active fragment thereof. Signaling would then occur upon translation of the mRNA within the dendritic cell. Most preferably, the IFN-γR agonist is added to the culture medium containing immature DCs. In a preferred embodiment, the culture medium further comprises $PGE_2$ and/or GM-CSF plus IL-4 or IL-13.

The receptor for IFN-γ has two subunits: IFN-γR1, the ligand-binding chain (also known as the α chain) and IFN-γR2, the signal-transducing chain (also known as the β chain or accessory factor 1). These proteins are encoded by separate genes (IFNGR1 and IFNGR2, respectively) that are located on different chromosomes. As the ligand-binding (or α) chains interact with IFN-γ they dimerise and become associated with two signal-transducing (or β) chains. Receptor assembly leads to activation of the Janus kinases JAK1 and JAK2 and phosphorylation of a tyrosine residue on the intracellular domain of IFN-γR1. This leads to the recruitment and phosphorylation of STAT1 (for 'signal transducers and activators of transcription'), which forms homodimers and translocates to the nucleus to activate a wide range of IFN-γ-responsive genes. After signaling, the ligand-binding chains are internalized and dissociate. The chains are then recycled to the cell surface. Bach et al. (1997) Ann. Rev. Immunol. 15, 563-591; and Lammas, Casanova and Kumararatne (2000) Clin Exp Immunol 121, 417-425. The crystal structure of the complex of human IFN-γ with the soluble, glycosylated extracellular part of IFN-γRα (sIFN-γRα) has been determined at 2.9 Å resolution using multi-wavelength anomalous diffraction methods. Thiel et al. Structure 8:927-936 (2000).

In one assay, INF-γ receptor agonists, such as IFN-γ decrease $Na^+$—$K^+$-ATPase activity in a time- and concentration-dependent manner in human intestinal epithelial Caco-2 cells. $Na^+$—$K^+$-ATPase activity can be determined as the difference between total and ouabain-sensitive ATPase. Treatment with IFN-γ markedly increases the expression of total and phospho-STAT1, this being accompanied by activation of p38 MAPK. p38 MAP kinase activity can be analyzed by Western blotting using the p38 MAP kinase assay kit. Total and phosphorylated STAT1 protein levels were detected using the PhosphoPlus® Stati. The transduction mechanisms set into motion by IFN-γ involve the activation of PKC downstream STAT1 phosphorylation and Raf-1, MEK, ERK2 and p38 MAPK pathways. See Magro et al., Br J Pharmacol advance online publication, Jul. 26, 2004; doi:10.1038/sj.bjp.0705895, the contents of which is incorporated by reference.

For the purpose of illustration, signaling with IFN-γ receptor agonists, TNF-α receptor agonists and/or CD40 agonists can be provided by contacting a cell directly with IFN-γ polypeptides and/or proteins and/or TNF-α polypeptides or proteins and/or CD40 agonists, respectively. Alternatively, signaling of a cell with IFN-γR agonists, TNF-αR agonists or CD40 agonists can occur upon translation of mRNA encoding such polypeptides or proteins within the dendritic cell. Thus, signaling occurs upon expression of IFN-γR agonist, TNF-αR agonist and CD40 agonist polypeptides and/or proteins.

The second signal used in the methods of the invention is a transient signal with a CD40 agonist. Persistent expression of a CD40 agonist polypeptide, such as constitutive expression of CD40L from a lentiviral vector as described by Koya et al., supra, is not considered transient expression. The signal can be considered transient if the medium containing a CD40 agonist is removed from the DCs, or if the DCs are loaded with an mRNA encoding a CD40 agonist. The CD40 agonist signal can also be considered transient if the DCs are loaded/transfected with or with an expression vector encoding a CD40 agonist, provided that either: 1) the promoter driving CD40 agonist expression is not constitutive in DCs, or 2) the expression vector does not integrate into the DC genome or otherwise replicate in DCs.

In preferred embodiments, the CD40 agonist is a CD40L polypeptide or a CD40 agonistic antibody. In general, ligands that bind CD40 may act as a CD40 agonist. Applicants have demonstrated that administration of a second signal comprising CD40L to the cells by transfection of immature or mature DCs with CD40L mRNA produces subsequently modified DCs that induce immunostimulatory responses rather than immunosuppressive. In one embodiment, CD40L mRNA transfected dendritic cells are cultured in medium containing IFNγ (and preferentially $PGE_2$ as well) immediately after transfection and prior to translation of the CD40L mRNA to produce an effective amount of a CD40L signal. In this embodiment, although IFNγ is added after transfection with CD40L mRNA, the dendritic cells receive the IFNγ signal prior to the signal resulting upon translation of the CD40L mRNA. Thus, the order in which the agents are delivered to the cells is important only in that CD40L signaling must occur after IFN-γ signaling. As described in more detail below, the signaling of the DCs can occur in vivo or ex vivo, or alternatively one or more set may occur ex vivo and the remaining steps of the method can occur in vivo.

In one embodiment, the CD40 agonist is an aptamer that binds CD40. Similarly, IFN-γ and TNF-α could be replaced by aptamers, antibodies, and the like, that have a similar biological activity. Most preferably, the CD40 agonist is delivered as mRNA encoding CD40L.

As used herein, "CD40 Ligand" (CD40L) shall encompass any polypeptide or protein that specifically recognizes and activates the CD40 receptor and activates its biological activity. The term includes transmembrane and soluble forms of CD40L. In preferred embodiments, the CD40 agonist is a mammalian CD40L, preferably a human CD40L. Alignments of the human and mouse cDNAs and proteins are shown in FIGS. 16 and 17, respectively. A human CD40L cDNA and the corresponding amino acid sequence are shown in SEQ ID NOS:1 and 2, respectively. The open reading frame for CD40L is represented by nucleotides 40 to 822 of SEQ ID NO.1, while the TGA stop codon in at position 823 to 825. Also useful in the methods of the invention are truncated CD40L (residues 47 to 261 of SEQ ID NO:2, encoded by nucleotide residues 178 to 825 of SEQ ID NO:1) and CD40L fragments encoded by nucleotides 43 to 825 of SEQ ID NO:1, 181 to 825 of SEQ ID NO:1, 193 to 825 of SEQ ID NO:1, 376 to 825 of SEQ ID NO:1, 379 to 825 of SEQ ID NO:1 and 400 to 825 of SEQ ID NO:1. In preferred embodiments, the CD40L polypeptide is selected from the group consisting of: a) a polypeptide comprising SEQ ID NO:2; b) a polypeptide comprising amino acid residues 47 through 261 of SEQ ID NO:2; c) a polypeptide comprising amino acid residues 51 through 261 of SEQ ID NO:2; d) a polypeptide comprising amino acid residues 120 through 261 of SEQ ID NO:2; e) a polypeptide comprising amino acid residues 113 through 261 of SEQ ID NO:2; f) a polypeptide comprising amino acid residues 112 through 261 of SEQ ID NO:2; g) a polypeptide comprising SEQ ID NO:10; h) a polypeptide comprising amino acid residues 35 through 261 of SEQ ID NO:2; i) a polypeptide comprising amino acid residues 34 through 225 of SEQ ID NO:2; j) a polypeptide comprising amino acid residues 113 through 225 of SEQ ID NO:2; k) a polypeptide comprising amino acid residues 120 through 225 of SEQ ID NO:2; and l) a fragment of the polypeptide of any of (a) through (k), wherein said fragment binds CD40.

Preferably, the CD40L polypeptide is encoded by an mRNA comprising a polynucleotide selected from the group consisting of: a) a polynucleotide of SEQ ID NO:1; b) a polynucleotide comprising nucleotides 40 to 822 of SEQ ID NO:1; c) a polynucleotide comprising nucleotides 178 to 822 of SEQ ID NO:1; d) a polynucleotide comprising nucleotides 190 to 822 of SEQ ID NO:1; e) a polynucleotide comprising nucleotides 397 to 822 of SEQ ID NO:1; f) a polynucleotide comprising nucleotides 376 to 822 of SEQ ID NO:1; g) a polynucleotide of SEQ ID NO:9; h) a polynucleotide of SEQ ID NO:13; i) a polynucleotide having at least 80% sequence identity with any polynucleotide of (a) through (h); j) a polynucleotide hybridizing under stringent conditions to any polynucleotide of (a) through (h); and k) a polynucleotide of (a) through (j), further comprising a 3' untranslated sequence selected from the group consisting of the nucleic acids of SEQ ID NO:14, 15, 16, 17 or 18, and/or a 5' untranslated sequence selected from the group consisting of the nucleic acids of SEQ ID NO:19, 20, 21, 22, or 23.

Alternatively, the CD40L polypeptide is a polypeptide having at least 77% sequence identity to a polypeptide selected from the group consisting of: a) a polypeptide comprising SEQ ID NO:2; b) a polypeptide comprising amino acid residues 47 through 261 of SEQ ID NO:2; c) a polypeptide comprising amino acid residues 51 through 261 of SEQ ID NO:2; d) a polypeptide comprising amino acid residues 120 through 261 of SEQ ID NO:2; e) a polypeptide comprising amino acid residues 113 through 261 of SEQ ID NO:2; f) a polypeptide comprising amino acid residues 112 through 261 of SEQ ID NO:2; g) a polypeptide comprising SEQ ID NO:10; h) a polypeptide comprising amino acid residues 35 through 261 of SEQ ID NO:2; i) a polypeptide comprising amino acid residues 34 through 225 of SEQ ID NO:2; j) a polypeptide comprising amino acid residues 113 through 225 of SEQ ID NO:2; k) a polypeptide comprising amino acid residues 120 through 225 of SEQ ID NO:2; and l) a fragment of the polypeptide of any of (a) through (k), wherein said fragment binds CD40.

CD40 was first characterized as a receptor expressed on B lymphocytes. Schonbeck and Libby (2001) Cell Mol. Life Sci. 58:4. It was later discovered that engagement of B-cell CD40 with CD40L expressed on activated T-cells is essential for T-cell dependent B-cell activation (i.e. proliferation, immunoglobulin secretion, and class switching). It was subsequently revealed that functional CD40 is expressed on a variety of cell types other than B-cells, including hematopoietic progenitor cells, T lymphocytes, basophils, eosinophils, monocytes/macrophages, dendritic cells, epithelial cells, endothelial cells, smooth muscle cells, keratinocytes, fibroblasts and carcinomas. Schonbeck and Libby (2001) supra.

The CD40 Ligand was cloned in 1993 and reported by Gauchat, et al. (1993) FEBS Lett. 315:259. Graf et al. mapped it to chromosome Xq26.3-q27.1 (Graf, et al. (992) Eur. J. Immunol. 22: 3191-3194). Shorter soluble forms of the cell-associated full-length 39 kDa form of CD40 Ligand have been described with molecular weights of 33, and 18 kDa. Graf, et al. (1995) Eur. J. Immunol. 25: 1749; Ludewig, et al. (1996) Eur. J. Immunol. 26: 3137; Wykes, et al. (1998) Eur. J. Immunol. 28:548. The 18 kDa soluble form generated via intracellular proteolytic cleavage, which lacks the cytoplasmic tail, the transmembrane region and parts of the extracellular domain, but conserves the CD40 binding domain retains the ability to bind to CD40 receptor and therefore is an example of a CD40 receptor signaling agent. Graf, et al. (1995) supra.

U.S. Pat. No. 5,981,724 discloses DNA sequences encoding human CD40 Ligand (CD40L) as well as vectors, and transformed host cells for the purpose of producing CD40L polypeptides. U.S. Pat. No. 5,962,406 discloses DNA sequences encoding soluble forms of human CD40L.

Exemplary sequences of mammalian homologs to CD40L have the following Genbank accession numbers: NM_204733 (*Gallus gallus* (chicken)); DQ054533 (*Ovis aries* (sheep)); Z48469 (*Bos taurus* (cow)); AY333790 (*Canis familiaris* (dog)); Macaca nemestrina (pig-tailed macaque)); AF344844 (*Callithrix jacchus* (white-tufted-ear marmoset)); AF34481 (*Cercicebus torquatus atys* (sooty mangabey)); AF344860 (*Aotus trivirgatus* (douroucouli)); AF344859 *Macaca mulatta* (rhesus monkey)); AF116582 (*Rattus nevegicus* (Norway rat)); and AF079105 (*Felus catus* (cat)).

The CD40 receptor can also be activated by use of CD40 agonist antibodies, antibody fragments, derivatives and variants thereof. CD40 agonist antibodies can be purchased from commercial vendors such as Mabtech (Nacka, Sweden). Examples and methods to generate these agents are also provided infra. The literature also provides examples of CD40 agonist antibodies and antibody fragments. See, e.g., Osada, et al. (2002) 25(2):176 and Ledbetter, J. A. et al. (1997) Crit. Reviews in Immunol. 17:427.

As noted above, the agent having the biological activity of CD40L can be a polypeptided from an exogenous polynucleotide (mRNA or DNA) encoding CD40L. For example, the CD40L mRNA has the sequence of SEQ ID NO.: 1 or SEQ ID NO:3. Alternatively, the cells are signaled with an effective amount of CD40L protein and/or polypeptide, for example, those having the sequence of SEQ ID NO.: 2 or SEQ ID NO:4. Modified CD40L can also be used in the methods of this invention. For example, CD40L includes those molecules that have been altered through addition, subtraction, or substitution, either conservatively or non-conservatively, of any number of amino acids, provided that the resulting protein binds CD40 on the surface of DC. A "conservative alteration" is one that results in an alternative amino acid of similar charge density, hydrophilicity or hydrophobicity, size, and/or configuration (e.g., Val for Ile). In comparison, a "nonconservative alteration" is one that results in an alternative amino acid of differing charge density, hydrophilicity or hydrophobicity, size and/or configuration (e.g., Val for Phe). The means of making such modifications are well-known in the art and also can be accomplished by means of commercially available kits and vectors (for example, those available from New England Biolabs, Inc., Beverly, Mass.; Clontech, Palo Alto, Calif.).

When the agents are delivered as polynucleotides or genes encoding the agents, an effective amount of the polynucleotide can be replicated by any method known in the art. PCR technology is one means to replicate DNA and is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) and references cited therein. Additional methods to generate polynucleotides are provided infra.

In embodiments of the invention, wherein immature dendritic cells are stimulated with an agonist of TNF-α receptor, followed by stimulation with a CD40 agonist, the method is performed in the absence of an effective amount of interleukin 1-beta (IL-1β) and or interleukin 6 (IL-6). Methods for detecting the presence of proteins such as IL-1β and IL-6 are known in the art.

One of skill in the art can determine when the object of the method has been met by sampling a cell or small population of DCs from the population for the presence of mature DCs expressing CD40L mRNA and/or CD40L polypeptide. In a further aspect, the mature $CD83^+$ $CCR7^+$ DCs of the invention express interleukin 12 (IL-12) p35 protein. In a further aspect, mature $CD83^+$ $CCR7^+$ DCs express IL-12 p70 protein, and/or express limited IL-10 (not more than 500 pg/ml/$10^6$ DCs).

The steps of the method can be practiced in vivo or ex vivo. When practiced ex vivo, the method can be practiced in an open or closed system. Methods and systems for culturing and enriching cell populations are known in the art. See, examples 1 and 2 of U.S. Patent Publication No. 2004/0072347. See also U.S. Patent Publication No. 2003/0235908, which describes closed systems for cell expansion.

In a further aspect, of this invention, the above method is modified by the addition of delivering to the immature or mature DCs an effective amount of an antigen which will be then be processed and presented by the mature DCs. Thus, the methods of the invention further comprise introducing into iDCs, signaled DCs or $CCR7^+$ mature DCs one or more antigens or a polynucleotide(s) encoding one or more antigens to produce an antigen-loaded $CCR7^+$ mature DCs. The antigen or antigen-encoding polynucleotide can be introduced prior to said first signal. Alternatively, the antigen or antigen-encoding polynucleotide is delivered subsequent to said first signal and prior to said second signal. In another embodiment, the antigen or polynucleotide is delivered subsequent to said second signal or substantially concurrent with said second signal.

For example, antigens include, but are not limited to, pathogens, pathogen lysates, pathogen extracts, pathogen polypeptides, viral particles, bacteria, proteins, polypeptides, cancer cells, cancer cell lysates, cancer cell extracts, cancer cell specific polypeptides. Antigens can be naturally occurring or recombinantly produced. The immunogens can be delivered to the cells as polypeptides, proteins or as nucleic acids using methods known in the art which are briefly described infra. Preferably, one or more polynucleotides encoding one or more antigens are introduced into the iDCs, signaled DCs or $CCR7^+$ mature DCs. The polynucleotide can be introduced into the DCs by methods known to those of skill in the art. In a preferred embodiment, the polynucleotide is introduced by electroporation. Most preferably, the polynucleotide is an mRNA. In preferred embodiments, the antigen or antigen encoding mRNA is introduced together with an mRNA encoding a CD40 agonist or substantially concurrent with CD40 agonist signaling.

The methods can be further modified by contacting the cell with an effective amount of a cytokine or co-stimulatory molecule, e.g., GM-CSF, IL-4 and $PGE_2$. In embodiments where the immature DCs are signaled with a TNFαR agonist followed by signaling with CD40 agonist, effective amounts of IL-1β and/or IL-6 are specifically excluded from the culture.

The antigen may be delivered in its "natural" form in that no human intervention was involved in preparing the antigen or inducing it to enter the environment in which it encounters the APC. Alternatively or additionally, the antigen may comprise a crude preparation, for example of the type that is commonly administered in a conventional allergy shot or in a tumor lysate. The antigen may alternatively be substantially purified, e.g., at least about 90% pure.

Where the antigen is a peptide, it may be generated, for example, by proteolytic cleavage of isolated proteins. Any of a variety of cleavage agents may be utilized including, but not limited to, pepsin, cyanogen bromide, trypsin, chymotrypsin, etc. Alternatively, peptides may be chemically synthesized, preferably on an automated synthesizer such as is available in the art. Also, recombinant techniques may be employed to create a nucleic acid encoding the peptide of interest, and to express that peptide under desired conditions.

The antigen can alternatively have a structure that is distinct from any naturally-occurring compound. In certain embodiments of the invention, the antigen is a "modified antigen" in that the antigen has a structure that is substantially identical to that of a naturally-occurring antigen but that includes one or more deviations from the precise structure of the naturally-occurring compound. For instance, where the naturally-occurring antigen is a protein or polypeptide antigen, a modified antigen as compared with that protein or polypeptide antigen would have an amino acid sequence that differs from that of the naturally-occurring antigen in the addition, substitution, or deletion of one or more amino acids, and/or would include one or more amino acids that differ from the corresponding amino acid in the naturally-occurring antigen by the addition, substitution, or deletion of one or more chemical moieties covalently linked to the amino acid. In one aspect, the naturally-occurring and modified antigens share at least one region of at least 5 amino acids that are at least approximately 75% identical. Those of ordinary skill in the art will appreciate that, in comparing two amino acid sequences to determine the extent of their identity, the spacing between stretches (i.e., regions of at least two) of identical amino acids need not always be precisely preserved. Naturally-occurring and modified protein or polypeptide antigens can show at least approximately 80% identity, more alternatively 85%, 90%, 95%, or greater than 99% identity in amino acid sequence for at least one region of at least 5 amino acids. Often, it may be useful for a much longer region (e.g., 10, 20, 50, or 100 or more amino acids) of amino acid sequence to show the designated degree of identity.

In preferred embodiments, the antigen is delivered as a polynucleotide or gene encoding the antigen, so that expression of the gene results in antigen production either in the individual being treated (when delivered in vivo) or the cell culture system (when delivered in vitro). Techniques for generating nucleic acids including an expressible gene, and for introducing such nucleic acids into an expression system in which any protein encoded by the expressible gene will be produced are known in the art and briefly described infra. Preferably, an mRNA encoding the antigen is introduced into the DC.

In one embodiment, the immunogen is delivered prior to said first signal, wherein the first signal is an IFNγR agonist or TNF-αR. Alternatively, the immunogen is delivered subsequent to said first signal and prior to said second signal, or the immunogen is delivered subsequent to said second signal. In another embodiment, the immunogen is delivered substantially concurrent with said second signal.

The amount of antigen to be employed in any particular composition or application will depend on the nature of the particular antigen and of the application for which it is being used, as will readily be appreciated by those of skill in the art.

The antigen-loaded dendritic cells are useful for raising an immune response to the antigen(s). Thus, in one aspect, the invention provides a method of raising an immune response in a subject comprising administering to the subject an effective amount of the immunogen loaded CCR7$^+$ mature DCs. The loaded DCs may be allogeneic or autologous to the subject.

The invention further provides a method of stimulating immune effector cells, comprising culturing said cells in the presence of an antigen loaded CCR7$^+$ mature DCs produced by the methods of invention to produce stimulated immune effector cells. In another embodiment, the invention provides a method of enhancing immunity in a subject comprising administering to the subject an effective amount of such stimulated immune effector cells.

In a further aspect of this invention, an effective amount of a cytokine and/or co-stimulatory molecule is delivered to the cells or patient, in vitro or in vivo. These agents can be delivered as polypeptides, proteins or alternatively, as the polynucleotides or genes encoding them. Cytokines, co-stimulatory molecules and chemokines can be provided as impure preparations (e.g., isolates of cells expressing a cytokine gene, either endogenous or exogenous to the cell) or in a "purified" form. Purified preparations are preferably at least about 90% pure, or alternatively, at least about 95% pure, or yet further, at least about 99% pure. Alternatively, genes encoding the cytokines or inducing agents may be provided, so that gene expression results in cytokine or inducing agent production either in the individual being treated or in another expression system (e.g., an in vitro transcription/translation system or a host cell) from which expressed cytokine or inducing agent can be obtained for administration to the individual.

Where both cytokine and antigen are to be delivered to an individual, they may be provided together or separately. When they are delivered as polypeptides or proteins, they can be delivered in a common encapsulation device or by means of physical association such as covalent linkage, hydrogen bonding, hydrophobic interaction, van der Waals interaction, etc. In an alternative embodiment, the compounds are provided together, genes encoding both are provided. For example, genes for both may be provided as part of the same nucleic acid molecule. In some embodiments, this nucleic acid molecule may be prepared so that both factors are expressed from a single contiguous polynucleotide, as a fusion protein in which the cytokine and the antigen are covalently linked to one another via a peptide bond. Alternatively or additionally, the genes may be linked to the same or equivalent control sequences, so that both genes become expressed within the individual in response to the same stimuli. A wide variety of different control sequences, active in different host cells under different conditions are known in the art. These control sequences, including constitutive control sequences, inducible control sequences, and repressible control sequences, can be used in accordance with the present invention, though inducible or repressible sequences are particularly preferred for applications in which additional control over the timing of gene expression is desired.

It is appreciated by those of skill in the art that administration of cytokine and/or antigen may optionally be combined with the administration of any other desired immune system modulatory factor such as, for example, an adjuvant or other immunomodulatory compound.

Antigens can also be delivered in the form of polynucleotides or genes encoding the antigens. The antigens can also be modified by linking a portion of sequence from a first polypeptide (e.g., a first antigen) to a portion of sequence from a second polypeptide (e.g., a second antigen, a signal sequence, a transmembrane domain, a purification handle, etc.) by means of a peptide bond. Those of ordinary skill in the art will appreciate the diversity of such fusion proteins for use in accordance with the present invention. Recombinant techniques further allow for the ready modification of the amino acid sequence of polypeptide or protein antigens, by substitution, deletion, addition, or inversion of amino acid sequences.

Where the immunogen is a fragment of an antigen, it may be generated, for example, by proteolytic cleavage of isolated proteins. Any of a variety of cleavage agents may be utilized including, but not limited to, pepsin, cyanogen bromide, trypsin, chymotrypsin, etc. Alternatively, peptides may be chemically synthesized, preferably on an automated synthesizer such as is available in the art (see, for example, Stewart et al., Solid Phase Peptide Synthesis, 2d. Ed., Pierce Chemical Co., 1984. Also, recombinant techniques may be employed to create a nucleic acid encoding the peptide of interest, and to express that peptide under desired conditions (e.g., in a host cell or an in vitro expression system from which it can readily be purified).

In preferred embodiments, the antigen is from a cancer cell or a pathogen. Preferably, the neoplastic cell is a renal cancer cell, a multiple myeloma cell or a melanoma cell. Preferred pathogens are HIV and HCV. In preferred embodiments, the antigen is delivered to the antigen presenting cell in the form of RNA isolated or derived from a neoplastic cell or a pathogen. Methods for RT-PCR of RNA extracted from any cell (e.g., a neoplastic cell or pathogen cell), and in vitro transcription are disclosed in copending PCT/US05/32710 and U.S. provisional patent application No. 60/525,076, the contents of which are incorporated by reference.

The antigen employed in accordance with the present invention may be a naturally-occurring compound or may alternatively have a structure that is distinct from any naturally-occurring compound. In certain embodiments of the invention, the antigen is a "modified antigen" in that the antigen has a structure that is substantially identical to that of a naturally-occurring antigen but that includes one or more deviations from the precise structure of the naturally-occurring compound.

Also provided by this invention are the enriched populations of mature DCs prepared by any of the methods described herein. Mature DCs prepared by the methods of the invention have enhanced immunostimulatory characteristics. In another aspect, the invention provides a method for storing an enriched population of mature DCs, comprising contacting an enriched dendritic cell population of the invention with a suitable cryopreservative under suitable conditions.

The compositions described herein are useful to raise an immune response in a subject by administering to the subject an effective amount of the enriched population of cells, e.g., DCs, modified DCs, or educated immune effector cells. The cells can be allogeneic or autologous. They can be administered to a subject to raise or induce an immune response in a subject comprising administering to the subject an effective amount of the enriched populations as described above. The cells can be allogeneic or autologous to the subject. They can also be used to educate immune effector cells such as T cells by culturing the immune effector cell in the presence and at the expense of a mature DC of this invention. The educated effector cells can also be used to enhance immunity in a subject by delivering to the subject an effective amount of these cells.

Methods for Generating and Delivering Polynucleotides

Certain embodiments of this invention require the use of polynucleotides. These can be generated and replicated using any method known in the art, e.g., one of skill in the art can use the sequences provided herein and a commercial DNA synthesizer to replicate the DNA. Alternatively, they can be obtained by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

In one embodiment, the agent (e.g., CD40L) is delivered as mRNA. RNA can be obtained by first inserting a DNA polynucleotide into a suitable host cell or preferably, by in vitro transcription. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook et al. (1989) supra. For instance, mRNA can be isolated using various lytic enzymes or chemical solutions according to the procedures set forth in Sambrook, et al. (1989) supra or extracted by nucleic-acid-binding resins following the accompanying instructions provided by manufactures.

In preferred embodiments the CD40L expression cassette contains a promoter suitable for in vitro transcription, such as the T7 promoter or SP6 promoter. Preferably, the in vitro transcribed CD40L or CD40 agonist mRNA is optimized for stability and efficiency of translation. For example, SEQ ID NO:13 represents an optimized CD40L mRNA, wherein ATG codons in the 5' untranslated region have been altered to avoid incorrect initiation of translation.

mRNA stability and/or translational efficiency can also be increased by including 3'UTRs and or 5'UTRs in the mRNA. Preferred examples of 3'UTRs include those from human CD40, β-actin and rotavirus gene 6. Preferred examples of 5'UTRs include CD40L, and the translational enhancers in the 5'UTRs of Hsp70, VEGF, spleen necrosis virus RU5, and tobacco etch virus.

For example, CD40L expression is normally regulated in part by 3'UTR-mediated mRNA instability, and therefore a large portion of the CD40L 3'UTR is not included in the current CD40L mRNA. CD40L is not normally expressed in DCs. In contrast, the CD40 Receptor is expressed in DCs and there is no evidence in the literature to indicate that its expression is regulated post-transcriptionally, particularly at the level of mRNA stability. Including the CD40 Receptor 3'UTR (SEQ ID NO:14, or an active fragment thereof) at the 3' end or region of the CD40L mRNA would give the RNA 3' untranslated sequence similar to naturally occurring CD40 messages without imparting any unwanted regulatory activity.

Beta-Actin is an abundantly expressed gene in human non-muscle cells. The human beta-actin promoter has been widely used to drive gene expression in mammalian cell lines and transgenic mice. Inclusion of the beta-actin 3'UTR plus flanking region has been demonstrated to further increase the level of mRNA accumulation from gene expression constructs containing the beta-actin promoter.

Qin and Gunning (1997) Journal of Biochemical and Biophysical Methods 36 pp. 63-72. SEQ ID NO:15 represents the untranslated region of the final exon of the human beta-actin 3' UTR. SEQ ID NO:16 shows the minimal region of this 3'UTR.

The 3'UTR of the simian rotavirus gene 6 (SEQ ID NO:17) mRNA functions as an enhancer of translation in its capped, non-polyadenylated viral transcript. The 3'UTR has also been shown to enhance translation of a heterologous reporter mRNA in Rabbit reticulocyte lysates. Yang et. al., 2004 Archives of Virology 149:303-321. The minimal functional element of this 3'UTR is shown in SEQ ID NO:18

The 5' UTR of the human hsp70 gene (SEQ ID NO:19) has been shown to increase translation of reporter mRNAs in the absence of stress induction and without dramatically influencing the message stability. Enhancer function has been demonstrated in a number of human cell lines. Vivinus, et al., 2001 European Journal of Biochemistry 268:1908-1917.

The mouse VEGF 5' UTR (SEQ ID NO:20) enhances translation of a monocistronic reporter RNA and also has IRES (Internal Ribosome Entry Site) activity. Its enhancer activity has been demonstrated in rat, hamster and human cell lines. The full length 5'UTR is 1014 nucleotides, but a 163 nucleotide mutant version (SEQ ID NO:21) was shown to be more active. Stein et al., 1998 Molecular and Cellular Biology 18:3112-3119.

The Spleen Necrosis Virus (SNV) is an avian retrovirus. The RU5 region of the viral 5' LTR (SEQ ID NO:22) stimulates translation efficiency of a non-viral reporter RNA in human 293 cells. Roberts and Boris-Lawrie 2000 Journal of Virology 74:8111-8118.

The 143 nucleotide 5' leader of the tobacco etch virus RNA (SEQ ID NO:23) promotes cap-independent translation of reporter mRNAs in plant and animal cell lines. Although the leader sequence does not further enhance the translation of capped transcripts, the cap-independent CD40L expression in dendritic cells is a very attractive alternative to in vitro capping. Gallie et al. (1995) Gene 165:233-238. Niepel and Gallie (1999) Journal of Virology 73:9080-9088. Gallie, Journal of Virology (2001) 75:12141-12152.

Dendritic cells can be transfected with nucleic acids by methods known in the art, which include, but are not limited to calcium phosphate precipitation, microinjection or electroporation. They can be added alone or in combination with a suitable carrier, e.g., a pharmaceutically acceptable carrier such as phosphate buffered saline. Alternatively or additionally, the nucleic acid can be incorporated into an expression or insertion vector for incorporation into the cells. Vectors that contain both a promoter and a cloning site into which a polynucleotide can be operatively linked are known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, adenovirus, adeno-associated virus, cosmid, plasmid, fungal vectors and other recombination vehicles typically used in the art which have been described for expression in a variety of eukaryotic and prokaryotic hosts, and may be used for gene therapy as well as for simple protein expression.

Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens. Liposomes that also comprise a targeting antibody or fragment thereof can be used in the methods of this invention. This invention also provides the targeting complexes for use in the methods disclosed herein.

Polynucleotides are inserted into vector genomes using methods known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are known and available in the art.

Preparation and Isolation of Proteins and Polypeptides

Polypeptides and proteins are necessary components of various methods of this invention. The proteins and polypeptides can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Alternatively, the proteins and polypeptides can be obtained by known recombinant methods as described herein using the host cell and vector systems described below.

It is well know to those skilled in the art that modifications can be made to any peptide to provide it with altered properties. As used herein the term "amino acid" refers to either natural and/or unnatural or synthetic amino acids, including glycine and both the D and L optical isomers, and amino acid analogs and peptidomimetics. A peptide of three or more amino acids is commonly called an oligopeptide if the peptide chain is short. If the peptide chain is long, the peptide is commonly called a polypeptide or a protein. Peptides for use in this invention can be modified to include unnatural amino acids. Thus, the peptides may comprise D-amino acids, a combination of D- and L-amino acids, and various "designer" amino acids (e.g., β-methyl amino acids, C-α-methyl amino acids, and N-α-methyl amino acids, etc.) to convey special properties to peptides. Additionally, by assigning specific amino acids at specific coupling steps, peptides with α-helices β turns, β sheets, γ-turns, and cyclic peptides can be generated. In a further embodiment, subunits of peptides that confer useful chemical and structural properties will be chosen. For example, peptides comprising D-amino acids may be resistant to L-amino acid-specific proteases in vivo. Modified compounds with D-amino acids may be synthesized with the amino acids aligned in reverse order to produce the peptides of the invention as retro-inverso peptides. In addition, the present invention envisions preparing peptides that have better defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide peptides with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189-199 and Hruby et al. (1990) Biochem 3. 268:249-262); the present invention provides a method to produce a constrained peptide that incorporates random sequences at all other positions.

Methods for Isolating Stem Cells

Many methods are known in the art for the isolation and expansion of $CD34^+$ stem cells for in vitro expansion and differentiation into dendritic cells. See for example, U.S. Pat. No. 5,199,942, the contents of which is incorporated by reference. The following descriptions are for the purpose of illustration only and in no way are intended to limit the scope of the invention.

$CD34^+$ stem cells can be isolated from bone marrow cells or by panning the bone marrow cells or other sources with antibodies which bind unwanted cells, such as $CD4^+$ and $CD8^+$ (T cells), $CD45^+$ (panB cells) and GR-1 For a detailed description of this protocol see, Inaba, et al. (1992) 3. Exp. Med. 176:1693-1702. Human $CD34^+$ cells can be obtained from a variety of sources, including cord blood, bone marrow explants, and mobilized peripheral blood. Purification of $CD34^+$ cells can be accomplished by antibody affinity procedures. See, for example, Paczesny et al. (2004) 3 Exp Med. 199: 1503-11; Ho, et al. (1995) Stem Cells 13 (suppl. 3):100-105; Brenner (1993) Journal of Hematotherapy 2:7-17; and Yu, et al. (1995) PNAS 92:699-703.

Differentiating Stem Cells into Immature Dendritic Cells $CD34^+$ stem cells can be differentiated into dendritic cells by incubating the cells with the appropriate cytokines. Inaba et al. (1994) supra, described the in vitro differentiation of murine stem cells into dendritic cells by incubating the stem cells with murine GM-CSF. In brief, isolated stem cells are incubated with between 1 and 200 ng/ml murine GM-CSF, and preferably about 20 ng/ml GM-CSF in standard RPMI growth medium. The media is changed with fresh media about once every other day. After approximatedly 5-7 days in culture, a large percentage of cells are dendritic, as assessed by expression of surface markers and morphology. Dendritic cells are isolated by florescence activated cell sorting (FACS) or by other standard methods.

Murine $CD34^+$ stem cells can be differentiated into dendritic cells by culturing the cells with murine GM-CSF. Typically, the concentration of GM-CSF in culture is at least about 0.2 ng/ml, and preferably at least about 1 ng/ml. Often the range will be between about 20 ng/ml and 200 ng/ml. In many preferred embodiments, the dose will be about 100 ng/ml. IL-4 is optionally added in similar ranges for making murine DCs.

Human $CD34^+$ hematopoietic stem cells are preferably differentiated in vitro by culturing the cells with human GM-CSF and TNF-α. See for example, Szabolcs, et al. (1995) 154:5851-5861. Human GM-CSF is used in similar ranges, and TNF-α can also added to facilitate differentiation. TNF-α is also typically added in about the same ranges. Optionally, SCF or other proliferation ligand (e.g., Flt3) is added in similar dose ranges to differentiate human DCs.

As is apparent to those of skill in the art, dose ranges for differentiating stem cells and monocytes into dendritic cells are approximate. Different suppliers and different lots of cytokine from the same supplier vary in the activity of the cytokine. One of skill can easily titrate each cytokine which is used to determine the optimal dose for any particular cytokine.

Differentiation of Monocytes into Dendritic Cells

DCs can be generated from frequent, but non-proliferating $CD14^+$ precursors (monocytes) in peripheral blood by culture in medium containing GM-CSF and IL-4 or GM-CSF and IL-13 (see, e.g., WO 97/29182). This method is described in Sallusto and Lanzavecchia (1994) J. Exp. Med. 179:1109 and Romani et al. (1994) J. Exp. Med. 180:83. Briefly, $CD14^+$ precursors are abundant so that pretreatment of patients with cytokines such as G-CSF (used to increase $CD34^+$ cells and more committed precursors in peripheral blood) is reported to be unnecessary in most cases (Romani et al. (1996) J. Immunol. Methods 196:137). Others have reported that DCs generated by this approach appear rather homogenous and can be produced in an immature state or fully differentiated or mature. It was shown that it is possible to avoid non-human proteins such as FCS (fetal calf serum), and to obtain fully and irreversibly mature and stable DCs by using autologous monocyte conditioned medium as maturation stimulus (Romani et al. (1996) Immunol. Methods 196:137; Bender et al. (1996) J. Immunol. Methods 196: 121). However, in contrast to the instant invention, these studies did not result in mature DC having increased levels of IL-12 and/or decreased levels of IL-10.

Antigen Loading

Methods of loading dendritic cells with antigens are known to those of skill in the art. In one embodiment, the dendritic cells are cultured in medium containing the antigen. The DCs then take up and process the antigen on the cell surface in association with MHC molecules. Preferably, the DCs are loaded with antigen by transfection with a nucleic acid encoding the antigen. Methods of transfecting DCs are known to those of skill in the art.

Isolation of and Expansion of T Cells

In some methods of this invention, T cells are isolated from mammals so that they can be educated (or activated) by the mature, modified DC in vitro. In one method, Ficoll-Hypaque density gradient centrifugation is used to separate PBMC from red blood cells and neutrophils according to established procedures. Cells are washed with modified AIM-V (which consists of AIM-V (GIBCO) with 2 mM glutamine, 10 μg/ml gentamicin sulfate, 50 μg/ml streptomycin) supplemented with 1% fetal bovine serum (FBS). T cells are enriched by negative or positive selection with appropriate monoclonal antibodies coupled to columns or magnetic beads according to standard techniques. An aliquot of cells is analyzed for cell surface phenotype including CD4, CD8, CD3 and CD14. For the purpose of illustration only, cells are washed and resuspended at a concentration of about $5 \times 10^5$ cells per ml of AIM-V modified as above and containing 5% FBS and 100 U/ml recombinant IL-2 (rIL-2) (supplemented AIM-V). Where the cells are isolated from and HIV+ patient, 25 nM CD4-PE40 (a recombinant protein consisting of the HIV-1-binding CD4 domain linked to the translocation and ADP-ribosylation domains of *Pseudomonas aeruginosa* exotoxin A), or other similar recombinant cytotoxic molecule which selectively hybridizes to HIV is added to the cell cultures for the remainder of the cell expansion to selectively remove HIV infected cells from the culture. CD4-PE40 has been shown to inhibit p24 production in HIV-infected cell cultures and to selectively kill HIV-1-infected cells.

To stimulate proliferation, OKT3 monoclonal antibody (Ortho Diagnostics) can be added to a concentration of 10 ng/ml and the cells are plated in 24 well plates with 0.5 ml per well. The cells are cultured at a temperature of about 37° C. in a humidified incubator with 5% $CO_2$ for 48 hours. Media is aspirated from the cells and 1 ml of vector-containing supernatant (described below) supplemented with 5 µl/ml of protamine sulfate, 100 U/ml rIL-2, 100 U/ml penicillin, 0.25 µg/ml amphotericin B/ml and an additional 100 µg/ml streptomycin (25 nM CD4-PE40 can be added).

Cell Isolation and Characterization

In another aspect, cell surface markers can be used to isolate the cells necessary to practice the method of this invention. For example, human stem cells typically express CD34 antigen while DCs express MHC molecules and costimulatory molecules (e.g., B7-1 and B7-2), a lack of markers specific for granulocytes, NK cells, B cells, and T cells. The expression of surface markers facilitates identification and purification of these cells. These methods of identification and isolation include FACS, column chromatography, panning with magnetic beads, western blots, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like. For a review of immunological and immunoassay procedures in general, see Stites and Terr (eds.) 1991 Basic and Clinical Immunology (7th ed.) and Paul supra. For a discussion of how to make antibodies to selected antigens see Harlow and Lane (1989) supra.

Cell isolation or immunoassays for detection of cells during cell purification can be performed in any of several configurations, e.g., those reviewed in Maggio (ed.) (1980) Enzyme Immunoassay CRC Press, Boca Raton, Fla.; Tijan (1985) "Practice and Theory of Enzyme Immunoassays," Laboratory Techniques in Biochemistry and Molecular Biology, Elsevier Science Publishers B.V., Amsterdam; Harlow and Lane, supra; Chan (ed.) (1987) Immunoassay: A Practical Guide Academic Press, Orlando, Fla.; Price and Newman (eds.) (1991) Principles and Practice of Immunoassays Stockton Press, NY; and Ngo (ed.) (1988) Non-isotopic Immunoassays Plenum Press, NY.

Cells can be isolated and characterized by flow cytometry methods such a FACS analysis. A wide variety of flow-cytometry methods are known. For a general overview of fluorescence activated flow cytometry see, for example, Abbas et al. (1991) Cellular and Molecular immunology W.B. Saunders Company, particularly chapter 3, and Kuby (1992) Immunology W.H. Freeman and Company, particularly chapter 6. FACS machines are available, e.g., from Becton Dickinson.

Labeling agents which can be used to label cell antigen include, but are not limited to monoclonal antibodies, polyclonal antibodies, proteins, or other polymers such as affinity matrices, carbohydrates or lipids. Detection proceeds by any known method, such as immunoblotting, western blot analysis, tracking of radioactive or bioluminescent markers, capillary electrophoresis, or other methods which track a molecule based upon size, charge or affinity.

Antibodies

Certain aspects of this method require the use of antibodies. Such antibodies can be monoclonal or polyclonal. They can be antibody derivatives or antibody variants. They can be chimeric, humanized, or totally human. Using a protein or a polypeptide one of skill in the art can generate additionally antibodies which specifically bind to the receptor. A functional fragment or derivative of an antibody also can be used including Fab, Fab', Fab2, Fab'2, and single chain variable regions. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding for the protein or fragment thereof it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

Techniques for making such partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Russel et al. (2000) Infection and Immunity April 2000: 1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Delivery Reviews 31:33-42; Green and Jakobovits (1998) Exp. Med. 188(3): 483-495; Jakobovits (1998) Exp. Opin. Invest. Drugs 7(4): 607-614; Tsuda et al. (1997) Genomics 42:413-421; Sherman-Gold (1997). Genetic Engineering News 17:14; Mendez et al. (1997) Nature Genetics 15:146-156; Jakobovits (1996) WEIR'S HANDBOOK OF EXPERIMENTAL IMMUNOLOGY, THE INTEGRATED IMMUNE SYSTEM VOL. IV, 194.1-194.7; Jakobovits (1995) Current Opinion in Biotechnology 6:561-566; Mendez et al. (1995) Genomics 26:294-307; Jakobovits (1994) Current Biology 4:761-763; Arbones et al. (1994) Immunity 1:247-260; Jakobovits (1993) Nature 362:255-258; Jakobovits et al.

(1993) Proc. Natl. Acad. Sci. USA 90:2551-2555; Kucherlapati, et al. U.S. Pat. No. 6,075,181.

Antibodies can also be made using phage display techniques. Such techniques can be used to isolate an initial antibody or to generate variants with altered specificity or avidity characteristics. Single chain Fv can also be used as is convenient. They can be made from vaccinated transgenic mice, if desired.

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

The term "antibody variant" also includes "diabodies" which are small antibody fragments with two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen. The term also includes post-translational modification to linear polypeptide sequence of the antibody or fragment. The term "antibody variant" further includes "linear antibodies". The procedure for making such variants is known in the art and described in Zapata et al. (1995) Protein Eng. 8(10):1057-1062. Briefly, these antibodies comprise a pair of tandem Fd segments (VH~CH 1-VH—CH1) which form a pair of antigen binding regions. Linear antibodies can be bispecific or monospecific.

Methods to Detect Nucleic Acids

Various methods are known for quantifying the expression of a gene of interest (e.g. CD40L and/or IL-12p35) and include but are not limited to hybridization assays (Northern blot analysis) and PCR based hybridization assays. In assaying for an alteration in mRNA level such as IL-12 p35 mRNA or CD40L mRNA, the nucleic acid contained in a sample can be first extracted. For instance, mRNA can be isolated using various lytic enzymes or chemical solutions according to the procedures set forth in Sambrook et al. (1989), supra or extracted by commercially available nucleic-acid-binding resins following the accompanying instructions provided by the manufacturers. The mRNA contained in the extracted nucleic acid sample can then detected by hybridization (e.g., Northern blot analysis) and/or amplification procedures using nucleic acid probes and/or primers, respectively, according to standard procedures.

Nucleic acid molecules having at least 10 nucleotides and exhibiting sequence complementarity or homology to the nucleic acid to be detected can be used as hybridization probes or primers in the diagnostic methods. It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. For example, a probe useful for detecting CD40L mRNA is at least about 80% identical to the homologous region of comparable size contained in a previously identified sequence, e.g., see SEQ ID NOS: 1 or 3. Alternatively, the probe is at least 85% or even at least 90% identical to the corresponding gene sequence after alignment of the homologous region. The total size of fragment, as well as the size of the complementary stretches, will depend on the intended use or application of the particular nucleic acid segment. Smaller fragments of the gene will generally find use in hybridization embodiments, wherein the length of the complementary region may be varied, such as between about 10 and about 100 nucleotides, or even full length according to the complementary sequences one wishes to detect.

Nucleotide probes having complementary sequences over stretches greater than about 10 nucleotides in length will increase stability and selectivity of the hybrid, and thereby improving the specificity of particular hybrid molecules obtained. One can design nucleic acid molecules having gene-complementary stretches of more than about 25 and even more preferably more than about 50 nucleotides in length, or even longer where desired. Such fragments may be readily prepared by, for example, directly synthesizing the fragment by chemical means, by application of nucleic acid reproduction technology, such as the PCRTM technology with two priming oligonucleotides as described in U.S. Pat. No. 4,603,102 or by introducing selected sequences into recombinant vectors for recombinant production.

In certain embodiments, it will be advantageous to employ nucleic acid sequences of the present invention in combination with an appropriate means, such as a label, for detecting hybridization and therefore complementary sequences. A wide variety of appropriate indicator means are known in the art, including fluorescent, radioactive, enzymatic or other ligands, such as avidin/biotin, which are capable of giving a detectable signal. A fluorescent label or an enzyme tag, such as urease, alkaline phosphatase or peroxidase, instead of radioactive or other environmental undesirable reagents can also be used. In the case of enzyme tags, colorimetric indicator substrates are known which can be employed to provide a means visible to the human eye or spectrophotometrically, to identify specific hybridization with complementary nucleic acid-containing samples.

Hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, Sambrook, et al. (1989) supra. One can also utilize detect and quantify mRNA level or its expression using quantitative PCR or high throughput analysis such as Serial Analysis of Gene Expression (SAGE) as described in Velculescu et al. (1995) Science 270:484-487. Briefly, the method comprises isolating multiple mRNAs from cell or tissue samples suspected of containing the transcript. Optionally, the gene transcripts can be converted to cDNA. A sampling of the gene transcripts are subjected to sequence-specific analysis and quantified. These gene transcript sequence abundances are compared against reference database sequence abundances including normal data sets for diseased and healthy patients. The patient has the disease(s) with which the patient's data set most closely correlates and for this application, includes the differential of the transcript.

In certain aspects, it may be necessary to use polynucleotides as nucleotide probes or primers for the amplification and detection of genes or gene transcripts. A primer useful for detecting differentially expressed mRNA is at least about 80% identical to the homologous region of comparable size of a gene or polynucleotide. For the purpose of this invention, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, and reverse transcriptase.

General procedures for PCR are taught in MacPherson et al., PCR: A PRACTICAL APPROACH, (IRL Press at Oxford University Press (1991)). However, PCR conditions used for each application reaction are empirically determined. A number of parameters influence the success of a reaction. Among them are annealing temperature and time, extension time, $Mg^{2+}$ ATP concentration, pH, and the relative concentration of primers, templates, and deoxyribonucleotides.

After amplification, the resulting DNA fragments can be detected by agarose gel electrophoresis followed by visualization with ethidium bromide staining and ultraviolet illumination. A specific amplification of differentially expressed genes of interest can be verified by demonstrating that the amplified DNA fragment has the predicted size, exhibits the predicated restriction digestion pattern, and/or hybridizes to the correct cloned DNA sequence. Other methods for detecting gene expression are known to those skilled in the art. See, for example. International PCI Application No. WO 97/10365, U.S. Pat. Nos. 5,405,783, 5,412,087 and U.S. Pat. Nos. 5,445,934, 5,405,783; 5,412,087; 5,445,934; 5,578,832; 5,631,734; and LABORATORY TECHNIQUES IN BIOCHEMISTRY AND MOLECULAR BIOLOGY, Vol. 24: Hybridization with Nucleic Acid Probes, Tijssen, ed. Elsevier, N.Y. (1993).

Methods for Detecting and Quantifying Protein or Polypeptides

A variety of techniques are available in the art for protein analysis and include, but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays and PAGE-SDS.

Ex Vivo Therapy

As noted above, this invention also provides ex vivo therapeutic methods using the dendritic cells or educated T cells produced by the methods of this invention. For example, dendritic cells are transformed with an immunogen can be used to activate cytotoxic and helper T cells in vitro. Alternatively, the transformed dendritic cells are introduced into a mammal to activate the T cells in vivo. Yet further, T cells educated in vitro can be introduced into a mammal where they are cytotoxic against target cells bearing antigenic peptides corresponding to those the T cells are activated to recognize on class I MHC molecules. These target cells are typically cancer cells, or infected cells which express unique antigenic peptides on their MHC class I surfaces.

Similarly, helper T-cells, which recognize antigenic peptides in the context of MHC class II, can also be stimulated by the DCs of the invention, which comprise antigenic peptides both in the context of class I and class II MHC. Helper T-cells also stimulate an immune response against a target cell. As with cytotoxic Tcells, helper T-cells are stimulated with the recombinant DCs in vitro or in vivo.

The dendritic cells and T cells can be isolated from the mammal into which the DCs and/or activated T cells are to administered. Alternatively, the cells can be allogeneic provided from a donor or stored in a cell bank (e.g., a blood bank).

In Vivo Therapy

T cells or dendritic cells produced by the methods of this invention can be administered directly to the subject to produce T cells active against a selected immunogen. Administration can be by methods known in the art to successfully deliver a cell into ultimate contact with a subject's blood or tissue cells.

The cells are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route. Preferred routes of administration include, but are not limited to intradermal and intravenous administration.

Pharmaceutically acceptable carriers are determined in part by the particular composition being administered, as well as by the particular method used to administer the composition. Accordingly, there is a wide variety of suitable formulations of pharmaceutical compositions of the present invention. Most typically, quality controls (microbiology, clonogenic assays, viability tests), are performed and the cells are reinfused back to the subject, preceded by the administration of diphenhydramine and hydrocortisone. See, for example, Korbling et al. (1986) Blood 67:529-532 and Haas et al. (1990) Exp. Hematol. 18:94-98.

Formulations suitable for parenteral administration, such as, for example, by intraarticular (in the joints), intravenous, intramuscular, intradermal, intraperitoneal, intranodal and subcutaneous routes, and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intraderaml and intravenous administration are the preferred method of administration for DCs or T cells of the invention.

The dose of cells (e.g., activated T cells, or dendritic cells) administered to a subject is in an effective amount, effective to achieve the desired beneficial therapeutic response in the subject over time, or to inhibit growth of cancer cells, or to inhibit infection.

For the purpose of illustration only, the method can be practiced by obtaining and saving blood samples from the subject prior to infusion for subsequent analysis and comparison. Generally at least about $10^4$ to $10^6$ and typically, between $1\times10^8$ and $1\times10^{10}$ cells are infused intravenously or intraperitoneally into a 70 kg patient over roughly 60-120 minutes. In one aspect, administration is by intravenous infusion. Vital signs and oxygen saturation by pulse oximetry are closely monitored. Blood samples are obtained 5 minutes and 1 hour following infusion and saved for analysis. Cell re-infusions are repeated roughly every month for a total of 10-12 treatments in a one year period. After the first treatment, infusions can be performed on an outpatient basis at the discretion of the clinician. If the re-infusion is given as an outpatient, the participant is monitored for at least 4 hours following the therapy.

For administration, cells of the present invention can be administered at a rate determined by the effective donse, the LD-50 (or other measure of toxicity) of the cell type, and the side-effects of the cell type at various concentrations, as applied to the mass and overall health of the subject. Administration can be accomplished via single or divided doses. The cells of this invention can supplement other treatments for a condition by known conventional therapy, including cytotoxic agents, nucleotide analogues and biologic response modifiers. Similarly, biological response modifiers are optionally added for treatment by the DCs or activated T cells of the invention. For example, the cells are optionally administered with an adjuvant, or cytokine such as GM-CSF, IL-12 or IL-2.

In Vitro Assays and Kits

The present invention provides commercially valuable kits to practice the maturation methods of the invention. In one aspect, the kit comprises $IFN_\gamma$ polypeptide, or an expression cassette for expressing IFNγ mRNA in vivo or in vitro, and CD40L polypeptide, or an expression cassette for expressing CD40L mRNA in vivo or in vitro expression of CD40L. In another aspect, the kit comprises TNFα polypeptide, or an expression cassette for expressing TNFα mRNA in vivo or in vitro, and CD40L polypeptide, or an expression cassette for expressing CD40L mRNA in vivo or in vitro expression of CD40L. The kits may further comprise a RNA polymerase for in vitro transcription.

Methods to Assess Immunogenicity

The immunogenicity of the antigen presenting cells or educated T cells produced by the methods of the invention can be determined by well known methodologies including, but not limited to the following:

$^{51}$Cr-release lysis assay. Lysis of peptide-pulsed $^{51}$Cr-labeled targets by antigen-specific T cells can be compared. "More active" compositions will show greater lysis of targets as a function of time. The kinetics of lysis as well as overall target lysis at a fixed timepoint (e.g., 4 hours) may be used to evaluate performance. Ware et al. (1983) 3. Immunol. 131:1312.

Cytokine-release assay. Analysis of the types and quantities of cytokines secreted by T cells upon contacting modified APCs can be a measure of functional activity. Cytokines can be measured by ELISA or ELISPOT assays to determine the rate and total amount of cytokine production. Fujihashi et al. (1993) J. Immunol. Meth. 160:181; Tanquay and Killion (1994) Lymphokine Cytokine Res. 13:259.

In vitro T cell education. The compositions of the invention can be assayed for the ability to elicit reactive T cell populations from normal donor or patient-derived PBMC. In this system, elicited T cells can be tested for lytic activity, cytokine-release, polyclonality, and cross-reactivity to the antigenic epitope. Parkhurst et al. (1996) Immunol. 157:2539.

Transgenic animal models. Immunogenicity can be assessed in vivo by vaccinating HLA transgenic mice with the compositions of the invention and determining the nature and magnitude of the induced immune response. Alternatively, the hu-PBL-SCID mouse model allows reconstitution of a human immune system in a mouse by adoptive transfer of human PBL. These animals may be vaccinated with the compositions and analyzed for immune response as previously mentioned in Shirai et al. (1995) J. Immunol. 154:2733; Mosier et al. (1993) Proc. Natl. Acad. Sci. USA 90:2443.

Proliferation Assays. T cells will proliferate in response to reactive compositions. Proliferation can be monitored quantitatively by measuring, for example, $^3$H-thymidine uptake. Caruso et al. (1997) Cytometry 27:71.

Primate models. A non-human primate (chimpanzee) model system can be utilized to monitor in vivo immunogenicities of HLA-restricted ligands. It has been demonstrated that chimpanzees share overlapping MHC-ligand specificities with human MHC molecules thus allowing one to test HLA-restricted ligands for relative in vivo immunogenicity. Bertoni et al. (1998) Immunol. 161:4447.

Monitoring TCR Signal Transduction Events. Several intracellular signal transduction events (e.g., phosphorylation) are associated with successful TCR engagement by MHC-ligand complexes. The qualitative and quantitative analysis of these events have been correlated with the relative abilities of compositions to activate effector cells through TCR engagement. Salazar et al. (2000) Tnt. J. Cancer 85:829; Isakov et al. (1995) J. Exp. Med. 181:375).

In accordance with the above description, the following examples are intended to illustrate, but not limit, the various aspects of this invention.

Experimental Examples

Reagents

Histopaque 1077 and Tween 20 were purchased from Sigma (St Louis, Mo.). PBS and X-VIVO 15 were purchased from Cambrex (East Rutherford, Ni). AIM-V medium, Iscove's modified Dulbecco's medium and RPMI 1640 medium along with Trypan Blue and Fetal Bovine Serum (FBS) were purchased from Invitrogen (Carlsbad, Calif.). Viaspan was purchased from Dupont Pharma Labs (Wilmington, Del.). GM-CSF, IL-4, TNF-α, IL-1β, IL-6 and IFN-γ were all purchased from R&D Sytems (Minneapolis, Minn.). $PGE_2$ was purchased from Cayman Chemicals (Ann Arbor, Calif.). Soluble CD40L was purchased from Alexis Biochemicals (San Diego Calif.). Human AB serum was purchased from Valley Biochemical (Winchester, Va.).

Chemokines CCL19 and CCL21 were purchased from Peprotech (Rocky Hill, N.J.). Phenotyping antibodies (HLA-ABC, HLA-DR, CD80, CD86, CD83, CD14, and negative isotype controls), ELISpot antibody pairs (IFN-γ and IL-2) ELISA sets (IL-12 and IL-10) and streptavidin-HRP were all purchased from BD Pharmingen (San Diego, Calif.) along with BD Opt EIA reagent set B pH9.5. AEC peroxidase substrate was purchased from Vector labs (Vector Labs, Burlingame, Calif.). Blocking anti-CD40L antibody was purchased from eBioscience. CD1d/α-galactosylceramide (KRN7000) tetramer and native KRN7000 were kind gifts from Kirin Brewery, Pharamaceuticals Division, Tokyo, Japan. MART-1/HLA-A201 tetramers were purchased from Beckman-Coulter (Miami, Fla.)

DC Generation

Human PBMCs were isolated from Leukapheresis collections from healthy volunteers provided by Life Blood (Memphis, Tenn.). PBMCs were prepared by Ficoll-Histopaque density centrifugation and washed four times in PBS at room temperature. 2×10$^8$ PBMCs were re-suspended in 30 ml AIM-V medium and allowed to adhere to 150 cm$^3$ plastic flasks for 2 hours at 37° C. Non-adherent cells were removed and remaining cells cultured in X-VIVO 15 medium, supplemented with GM-CSF (1000 U/ml) and IL-4 (1000 U/ml), for 5-6 days at 37° C., 5% $CO_2$.

Cloning of CD40L

T cells were stimulated with PMA in RPMI for 1 hr. Cells were harvested and washed with PBS once. Total RNA was extracted using QIAGEN RNeasy procedure. One microgram of total RNA from activated T cells was taken into one tube RT-PCR reaction using Gene Amp Gold kit (Applied Bioscience) using a high fidelity Advantage Polymerase (Clontech). Gene specific primers for CD40L sequence correspond to bases 47 and 859 of CD40L sequence CD40L 5' primer: 5'-GCATCATCGAAACATACAACC-3' (SEQ ID NO. 11) and CD40 3' primer: 5'-GTATTATGAAGACTC-CCAGCG-3' (SEQ ID NO. 12). The PCR fragment was purified and subcloned into pCR2.1 vector using T4 DNA ligase (Invitrogen). Sequence analysis of the CD40L open reading frame and alignment with a GenBank consensus sequence revealed presence of two mutations. One mutation was conservative and did not lead to amino acid change. Another substitution resulted in a functional amino acid change Asn-Ser. Site directed mutagenesis was performed to correct the non-conservative amino acid change back to asparagine. Briefly, 10-40 ng of CD40L PCR2.1 plasmid DNA was used in site directed mutagenesis using custom 5' phosphorylated and HPLC purified primers (QIAGEN), PFU Ultra enzyme with accompanying 10×PCR buffer (Stratagene) and dNTPS (Clontech) Following the PCR reaction, Dpn I restriction enzyme (Promega) was added and incubated for 1 hour at 37° C. to digest away parental template. Five microliters of this reaction was then transformed into Oneshot MACH T1R competent cells (Invitrogen) and plated out on freshly made ampicillin containing LB plates. Six colonies were selected and grown as 3 mL cultures overnight in LB containing ampicillin. DNA was isolated using plasmid miniprep (QIAGEN). An aliquot of purified DNA for each clone was submitted to the University of North Carolina (UNC) sequencing facility for sequence analysis of the CD40L open reading frame using M13F and M13R primers (Invitrogen). All the clones were then aligned to a consensus GenBank Sequence for CD40L using DNAS-TAR Seqman analysis software. Clone #2 (renamed CD40L WT PCR 2.1) was selected for containing the correct mutagenized bases.

Generation of mRNAs for Transfection of DCs

CD40L WT PCR 2.1 plasmid was linearized using SpeI restriction enzyme and purified by phenol/chloroform extraction followed by ethanol precipitation. The linear template was reconstituted in water and transcribed in vitro using mMessage mMachine T7 Ultra kits (Ambion) following the manufacturer's directions. An aliquot of RNA was saved for final analysis prior to proceeding to polyadenylation reaction. Polyadenylated RNA was purified using RNeasy column (QIAGEN) following protocol for RNA cleanup. RNA was eluted in water and stored in individual size aliquots below −150° C. PolyA tail length was determined by the comparative analysis of non-polyadenylated RNA and final product using RNA Bioanalyzer 2100.

Electroporation of DCs

Prior to electroporation, DCs were harvested and washed in PBS and then re-suspended in chilled Viaspan® (Barr Laboratories) at $4 \times 10^7$/ml in 0.5 ml or $2.5 \times 10^7$/ml in 0.2 ml and placed on ice. DCs were mixed with mRNA (1 or 2 μg/$10^6$ for mRNA encoding antigen and 4 μg/$10^6$ for CD40L mRNA) and placed in a 4 mm gap electroporation cuvette and electroporated using Biorad apparatus. Immediately after electroporation, DCs were washed in X-VIVO 15 medium and finally re-suspended in X-VIVO 15 supplemented with GM-CSF (800 U/ml) and IL-4 (500 U/ml) at $1 \times 10^6$/ml and cultured for either 4 or 24 hours at 37° C. in low adherence six well plates (BD Biosciences, Franklin Lakes, N.J.). Additional maturation stimuli, described below, were also added at this point.

DC Maturation—CD40L Base Process.

Following electroporation, DCs transfected with CD40L mRNA were treated with IFN-γ (1000 U/ml) or TNF-α (10 ng/ml) or a combination of IFN-γ and $PGE_2$ (1 μg/ml). By comparison, immature DCs were transfected with various antigen-encoding mRNAs and were then treated with a "cytokine cocktail" comprising of TNF-α (10 ng/ml), IL-1β (10 ng/ml), IL-6 (100 ng/ml) and $PGE_2$ (1 μg/ml) or soluble CD40L (200 ng/ml) plus enhancer (1 μg/ml) with either simultaneous or sequential addition of 1000 U/ml IFN-γ.

DC Maturation—PME-CD40L Process.

Immature DCs were phenotypically matured on Day 5 of culture with TNF-α (10 ng/ml), IFN-γ (1000 U/ml) and $PGE_2$ (1 μg/ml). On day 6, DCs were harvested and electroporated with antigen and CD40L mRNA as described above, and cultured in X-VIVO 15 media containing 800 U/ml GM-CSF and 500 U/ml IL-4 for 4 hrs prior to harvest, or formulation for vaccine production.

DC Maturation with the CD40L Base Process, in Combination with α-Galactosylceramide (KRN7000)

100 ng/ml of KRN7000 was pulsed onto the CD40L base process DCs immediately post electroporation in combination with 500 U/ml IFN-γ and 1 μg/ml $PGE_2$, for 24 hrs of culture.

Flow Cytometry Analysis of DCs $10^6$ DCs were harvested and re-suspended in chilled PBS/1% FCS. Phycoerythrin (PE) or FITC conjugated antibodies specific for MHC molecules (HLA-ABC, HLA-DR), co-stimulatory molecules (CD80, CD86), maturation markers (CD83) and monocyte markers (CD14) were mixed with $1 \times 10^5$ DCs per well in a 96 well plates (BD Biosciences) and incubated at 4° C. for a minimum of 15 minutes. Isotype matched antibodies were used as controls. After thorough washing, fluorescence analysis was performed with a FACScalibur flow cytometer (BD Biosciences) using CellQuest software (BD Biosciences).

Intracellular expression of CD40L was determined as follows: $2 \times 10^5$ DCs or HeLa cells were harvested at various time points post transfection with CD40L mRNA and re-suspended in 250 μL of Cytofix/Cytoperm solution (BD Biosciences) for a minimum of 10 minutes up to 2 hours at 4° C. Cells were washed twice with 2 ml staining buffer (PBS, BSA, $NaN_3$, and EDTA), re-suspended in 0.5 ml staining buffer and stored over night at 4° C. Cells were re-suspended in 2.0 ml Perm/Wash solution (BD Biosciences) for 15 minutes, centrifuged and re-suspended in 100 μl Perm/Wash solution. 20 μL of mouse anti-human CD40L PE and anti-human CD40 APC (BD Biosciences) or mouse IgG1 PE and IgG1 APC (BD Biosciences) was added to each DC preparation collected and permeabilized at each time point, and incubated at 4° C. for 30 minutes in the dark. Cells were washed twice with 1 ml Perm/Wash solution and re-suspended in staining buffer prior to flow cytometric analysis.

Intracellular cytokine staining (ICS) was performed as follows: $1 \times 10^6$/ml primed CD8+ T cells, removed from co-culture on day 19 and re-stimulated in 200 μl R10 media with PME DC targets (RCC, survivin, G250, hTERT or eGFP) at 37° C.; 5% $CO_2$ for 1 hour prior to the addition of brefeldin A (BD GolgiPlug, Cat No. 555029) at 1 μl/ml. Cells incubated at 37° C. for a further 16 hours. Cells were washed and resuspended in 150 μl FACS buffer with 5 μl CD8 per CP-cy5.5 (BD 341051) and incubated at 4° C. After 30 minutes cells were washed twice and resuspended in 2% paraformaldehyde (PFA). Cells were subsequently washed after 10 minutes, and then permeabilized in 0.1% saponin for 10 minutes at room temperature (RT), prior to incubation with 2 μl of blocking antibody, Mouse IgG1 pure (BD 349040). After 10 minutes incubation at RT, 0.5 μl IFN-γ-APC (BD 554681), 10 μl IL-2-FITC (BD 554702) and 10 μl CD69-PE (BD 555531) antibodies were added to each sample tube. Samples were incubated for 30 minutes in the dark at RT. Cells were resuspended in 2% PFA following a final wash in 0.1% saponin. Analysis undertaken by FACS cytometery, collecting 100,000 events.

CD40L Functional Analysis when Expressed from mRNA in HeLa Cells

HeLa cells were grown in 10% FBS/DMEM and then harvested and electroporated in 4 mm cuvettes with GFP and CD40L RNA (20 μg each/$5 \times 10^6$ cells). Post-transfection recovery was ~70% and the cells were plated in 6 well dishes and allowed to grow overnight. Following the overnight incubation, transfected HELA cells were harvested by scraping and stained with either mouse IgG1-PE or anti-human CD40L-PE (both from BD Biosciences, San Diego, Calif.) to look for cell surface expression of CD40L. $2 \times 10^5$ cells/tube were stained with 10 μg/ml of antibody in 1% FBS/PBS for 30 minutes at 4° C. The cells were analyzed using a FACScaliber flow cytometer and Cellquest software (BD Biosciences). To analyze the function of the HeLa expressed CD40L, $1 \times 10^6$ immature dendritic cells were co-cultured with $1 \times 10^6$ HeLa cells in 5% huAB serum/RPMI supplemented with 1000 U/ml of IFN-γ (R&D Systems, Minneapolis, Minn.) in 6 well dishes (2 mls total volume) overnight. A blocking CD40L monoclonal antibody (24-31 from eBioscience) was included at 10 μg/ml in matched wells to confirm that cell surface expression of the protein was required for stimulating the dendritic cells. The culture supernatant was harvested after 18-24 hours and expression of the cytokines IL-10 and IL-12 analyzed by ELISA (BD Biosciences).

Migration Assay

Chemotaxis of DCs was measured by migration through a 8 μm pore size polycarbonate filter in 24 well transwell chambers (corning Costar, Acton, Mass.). 5% human AB serum in Iscoves modified Dulbecco's medium or AIM-V medium containing 3-300 ng/ml CCL19, 5-250 ng/ml CCL21, a combination of both or medium alone was added to the lower chamber. $1-5 \times 10^5$ DCs in 0.1 ml were added to the upper chamber and incubated for 2-3 hours at 37° C. Lower chamber harvested into 5 ml tubes (BD Biosciences) and re-suspended in 0.1 ml PBS and viable cell counts undertaken using trypan blue.

ELISpot

PVDF membrane ELISpot plates (Millipore, Balleríca, Mass.) were coated with 5 μg/mL monoclonal anti-IFN-γ or anti-IL-2 capture antibody (BD Pharmingen, San Diego, Calif.) and incubated at 4° C. for 24 hours. After incubation, plates were washed with PBS/0.05% Tween 20, and blocked with 5% human AB serum/RPMI 1640 medium for 1 hour. PBMCs, T-cells, or CD8 enriched T cells, were plated at $1 \times 10^5$ cells/well and mRNA transfected, antigen-loaded DC targets at $1 \times 10^4$ cells/well for a 10:1 effector:target ratio, and incubated at 37° C., 5% $CO_2$ for a minimum of 16 hours.

Following incubation, plates were washed 6 times, and anti-IFN-γ detection antibody (BD Pharmingen) or anti-IL-2 detection antibody (BD Pharmingen) was added to the appropriate plates at 1 μg/ml for 2 hours. After a further six washes, Streptavidin-HRP (BD Pharmingen) was added to each well for 1 hour. Finally, after another wash cycle, color development was undertaken with AEC Peroxidase Substrate for 5-15 minutes and stopped with water. The plates were left to air dry prior to analysis on CTL Immunospot Plate Reader (CTL, Cleveland, Ohio).

ELISA

The method as laid out by BD Pharmingen for IL-12 and IL-10 ELISA sets (BD Pharmingen) using BD Opt EIA reagent set B pH 9.5. Briefly, ELISA plates (BD Biosciences) were coated with anti-IL-12p70 or anti-IL-10 ELISA capture antibody in coating buffer for 24 hours at 4° C. Plates underwent blocking with 200 μl per well 10% FCS/PBS for one hour prior to the addition of standards (BD Pharmingen) and supernatant samples, in duplicate, at 100 μl per well and incubated at room temperature for 2 hours. Plates were washed and anti-cytokine detection antibody added, incubated for one hour, the plates washed and solutions replaced with 100 μl of streptavidin-HRP and further incubated for one hour at room temperature. Again plates were washed and color development substrates applied for 10-20 minutes, followed by cessation of color development with stop solution. Plate analysis undertaken using Bio-Tek instruments ELx800 plate reader with KC junior software (Winooski, Vt.). The results show the number of picograms/ml/$10^6$ DCs. Because the assays were set up so that 1 ml corresponds to $10^6$ DCs, the results can also be expressed as number of picograms/$10^6$ DCs. For example, 3000 pg/ml/$10^6$ DCs is equivalent to 3000 pg/$10^6$ DCs.

CTL Induction

Mature dendritic cells transfected with mRNAs were co-cultured with CD8 purified T-cells. All co-cultures were performed in R-10 media (10% FBS, RPMI-1640 supplemented with 10 mM HEPES pH 7.4, 1 mM sodium pyruvate, 0.1 mM non-essential amino acids, 2 mM sodium glutamate, 55 μM β-mercaptoethanol). All cell culture reagents were from Invitrogen (Carlsbad, Calif.). $CD8^+$ cells were purified using the $CD8^+$ T Cell Isolation kit II (Miltenyi Biotec, Auburn, Calif.) from non-adherent cells harvested from the monocyte adherence step. The $CD8^+$ cells are mixed with dendritic cells prepared as described above at 10:1 $CD8^+$:DC. For the first seven days the cells were cultured in media supplemented with 0.2 U/ml IL-2 (R&D Systems, Minneapolis, Minn.) and then aliquoted into 24-well tissue culture dishes at 1 ml ($1 \times 10^6$ $CD8^+$ cells)/well. Following this initial seven day incubation the CD8+ cells were harvested, counted and re-cultured with fresh DC stimulators at 10:1 in media supplemented with 5 U/ml IL-2. Again the cells were cultured for one week and then restimulated with fresh DC and 20 U/ml IL-2. CTL assays were performed 3 or 7 days following the third stimulation.

CTL Assay

T2 cells were previously pulsed with 10 μg/ml of either the HLA-A201 restricted MART-APL peptide (LAGIGILTV; SEQ ID NO:24) or native peptide (AAGIGILTV; SEQ ID NO:25) or PSA-1 peptide (FLTPKKLQCV; SEQ ID NO:26) by overnight incubation in FBS/RPMI media, and washed prior to use as CTL targets. Dendritic cell targets were transfected with either GFP mRNA, MART-1 APL mRNA, Flu-M1 mRNA, as described above and incubated overnight without maturation. Pulsed T2 cells were incubated with 100 μCi of $Na^{51}Cr$ (Perkin-Elmer Life and Analytical Sciences, Inc., Boston, Mass.) for 90 minutes at 37° C. Excess $^{51}Cr$ was washed away and 5000 labeled targets incubated with various E:T ratios of CD8+ cells for 4 hours. Non-specific lysis was reduced by the addition of unpulsed T2 cells at 25,000 cells per well. Released $^{51}Cr$ was measured in the supernatant by scintillation counting. Total release was calculated by addition of 1% Triton X-100 to the targets while spontaneous release was calculated by addition of media alone. Percent lysis was calculated using the formula (sample cpm released-spontaneous cpm)/(total cpm released–spontaneous cpm released).

Induction of MART-1 Specific CTLs Employing KRN7000-Pulsed CD40L Base Process Matured DC DCs were generated as described above, employing the 'CD40L base process', and loaded with mRNA encoding MART-1. Post electroporation, DCs were incubated with KRN7000, IFN-γ and $PGE_2$. DCs and PBMCs were co-cultured at a 1:10 ratio in the presence of 20 U/ml IL-2. PBMCs were restimulated three times under the same conditions, and the frequency of CTL induction determined by staining with MART-1/A2 tetramers, and the expansion of NKT-cells enumerated using KRN7000/CD1d tetramers by FACS.

Results of Experimental Examples

Sequential Maturation with Interferon-γ and CD40L Optimizes IL-12p70 Secretion

Immature DCs were prepared by 6 day culture of adherent cells PBMCs in X-VIVO 15 media, inclusive of GM-CSF and IL-4. DCs were recovered on Day 6 and electroporated with 2 μg of eGFP encoding mRNA per million DCs, and matured for 36 hrs with "cytokine cocktail". Alternatively, maturation was achieved by culturing the DCs in the presence of IFN-γ and soluble CD40L, applied simultaneously, or sequentially. DCs were monitored for increased expression of co-stimulatory molecules, but most importantly for the secretion of IL-12p70 versus IL-10. FIG. 1 shows that DCs matured with the cytokine cocktail secrete excess IL-10 in comparison to IL-12p70 into the culture supernatant over the 36 hr culture period. By contrast, DCs matured simultaneously with soluble CD40L plus IFN-γ secrete excess IL-12p70. However, sequential application of IFN-γ for 18 hrs, followed by the addition of soluble CD40L directly to the culture, and an additional 18 hr culture period resulted in significantly enhanced levels of IL-12p70 secretion. Unexpectedly, the application of soluble CD40L, followed by IFN-γ, prevented significant secretion of IL-12p70. In conclusion, the sequential delivery of an innate stimulus to "prime" DC maturation (IFN-γ), followed by a surrogate T-helper cell signal delivered by soluble CD40L, optimizes DC maturation for IL-12p70 secretion.

Co-Culture of HeLa Cells, Transfected with mRNA Encoding CD40L, with Immature DCS Results in the Induction of DC Derived IL-12p70.

Figure 2:
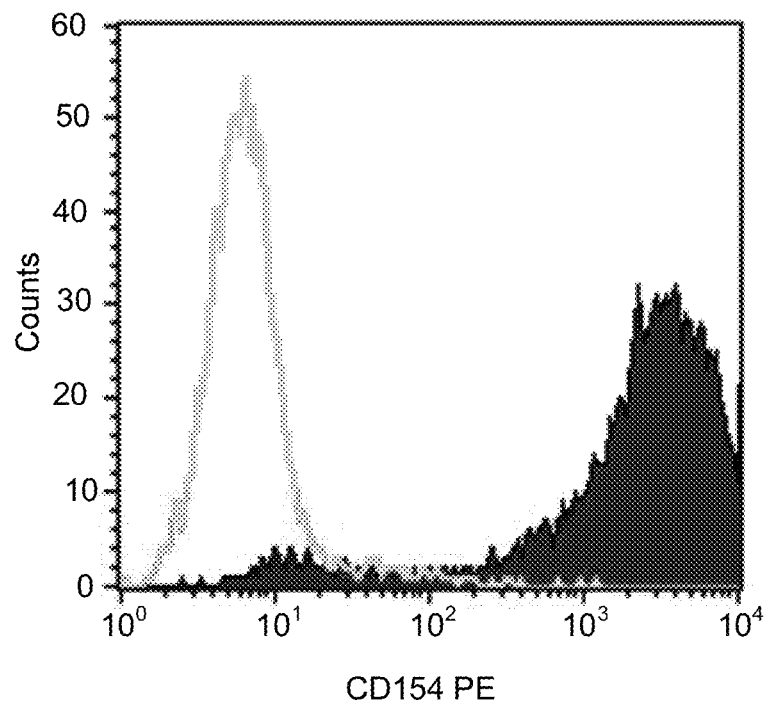
FIG. 2 shows that HELA cells transfected with mRNA encoding CD40L and having a polyA tail of >400 nucleotides express cell surface protein, as defined by FACS analysis with anti-CD40L (CD154) antibody.

FIG. 2 shows that HeLa cells transfected with mRNA encoding CD40L results in significant cell surface expression of CD40L protein after 24 hrs of culture, as defined by an anti-CD40L antibody and flow cytometry. CD40L mRNA transfected HeLa cells were co-cultured with immature DCs, in the presence of 1000 U/ml IFN-γ. Table II shows that HeLa cells transfected with an extended poly-A tail (>400 'A's) are capable of inducing significant IL-12p70 secretion when cultured with immature DCs over the 18 hr culture period. Importantly, the inclusion of a blocking anti-CD40L antibody prevents IL-12p70 secretion, and confirms the identity and functional importance of protein encoded by the transfected mRNA sequence.

TABLE II

HeLa cells transfected with CD40L encoding mRNA, when co-cultured with immature DCs in the presence of IFN-γ, results in the secretion of IL-12p70. Inclusion of 'blocking' anti-CD40L antibody in the culture prevents the induction of IL-12p70.

|  | Immature DCs IL-12p70 (pg/ml) | "Cocktail" matured and reactivated DCs IL-12p70 (pg/ml) |
|---|---|---|
| DC's alone | — | 4.9 |
| (a) HeLa/>400 polyA + IFN-γ | 372 | 26.3 |
| (b) HeLa/>400 polyA + IFN-γ + 24-31 | — | 2.5 |

(a) HeLa cells were transfected with 4 μg of CD40L mRNA bearing greater than 400 nucleotide poly-A tail, and incubated with DCs in the presence of IFN-γ.
(b) As (a) but in the presence of blocking anti-CD40L antibody (24-31).

Dendritic Cells Transfected with CD40L mRNA, and Cultured in the Presence of IFN-γ Secrete IL-12p70.

Figure 3:
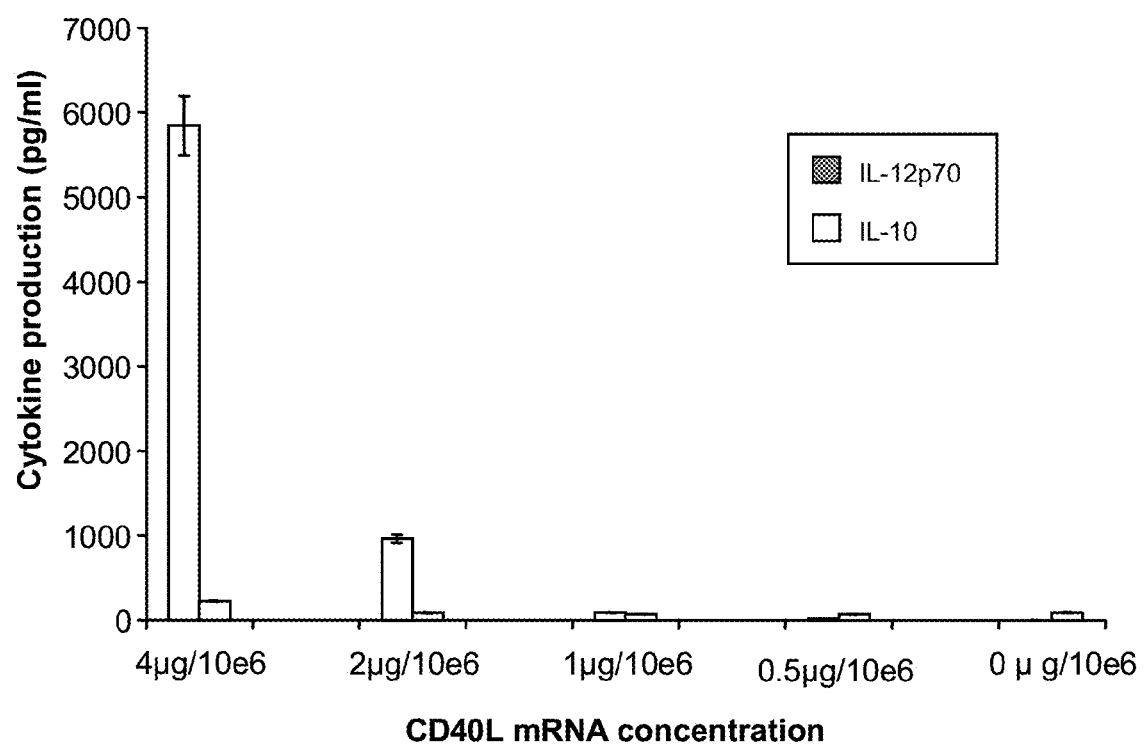
FIG. 3 shows that IL-12p70 secretion from CD40L mRNA transfected cells is proportional to the size of the transfection payload. DCs were transfected with a titration of CD40L mRNA followed immediately by the addition of 1000 U/ml IFN-γ. At least 4 μg per million DCs of CD40L mRNA is required to induce significant levels of IL-12p70 release.
Figure 4:
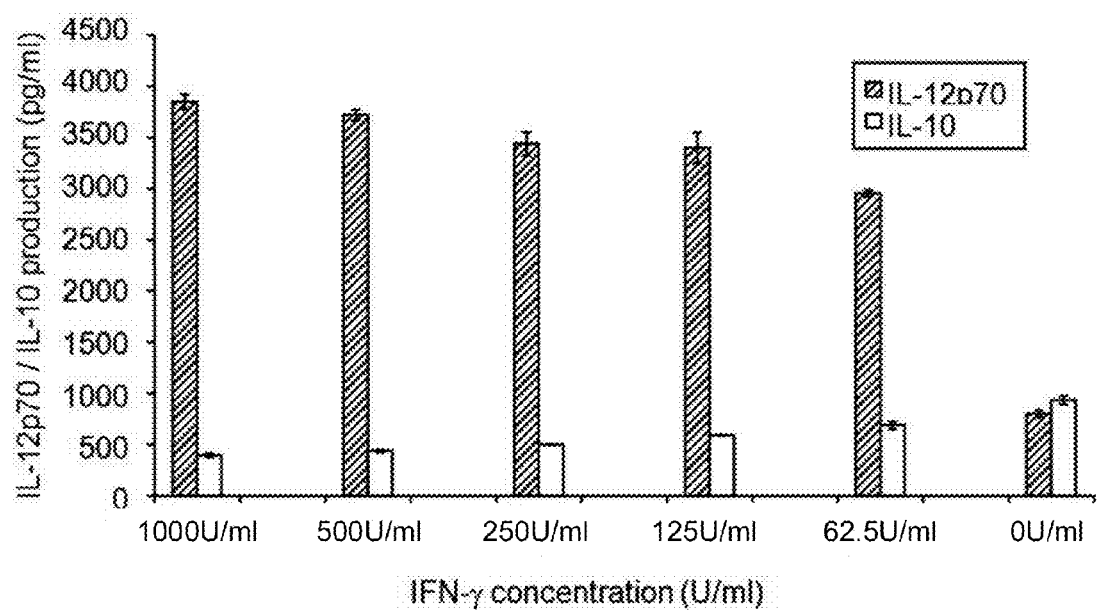
FIG. 4 shows that at least 100 U/ml of IFN-γ is required to synergize with the CD40L mRNA payload to induce maximal IL-12p70 secretion. DCs were transfected with 4 μg CD40L mRNA per million cells, and immediately incubated with a titration of IFN-γ. IL-12p70 and IL-10 were measured in culture supernatants after 24 hrs.
Figure 5A:
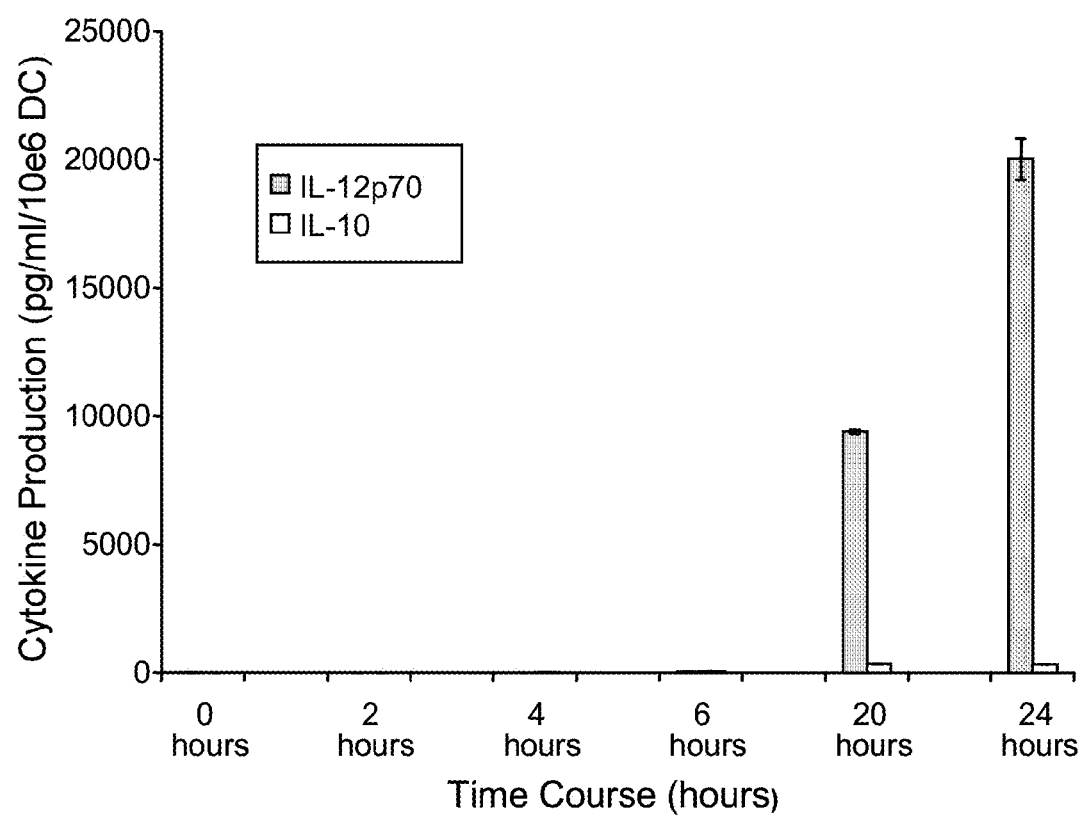
FIG. 5A shows that IL-12p70 secretion induced by CD40L/IFN-γ occurs approximately 24 hrs after transfection of DCs and culture in the presence of IFN-γ. DCs were transfected with 4 μg CD40L mRNA per million cells, and immediately cultured with 1000 U/ml IFN-γ. Supernatants were collected from replica cultures at the designated times, and assayed for IL-12p70 and IL-10 content.
Figure 5B:
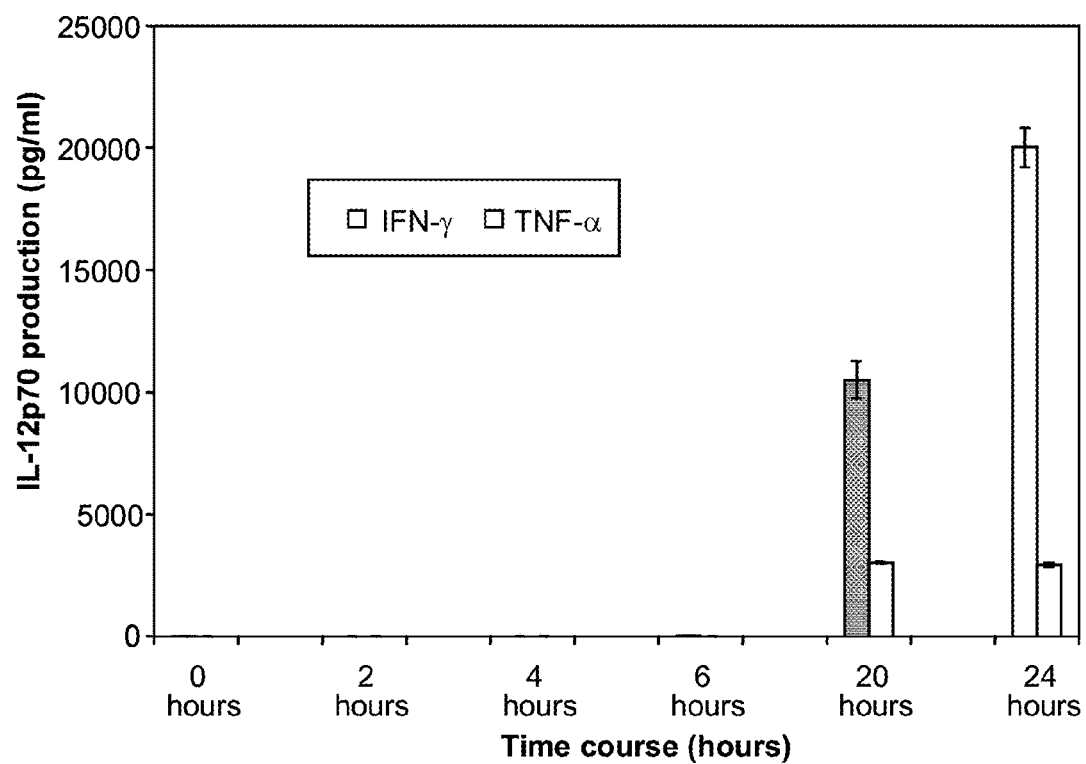
FIG. 5B shows that addition of TNF-α to CD40L mRNA transfected DCs results in the generation of IL-12p70, but the level of expression is less than that achieved with IFN-γ as the co-maturation agent.
Figure 5C:
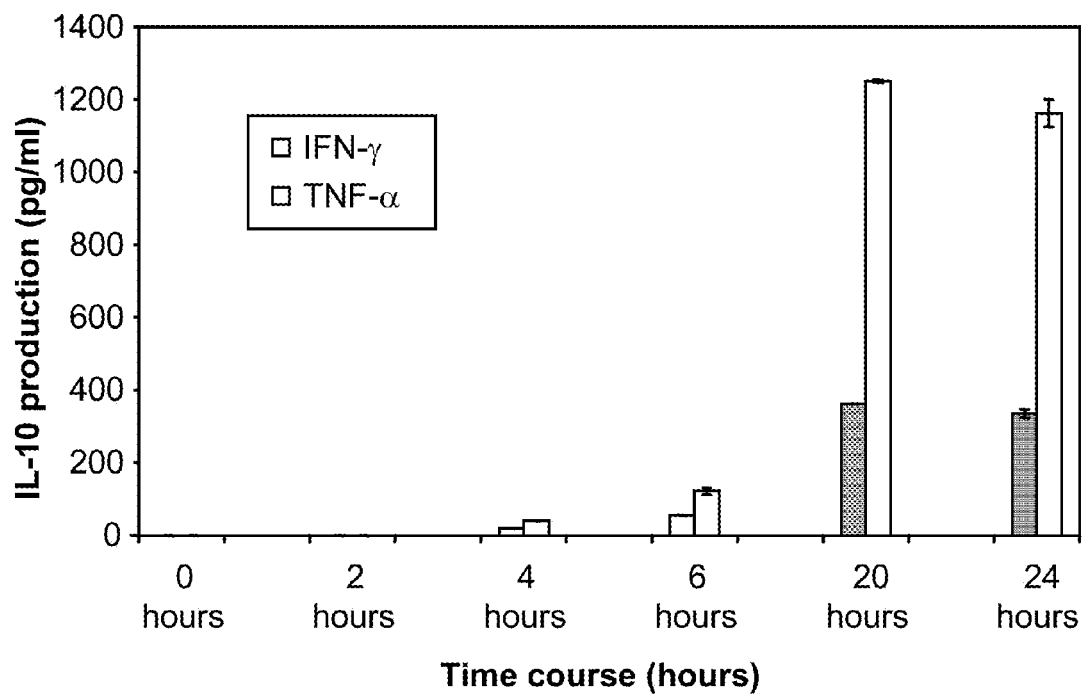
FIG. 5C shows that the use of TNF-α as the co-maturation factor also results in elevated levels of IL-10 compared to the use of IFN-γ.

Immature DCs were harvested after 6 days in culture with GM-CSF and IL-4, and transfected with a titration of CD40L mRNA (400-polyA), and immediately cultured in the presence of 1000 U/ml IFN-γ. FIG. 3 shows that supernatants harvested after 18 hrs of culture contain excess IL-12p70 over IL-10, and that at least 4 μg of CD40L mRNA per million DCs is required for optimal cytokine secretion. Increasing the CD40L mRNA payload above 4 μg per million DCs results in a significant reduction in DC yield post maturation (data not shown). In a parallel experiment, immature DCs were transfected with 4 μg CD40L mRNA per million cells, and a titration of IFN-γ immediately applied to the cultures. FIG. 4 shows that at least 100 U/ml of IFN-γ is required to support optimal induction of IL-12p70. FIG. 5a shows that IL-12p70 appears at detectable levels 6 to 8 hrs post transfection and coculture with IFN-γ, with optimal accumulation in the culture supernatant being recorded between 20 and 24 hrs. By contrast, the substitution of 10 ng/ml TNF-α for IFN-γ also supports IL-12 production, but at reduced levels (FIG. 5b). Moreover, IFN-γ results in concomitantly lower levels of IL-10 production than does TNF-α. (FIG. 5c)

Induction of IL-12p70 by DCs Transfected with CD40L mRNA is Dependent on "Intracellular Signaling" as Opposed to Cell-Cell Interactions.

Figure 6A:
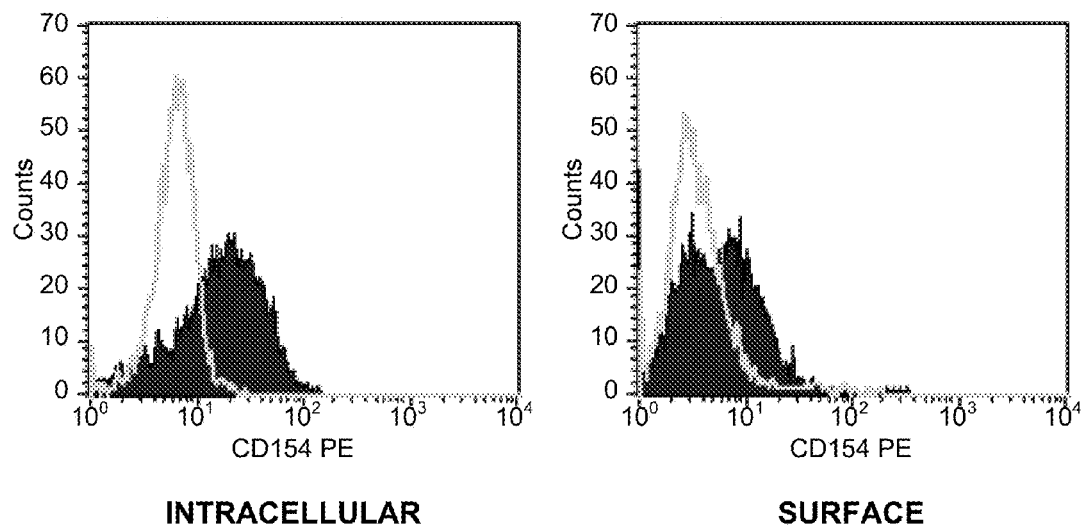
FIGS. 6A and 6B show that DCS transfected with mRNA encoding CD40L demonstrate cellular expression as defined by FACS analysis with anti-CD40L (CD154) antibody.
Figure 6B:
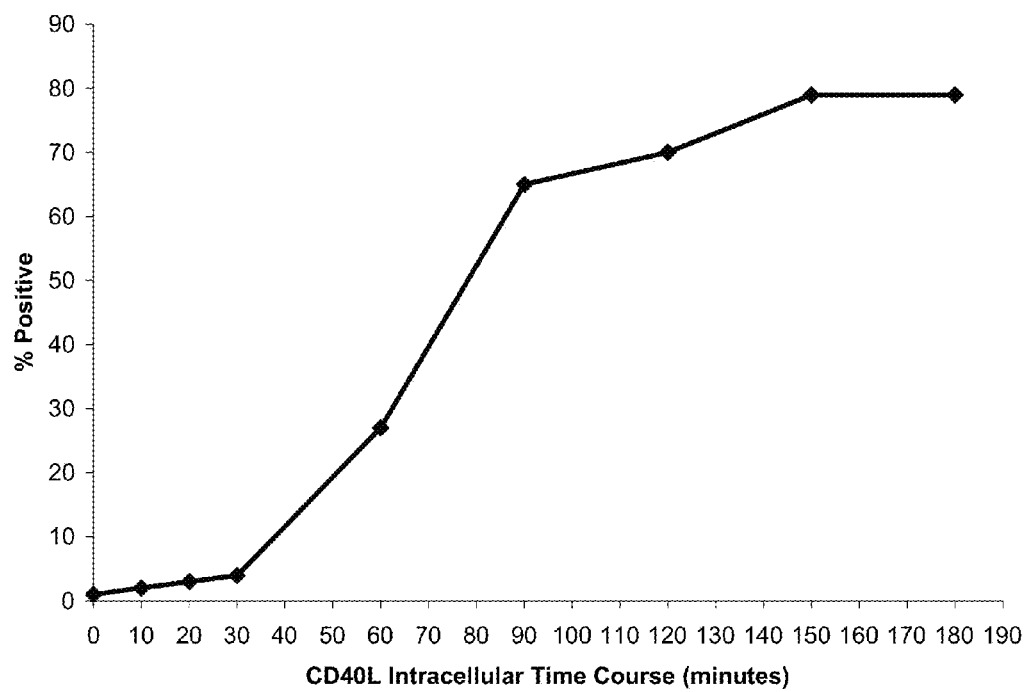
Figure 7:
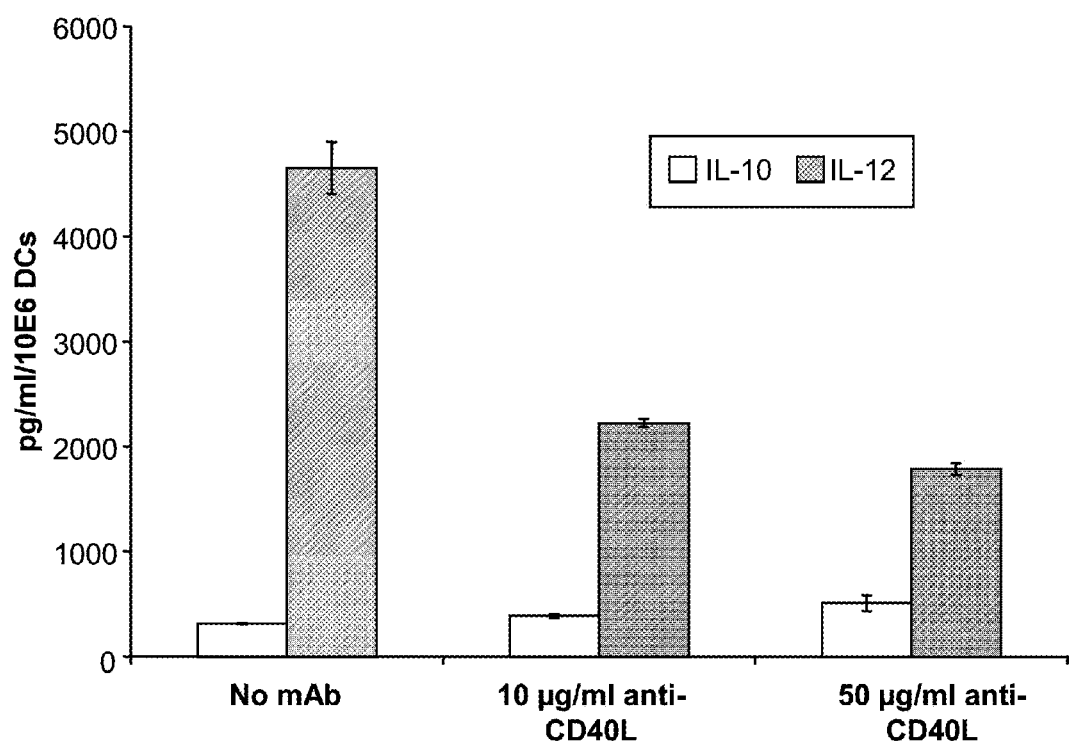
FIG. 7 shows that DCs transfected with CD40L mRNA and cultured in the presence of IFN-γ secrete IL-12p70 despite the presence of an excess of blocking anti-CD40L antibody, CD40/CD40L interactions operate within an "intracellular" compartment. DCs were transfected 4 μg CD40L mRNA and immediately cultured with 1000 U/ml IFN-γ in the presence of either 10 or 50 μg/ml of blocking anti-CD40L antibody. IL-12 p70 release is reduced by only 50%, indicating that intracellular signaling, rather than cell to cell signaling is the primary pathway for the induction of IL-12p70.

FIG. 2 demonstrates that CD40L protein translated from mRNA can be expressed on the cell surface of the transfected cells, and that the protein retains the ability to appropriately signal DCs for IL-12p70 secretion as a consequence of its interaction with its counterpart on DCs, namely CD40. To determine the cellular distribution of CD40L in transfected DCs, and to confirm its functional identity, DCs were harvested at various time points post transfection, the presence of CD40L on the cell surface, or intracellular compartments was determined. FIGS. 6a and 6b show that the majority of CD40L is localized within an intracellular compartment, and that significant protein expression (27% DCs CD40L positive) was not apparent until 60 minutes post transfection. Thus, although IFN-γ is applied immediately post transfection, the delivery of the maturation events is sequential, with the IFN-γ signal preceding that of CD40L. As shown in FIG. 1, sequential maturation of DCs with IFN-γ and CD40L optimizes for IL-12p70 secretion. In addition, FIG. 7 shows that CD40L transfected and IFN-γ treated DCs, when cultured in the presence of excess blocking anti-CD40L antibody for 18 hrs post transfection, still secrete significant levels of IL-12p70. This data shows that CD40L/CD40 interactions, which are required for IL-12p70 production in this system, can take place within the intracellular compartment.

Frequency of CD40L Positive Cells Over Time

Figure 6C:
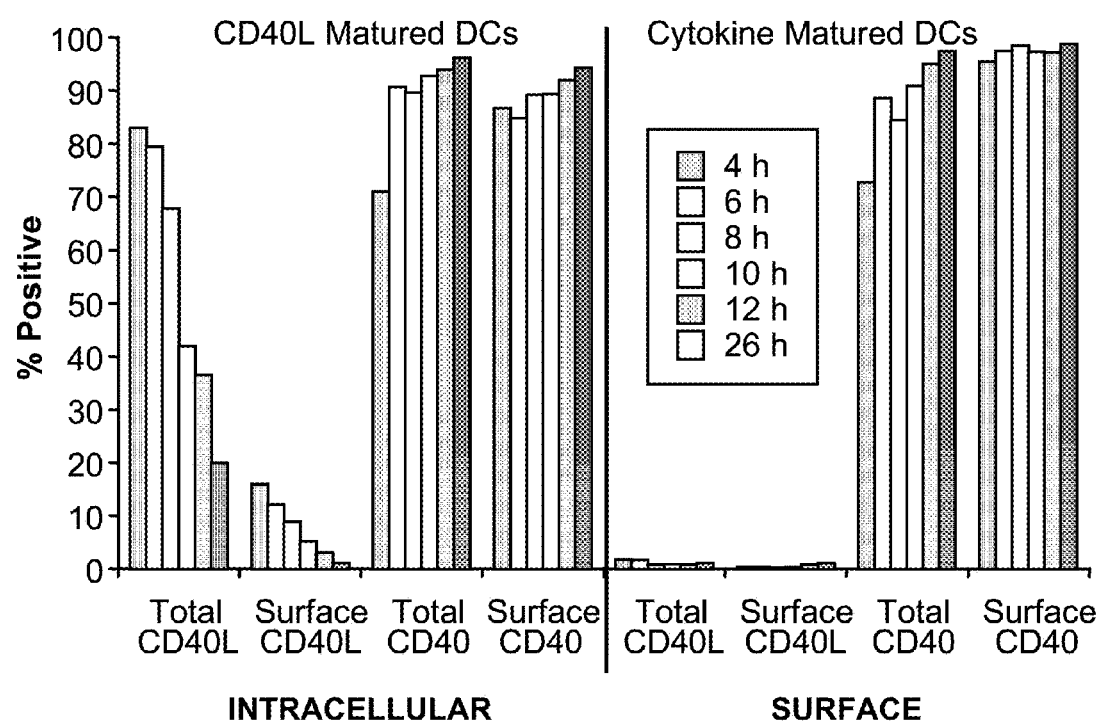
FIG. 6C shows transient expression of CD40L protein post transfection of DC with CD40L encoding mRNA.

Immature DCs were transfected with 4 μg CD40L mRNA per 10⁶ DC, and co-matured with 1000 U/ml IFN-γ. Alternatively, and by way of negative control for CD40L staining, immature DCs were matured with 'cytokine cocktail'. Maximum frequency of expression is achieved around 3 to 4 hrs post transfection with CD40L RNA (see FIG. 6b), although 80% of DCs express CD40L when the cells are fixed and permeabilized, cell surface staining only detects approximately 15% of the DCs (FIG. 6c). This data shows that the bulk of the CD40L protein is retained within the DC, and is not expressed at the cell surface. CD40L protein is transiently expressed, with the majority of DCs becoming CD40L negative 26 hrs post transfection. The expression of CD40, the cognate receptor molecule for CD40L, is not altered by transfection of DCs with mRNA encoding CD40L, when compared to DCs receiving 'cytokine cocktail' only.

PGE$_2$ is Required to Induce DC Migration on Maturation with CD40L and IFN-γ

Figure 8:
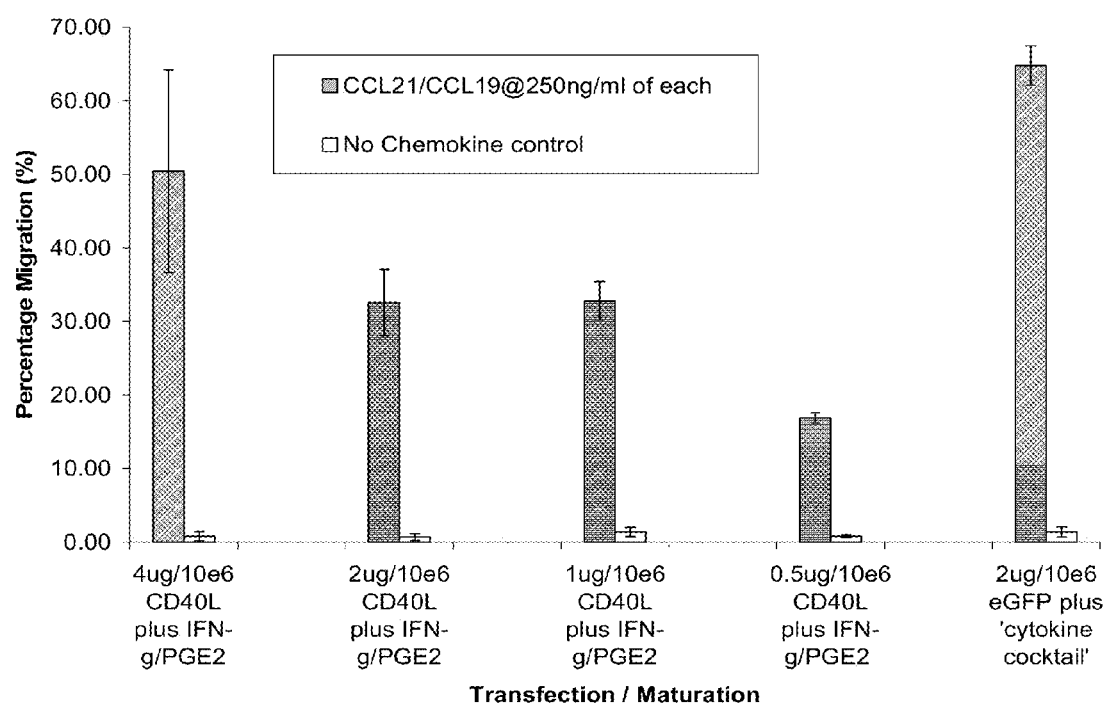
FIG. 8 shows that DCs transfected with CD40L mRNA and co-cultured with IFN-γ require the presence of $PGE_2$ to enable chemokine dependent migration. DCs were transfected with a titration of CD40L mRNA and immediately incubated with 1000 U/ml IFN-γ and 1 µg/ml $PGE_2$. DCs transfected with eGFP and matured with a cytokine cocktail containing $PGE_2$ represent a positive control. After 18 hrs of maturation, DCs from each culture condition were tested in "transwell" migration assays against the lymph node homing chemokines, CCL19 and 21. DC migration was proportional to the size of the CD40L mRNA payload.

In addition to the capacity to secrete IL-12p70 and exhibit a mature phenotype, typically defined as cells expressing elevated levels of co-stimulatory molecules such as CD80, CD83 and CD86 (see Table III), DCs must display the capacity to migrate, if they are going to be capable of homing to a lymph node in vivo. Several studies have shown that PGE$_2$ primes mature DCs for migration (Luft et al. (2002) Blood 100: 1362, Scandella et al. (2002) Blood 100: 1354). FIG. 8 shows that the inclusion of 1 μg/ml PGE$_2$, in addition to IFN-γ, enables the maturing DCs to migrate, and that the acquisition of this migratory potential is proportional to the CD40L mRNA payload. Thus, CD40L contributes to not only the maturing DC phenotype, and dominant IL-12p70 profile (see Table II), but also to priming for migration. By contrast, DCs matured by transfection with CD40L mRNA and cultured in the presence of IFN-γ, but in the absence of PGE$_2$, fail to migrate (data not shown), despite displaying significant cell surface expression of the chemokine receptor, CCR7.

maturation for a further 24 hrs. DCs were again harvested, and the cells stained for various cell surface markers, particularly those associated with increased function, namely co-stimulation and migration. Supernatants from the maturation cultures were collected and subjected to IL-12p70 and IL-10 cytokine analysis.

(a) DCs were transfected with 2 μg per million cells with flu mRNA as antigen-encoding payload, in addition to 4 μg per million cells eGFP mRNA. eGFP mRNA allows for confirmation of transfection by FACS, and to act as a substitute control for the 4 ug per million cells CD40L mRNA maturation payload, in the alternate process. These flu/eGFP transfected DCs were matured in the presence of the "cytokine cocktail".

(b) DCs were transfected with 2 μg per million cells with MART-APL mRNA as antigen-encoding payload, and subjected to maturation with the "cytokine cocktail".

(c) DCs were transfected with 2 μg per million cells with flu mRNA as antigen-encoding payload, concomitant with 4 μg per million cells CD40L mRNA as the maturation payload. These cells were immediately placed in culture with IFN-γ and PGE$_2$ as described in materials and methods.

(d) DCs were transfected with 2 μg per million cells with MART-APL as antigen-encoding payload, concomitant with 4 μg per million cells CD40L mRNA as the maturation payload. These cells were immediately placed in culture with IFN-γ and PGE$_2$ as described in materials and methods.

(e) IL-12p70 secretion from DCs undergoing maturation.

(f) IL-10 secretion from DCs undergoing maturation.

DCs Sequentially Matured Via Transfection with CD40L mRNA and IFN-γ/PGE$_2$ Invoke Potent T-Cell Recall Responses.

To determine the "immunopotency" of DCs matured via CD40L mRNA transfection and IFN-γ/PGE$_2$, DCs were co-transfected with 2 μg mRNA encoding flu matrix protein per million DCs in addition to the CD40L mRNA and IFN-γ/PGE$_2$ culture environment. 18 hrs post transfection, DCs were harvested, washed, and co-cultured with autolo-

TABLE III

Phenotypic analysis and secreted cytokine profile of DCs undergoing maturation induced by either 'Cytokine Cocktail', or CD40L plus IFN-γ and PGE$_2$

| DC markers | Immature DC | (a) Flu/eGFP mRNA Cytokine Cocktail | (b) Mart-APL mRNA Cytokine Cocktail | (c) Flu/CD40L mRNA IFN-g/PGE$_2$ | (d) Mart-APL/CD40L mRNA IFN-g/PGE$_2$ |
|---|---|---|---|---|---|
| HLA-ABC | 99.7% | 98.6% | 99.5% | 99.9% | 99.9% |
| HLA-DR | 95.0% | 99.6% | 99.7% | 99.8% | 99.5% |
| CD83 | 23.2% | 98.3% | 99.2% | 99.6% | 99.3% |
| CD14 | 0.3% | 1.7% | 2.9% | 3.2% | 4.9% |
| CD56 | 2.8% | 3.3% | 3.2% | 2.8% | 2.1% |
| CD19 | 1.8% | 1.1% | 2.1% | 3.2% | 3.2% |
| CD3 | 2.8% | 2.4% | 3.1% | 2.8% | 3.1% |
| CD86 | 59.3% | 99.7% | 100.0% | 100.0% | 100.0% |
| CD80 | 28.8% | 99.0% | 99.5% | 99.2% | 99.5% |
| CD1a | 51.6% | 49.1% | 52.2% | 48.6% | 49.9% |
| CD209 | 95.8% | 95.5% | 96.1% | 96.4% | 95.9% |
| CCR7 | 3.2% | 47.4% | 35.5% | 35.4% | 36.2% |
| (e) IL-12 (pg/ml) | N/A | 27.5 | 59.0 | 1456.3 | 1350.0 |
| (f) IL-10 (pg/ml) | N/A | 948.8 | 810.0 | 187.7 | 165.5 |

Figure 9:
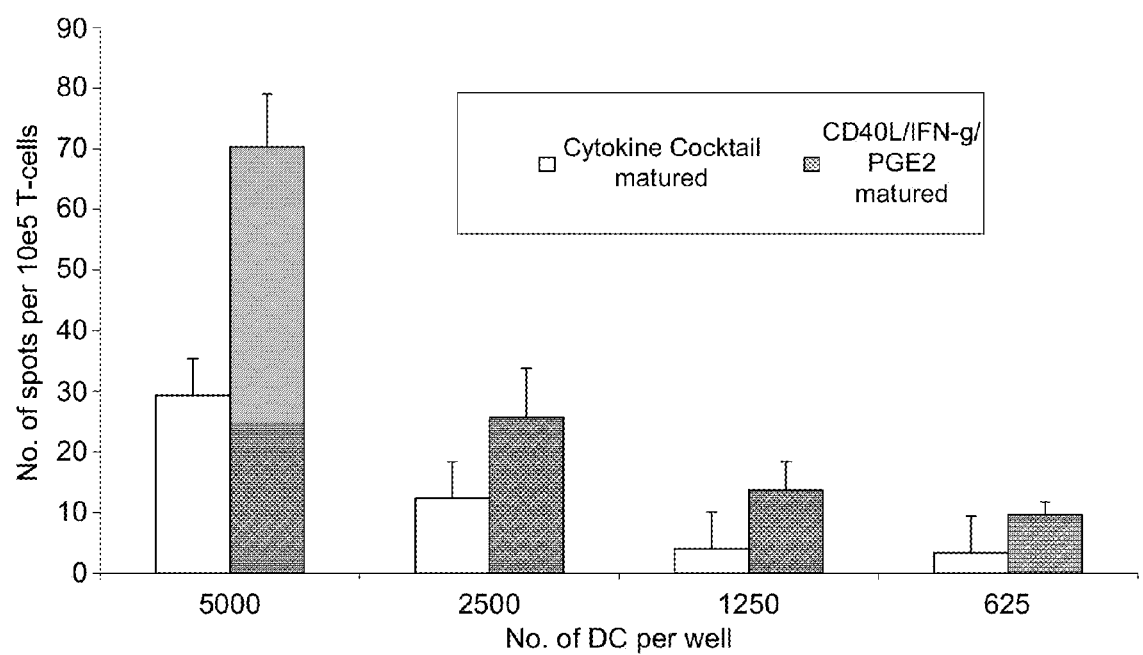
FIG. 9 shows that DCs matured via transfection with CD40L mRNA and cultured in the presence of IFN-γ and $PGE_2$ invoke efficient T-cell "recall responses" when compared to DCs matured in the presence of the "cytokine cocktail". DCs were co-transfected with 2 µg flu M1 mRNA per million cells as antigen payload, and 4 µg eGFP mRNA control, and subsequently matured with cytokine cocktail. Alternatively, DCs were co-transfected with 2 µg flu M1 mRNA per million cells as antigen payload, and 4 µg CD40L mRNA as the maturation payload. These latter cells were immediately cultured in 1000 U/ml IFN-γ and 1 µg/ml $PGE_2$ to complete the maturation process. After 24 hrs, each DC population was used in ELISpot assays to recruit an anti-flu M1 recall responses, as determined by the frequency of responding T-cells secreting IFN-γ. DCs matured by transfection with CD40L mRNA in the presence of IFN-γ and $PGE_2$ invoked a more potent anti-flu response.

DCs were prepared from adherent monocytes and cultured for 6 days in GM-CSF/IL-4. On harvesting, DCs were transfected with various mRNA payloads and subjected to gous T-cells in IFN-γ ELISpot assays. FIG. 9 shows that DCs matured via CD40L/IFN-γ/PGE$_2$ display increased immunopotency, compared to DCs transfected with flu mRNA and matured with 'cytokine cocktail', as defined by the frequency of flu-specific IFN-γ spots in the assay.

DCs Sequentially Matured Via Transfection with CD40L mRNA and IFN-γ/PGE$_2$ Invoke Primary Responses.

Figure 10:
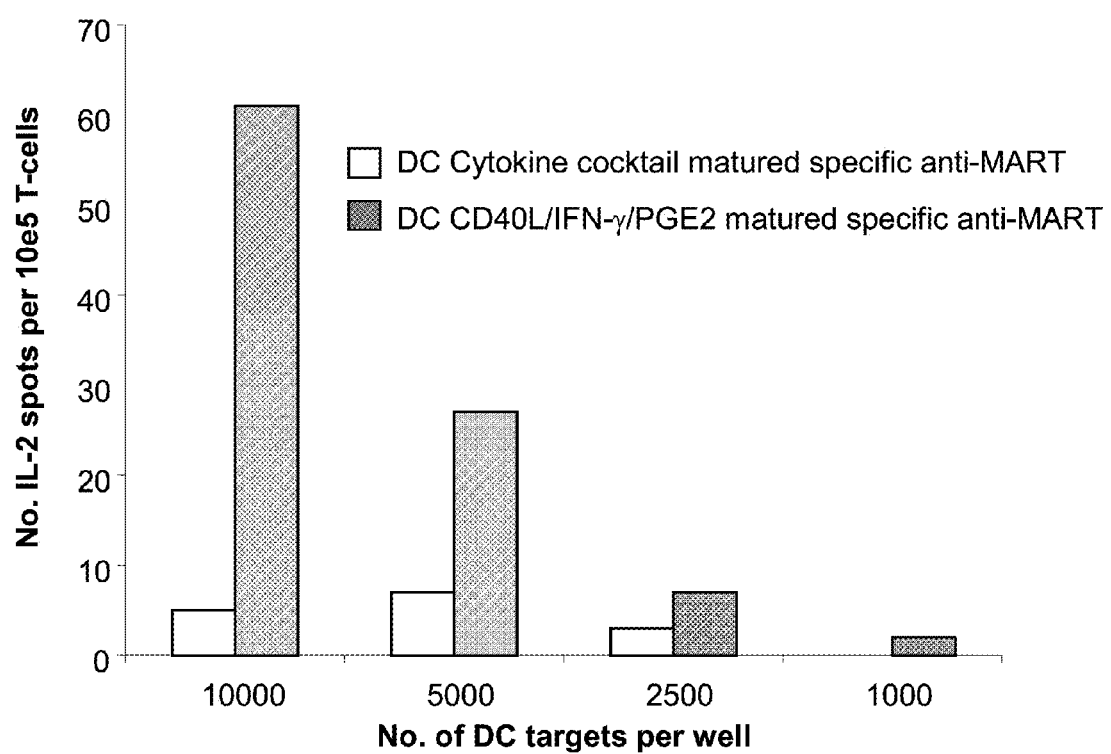
FIG. 10 shows that DCs matured via transfection with CD40L mRNA and cultured in the presence of IFN-γ and $PGE_2$ invoke efficient "primary T-cell responses" when compared to DCs matured in the presence of the "cytokine cocktail". DCs were transfected with 2 µg MART-APL mRNA per million cells as antigen payload, and subsequently matured with cytokine cocktail. Alternatively, DCs were co-transfected with 2 µg MART-APL mRNA per million cells as antigen payload, and 4 µg CD40L mRNA as the maturation payload. These latter cells were immediately cultured in 1000 U/ml IFN-γ and 1 µg/ml $PGE_2$ to complete the maturation process. After 24 hrs, each DC population was used to raise T-cell responses to MART-APL peptide sequences, generated from the transfected MART-APL mRNA payload, by co-culture of autologous naive CD8+ T-cells for 7 days in the presence of 0.2 U/ml of IL-2. After this first round of stimulation, T-cells were harvested and established in IL-2 ELISpot assays, restimulated with the appropriately matured, antigen loaded DCs. DCs matured by transfection with CD40L mRNA in the presence of IFN-γ and $PGE_2$ invoked a more potent anti-MART-APL response as determined by the frequency of responder CD8+ Tcells secreting IL-2.
Figure 11A:
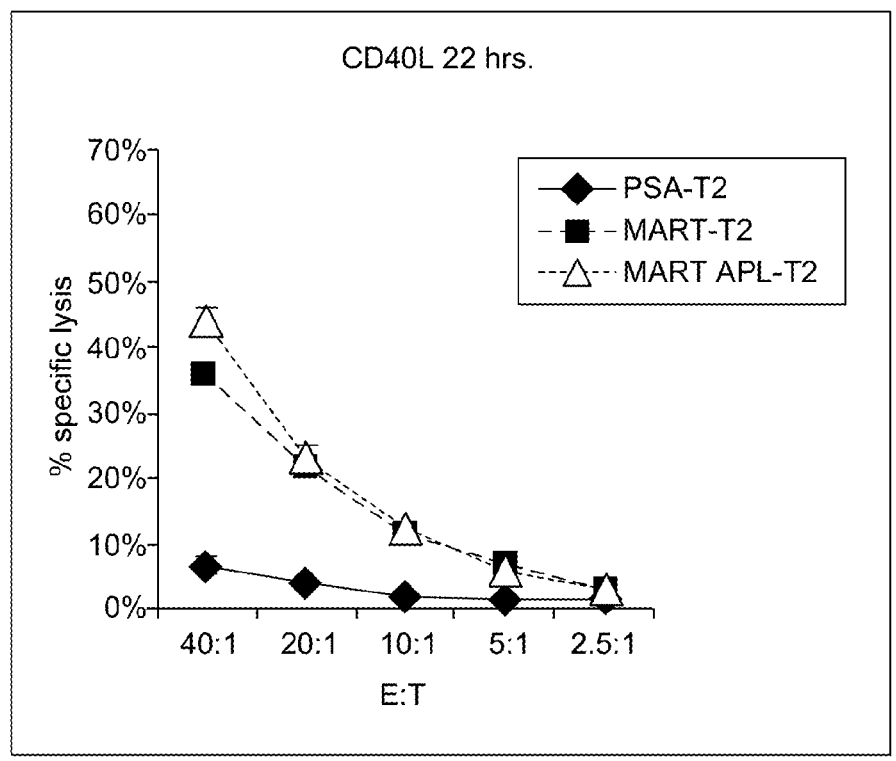
FIGS. 11A and 11B show the induction of cytotoxic T-cells by DCs expressing MART-APL mRNA.
Figure 11B:
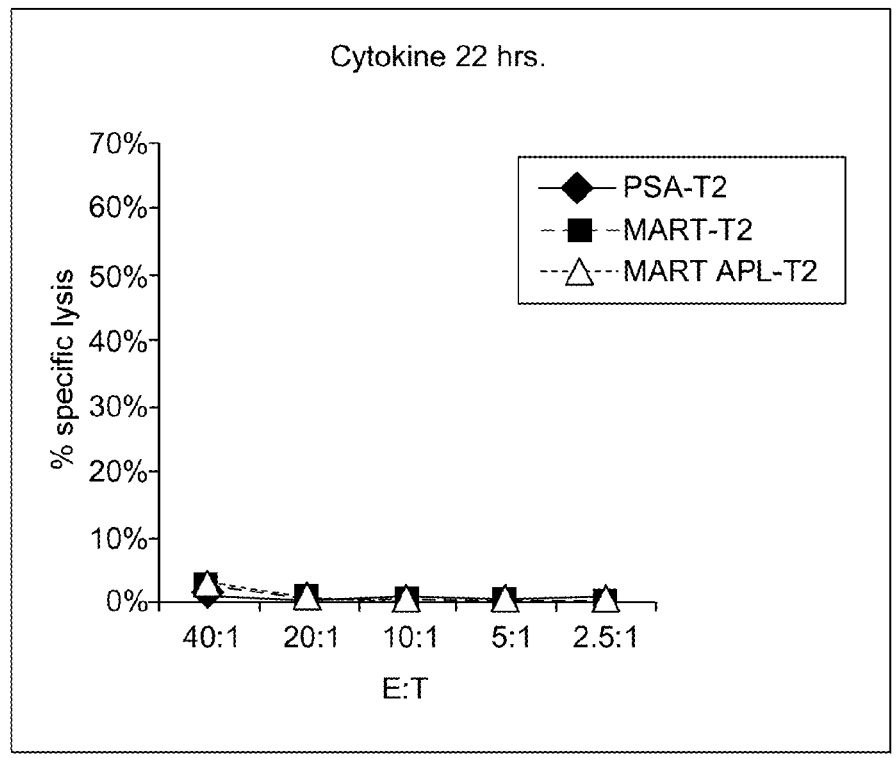

Recall responses, such as that described in FIG. 9, are less dependent on the presence of DCs expressing optimized co-stimulatory molecules and supporting cytokine environments. Therefore, DCs were tested for their ability to invoke primary immune responses to the melanoma associate antigen, MART-1, to which many healthy donors maintain a high naive T-cell precursor frequency. As HLA-A201 donors were preferentially used, DCs were transfected with an mRNA encoding MART-1 in which the A2 restricted determinant was optimized by mutation of the mRNA sequence by site directed mutagenesis, such that the alanine at position 27 was substituted by leucine, and here referred to as MART-APL (Valmori, D et al (1998) J. Immunol. 160: 1750). DCs co-transfected with 2 μg MART-APL mRNA with 4 μg CD40L mRNA and immediately pulsed with IFN-γ/PGE$_2$ for 18 hrs were compared to DCs loaded solely with MART-APL, and matured overnight with the "cytokine cocktail". Antigen-loaded and matured DCs were added to purified autologous CD8$^+$ T-cells, and cultured for 7 days in the presence of 0.2 U/ml human IL-2. After this period, T-cells were recovered and co-cultured with a second round of antigen-loaded DC stimulators as appropriate in an IL-2 ELISpot assay. FIG. 10 shows that CD8+ T-cells cultured in the presence of DCs matured via CD40L and IFN-γ/PGE$_2$ results in a highly significant increase in T-cells capable of IL-2 secretion in a specific response to the optimized MART-APL epitope originally encoded within the MART-APL mRNA sequence. In conclusion, DCs exposed to sequential maturation via IFN-γ/PGE$_2$ and CD40L are significantly more potent at raising primary immune responses than DCs matured with the currently accepted standard "cytokine cocktail". Moreover, FIG. 11 shows that CTLs generated with MART-APL loaded DCs matured with the 'cytokine cocktail' fail to mediate CD4-independent CD8-mediated cytotoxicity against T2 cells pulsed with the appropriate HLA-A2 restricted MART-APL peptide (FIG. 11b). By contrast, CTLs generated on CD40L/IFN-γ/PGE$_2$ matured DCs are fully active, and kill the MART-APL peptide pulsed T2 targets (FIG. 11a).

Phenotypic Analysis of Immature DCs Maturing Under the PME-CD40L Process

DCs were matured on Day 5 with the PME-CD40L process described herein. Specifically monocytes were cultured in medium GM-CSF and IL-4 for 5 days to produce immature CD83$^-$ DCs. On day 5, the immature DCs were fed with medium containing TNFα, IFNγ and PGE$_2$ (TIP). On day 6, the post TIP phenotype was determined (see Table IV). As shown in Table IV, the majority of cells were positive for CD80, CD83, CD86 and CD209. These DCs were also CCR7 negative (data not shown). The low percentage of CD14$^+$ cells represent monocytes that did not differentiate into dendritic cells. On day 6, the CD83$^+$ CCR7$^-$ DCs were co-transfected (via electroporation) with 1 μg mRNA prepared from amplified renal cell carcinoma RNA and 4 μg CD40L mRNA per million cells. CD40L expression was measured at 4 hours post transfection. The cells were 77 preserved in liquid nitrogen at 4 hrs post transfection. The post thaw recovery and viability were measured immediately after thawing, and at 24 hours post thawing. As can be seen, at 24 hours post thaw, the majority of DCs became CCR7+. The CCR7+ DCs were also positive for CD80, CD83 and CD86. The results of 3 separate runs are shown in Table IV.

TABLE IV

| Run data | Run 1 | Run 2 | Run 3 |
| --- | --- | --- | --- |
| Seeding density per flask | 200 × 10$^6$ | 200 × 10$^6$ | 200 × 10$^6$ |
| Number of flasks seeded | 18 | 20 | 20 |
| Post TIP Recovery (%) | 8 | 24 | 15 |
| Post TIP Viability (%) | 97 | 95 | 93 |
| Number of cuvettes | 14 | 15 (limited) | 15 (limited) |
| 4 hr post electroporation Recovery (%) | 64 | 43 | 73 |
| 4 hr post electroporation Viability (%) | 91 | 89 | 85 |
| Number of vaccine doses from Run | 13 | 9 | 15 |
| Post thaw Recovery (%) | 86 | 94 | 85 |
| Post thaw Viability (%) | 88 | 88 | 78 |
| Predicted doses per 30 flasks | 21 | 28 | 30 |
| 4 hr CD40L expression | 84 | 76 | 49 |
| Post TIP DC phenotype | | | |
| % CD14 | 0.8 | 0.5 | 12 |
| % CD80 | 100 | 100 | 98 |
| % CD83 | 99 | 92 | 82 |
| % CD86 | 100 | 100 | 100 |
| % CD209 | 98 | 99 | 100 |
| mDC phenotype (post thaw) | | | |
| % CD14 | 3 | 0.3 | 1.4 |
| % CD80 | 99 | 100 | 100 |
| % CD83 | 100 | 100 | 98 |
| % CD86 | 100 | 100 | 100 |
| % CD209 | 98 | 100 | 100 |
| % CCR7 | 53 | 12 | 32 |
| 24 hr post thaw % CCR7 | 93 | 93 | 95 |
| 24 hr post thaw 'washout' | | | |
| % viability | 50 | 67 | 63 |
| % recovery | 36 | 46 | 73 |
| 24 hr post thaw transwell migration | | | |
| % Migration - media control | 1.1 | 0.78 | 1.2 |
| % Migration - 100 ng/ml CCL19 and 21 | 74 | 107 | 70 |

DCs Matured Via the PME-CD40L Process are Highly Migratory in Response to Lymph Node Homing Chemokines, CCL19 and 21.

Figure 12:
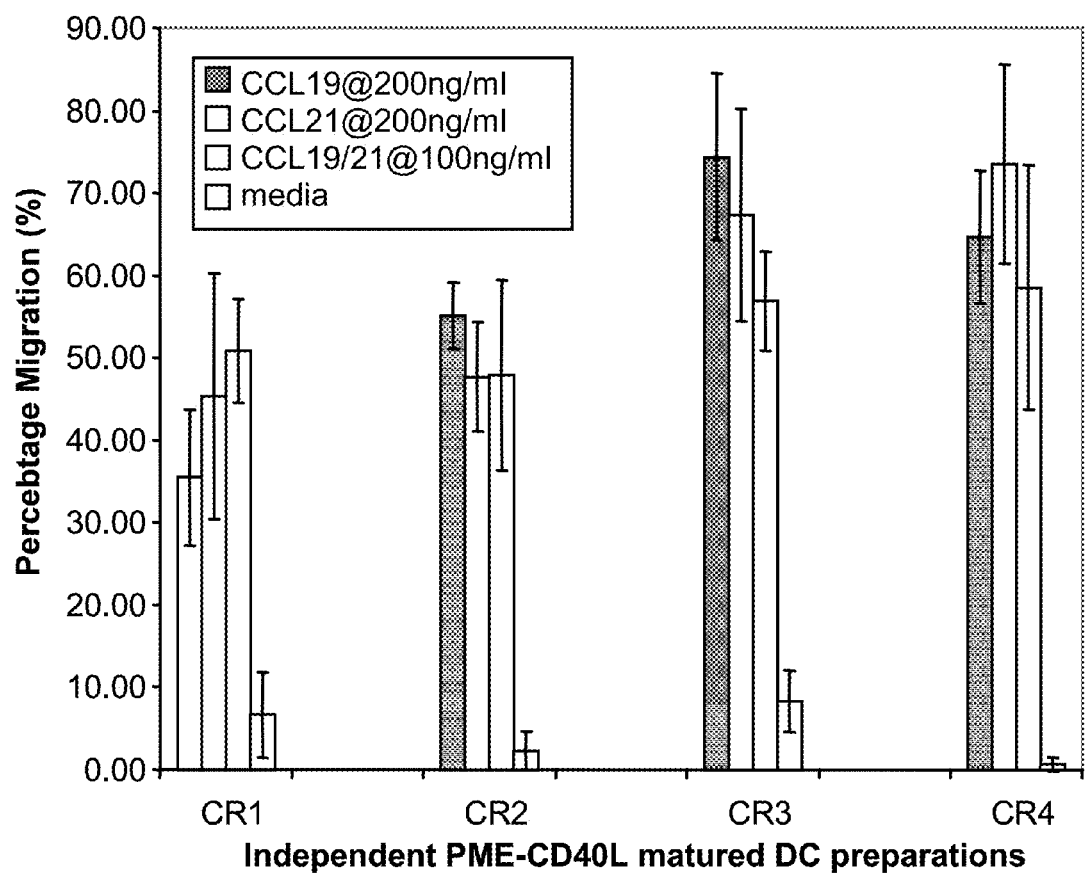
FIG. 12 shows the migratory capacity of PME-CD40L matured DCs in transwell assays to the lymph node chemokines, CCL19 and 21. Four independent healthy donors were tested in parallel, with each DC preparation being transfected with 1 ug amplified total RCC tumor RNA, along with 4 ug CD40L RNA per million DCs. Migration assays were set up 24 hrs post transfection with the mRNA payloads.

PME-CD40L matured DCs were assayed for migration in response to chemokines, CCL19 and 21, twenty-four hours after co-transfection with total amplified RCC RNA and CD40L RNA. FIG. 12 shows that using four independent donors, that PME-CD40L matured DCs are highly migratory, consistent with the very high level of CCR7 expression achieved 24 hrs post electroporation with the PME-CD40L process (see Table IV).

DCs Matured Via the PME-CD40L Process Show Significantly Enhanced Immunopotency Over DCs Matured with the 'CD40L Base Process'.

Figure 13:
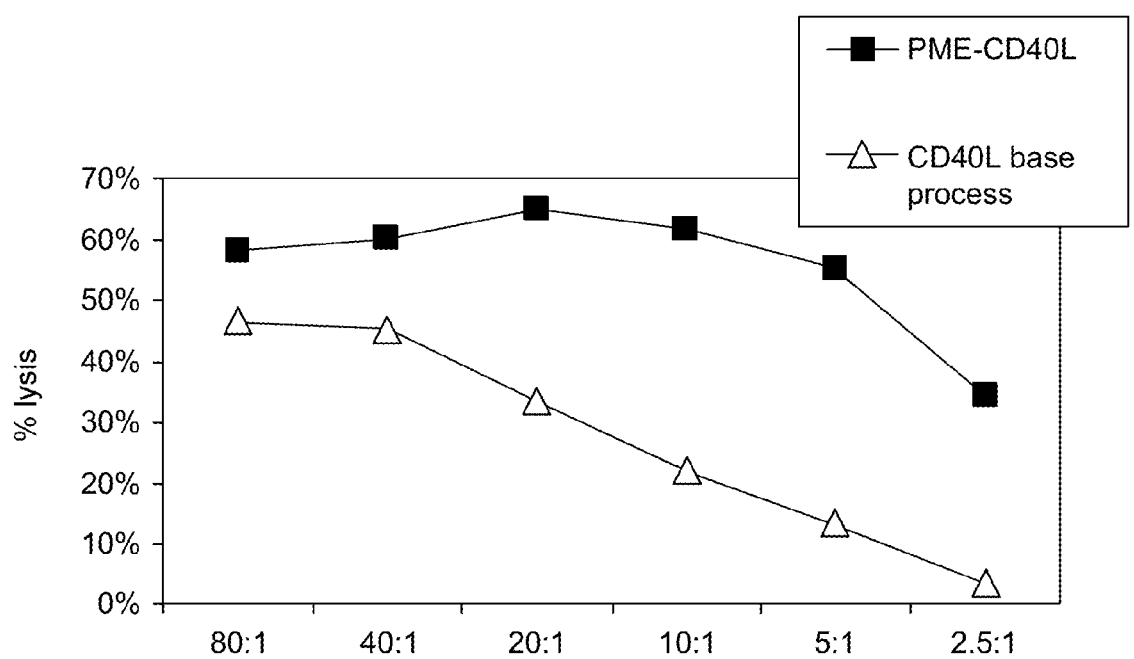
FIG. 13 shows the induction of CTL responses from a healthy donor to the melanoma-associated antigen, MART-1. DCs were prepared and loaded with MART-1 RNA and matured via the 'CD40L base process' or DCs were prepared using the PME-CD40L process. DCs and purified CD8 T-cells were co-cultured in a 1:10 ratio, undergoing three rounds of stimulation in the presence of IL-2. The data shows $^{51}$CR release cytotoxic assays using MART-1 peptide pulsed T2 target cells across a range of effector-target ratios.
Figure 14:
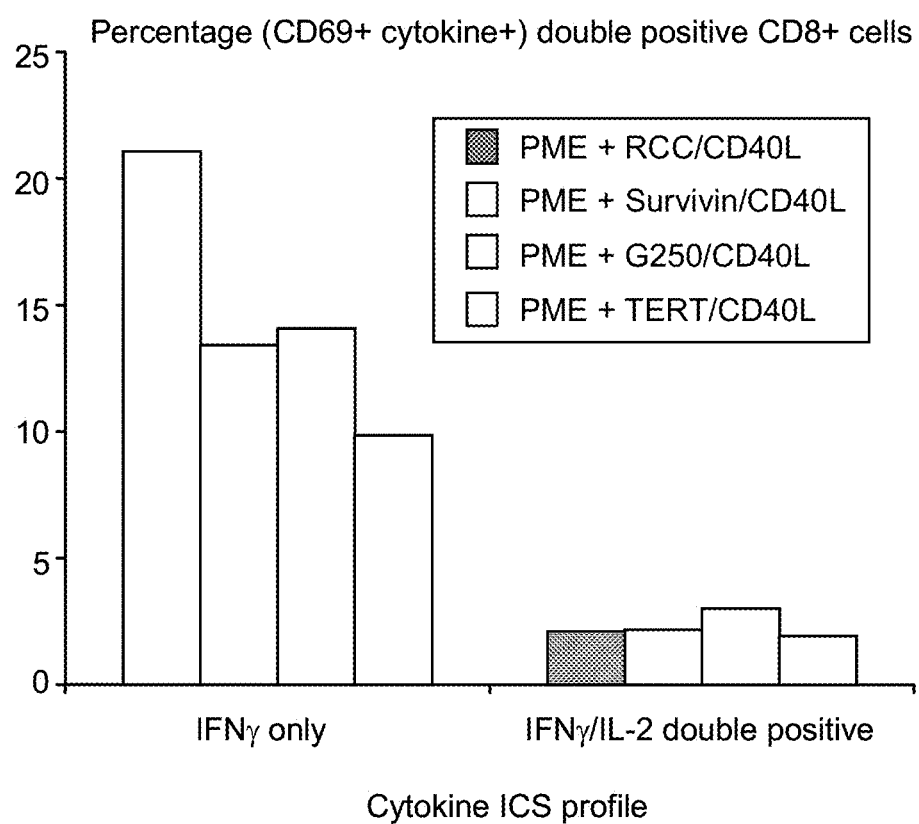
FIG. 14 shows the induction of a fully autologous CTL response to DCs loaded with total amplified RCC tumor RNA, PME-CD40L matured DCs. DCs and purified CD8 T-cells were co-cultured in a 1:10 ratio, undergoing three rounds of stimulation in the presence of IL-2. 5 days after the last stimulation, CD8 T-cells were restimulated with DCs transfected with: total amplified RCC RNA, hTERT RNA, Survivin RNA, G250 RNA or negative control DCs transfected with eGFP RNA. The data is derived from identifying responder T-cells by cell surface staining for the activation marker, CD69, and simultaneously detection of intracellular IFN-γ and IL-2. Intracellular cytokine responses were subdivided to identify IFN-γ single positive (effector cells) from IFN-γ/IL-2 double positive (memory cells).

Despite the induction of primary immune responses by the 'CD40L base process', the 'post maturation electroporation-CD40L' process, whereby DCs are first matured with TNF-α, IFN-γ and PGE$_2$, prior to electroporation with CD40L plus antigen-encoding mRNA, results in a significant improvement in CTL activity using the MART antigen model system. (FIG. 13). In addition, the PME-CD40L process was tested for the induction of IFN-γ and IL-2 responses using fully autologous materials derived from a renal cell carcinoma patient: patient DCs were prepared as described above for the PME-CD40L process, and electroporated with autologous total amplified RCC tumor RNA. The antigen loaded DCs were cultured with autologous patient CD8 T-cells, and the resulting responder CTL were studied by intracellular cytokine staining in response to the eliciting DC, and to individual DCs transfected with the tumor-associated antigens, hTERT, Survivin and the RCC specific antigen, G250. DCs transfected with eGFP encoding mRNA were used as negative control stimulators. FIG. 14 shows that patient T-cells responded to the total amplified RCC RNA loaded DCs, and also to the three tumor-associated antigens, with both IFN-γ and IL-2 frequencies higher than that induced by the eGFP mRNA transfected negative control. (Response to eGFP subtracted from total response to each RCC associated DC target)

DCs Matured by the 'Base CD40L Process' and Pulsed with KRN7000 can Recruit NKT-Cells which Enhance the Induction of Primary CTLs.

Figure 15A:
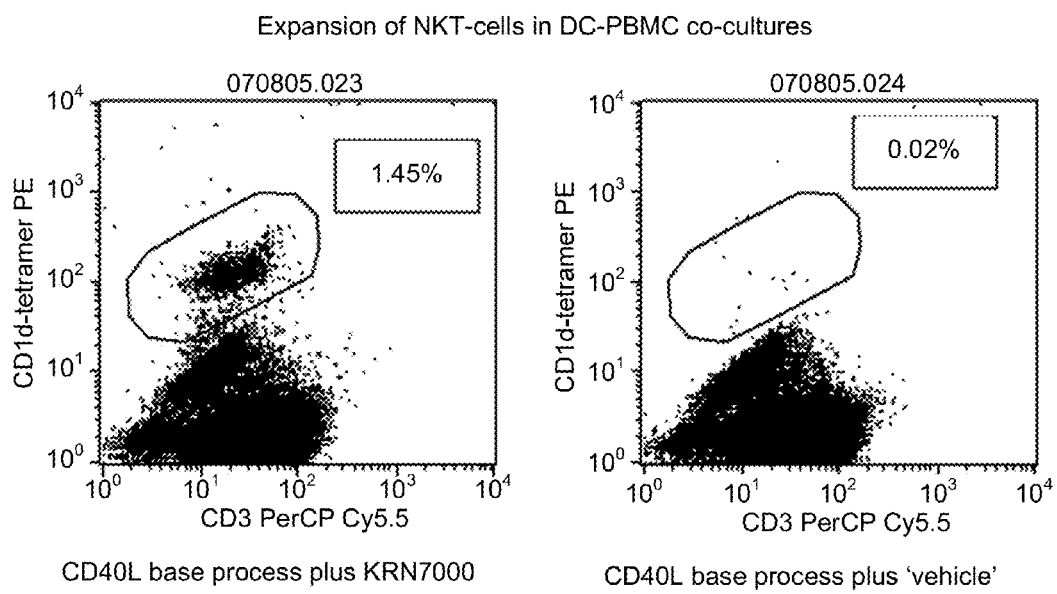
FIGS. 15A and 15B show the effect of MART-1 RNA transfected CD40L base process matured DCs pulsed with KRN7000 or vehicle on the expansion of NKT cells (FIG. 15A) and MART-1-reactive CTLs (FIG. 15B). The data clearly shows that KRN7000 pulsed DC can expand NKT-cells as defined by CD1d/KRN7000 tetramer staining, and that the presence of an expanded population of NKT-cells can increase the concomitant recruitment of primary CTLs to MART-1, as defined by tetramer staining with MART-1/HLA-A2 tetramers.
Figure 15B:
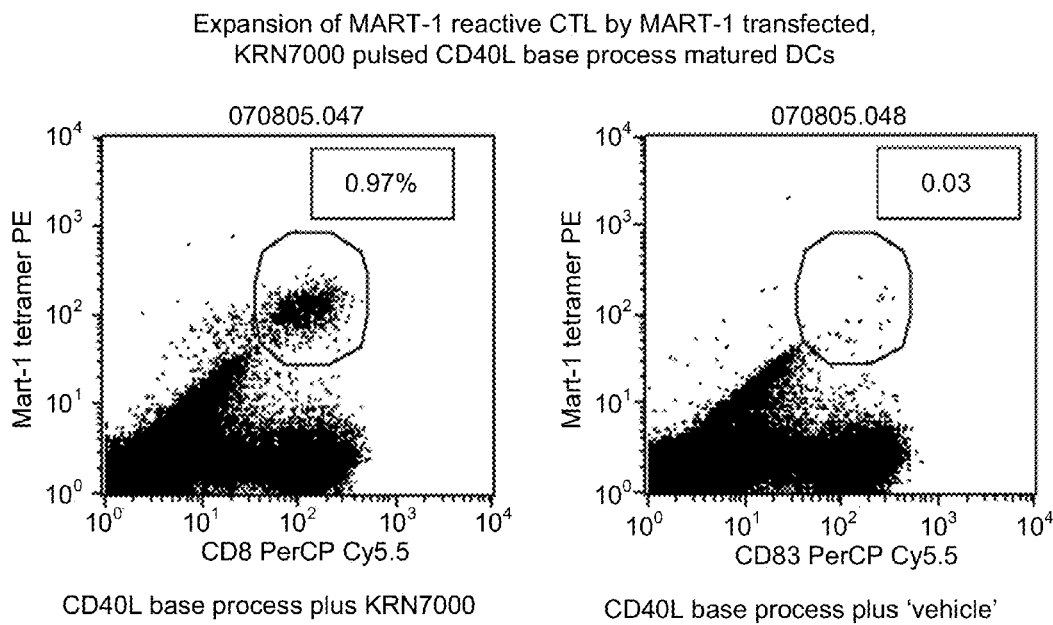

MART-1 mRNA-loaded, CD40L base process matured DC, pulsed with KRN7000, increase the frequency of NKT-cells in PBMC cultures versus the same mature RNA loaded DCs pulsed with vehicle in place of KRN7000, as defined by CD1d/KRN7000-tetramer staining (FIG. 15a). Using tetramer analysis for responder CTL (MART-1/HLA-A2), the presence of KRN7000 pulsed onto MART-1 mRNA transfected DC significantly increases the frequency of MART reactive T-cells (FIG. 15b). Thus, the expansion of NKT-cells in the PBMC cultures provides an amplification loop, probably achieved by NKT-cell derived 'help', that can support primary CD8 CTL development.

Optimization of CD40L mRNA

The CD40L RNA used in the original DC experiments demonstrating a preferred way of maturation was transcribed from plasmid template pCR2.1 CD40L WT. The preferred CD40L RNA contains an ARCA cap analog and polyA tail. The plasmid pCR2.1 CD40L WT was modified by removal of an XbaI-EcoRV fragment located 5' of the initiator ATG codon. The fragment encompassed 32 nucleotides of vector sequence and contained three cryptic potential initiator ATG codons. The rationale for this modification was that these additional ATG's might interfere with efficient initiation of CD40L translation by competing with the accurate CD40L translation initiation site. Coding sequence of the CD40L remained unaffected by these modifications. CD40L RNA transcribed from the modified plasmid template performed better than the current CD40L reference standard in two independent DC transfection experiments as measured by induction of IL-12 expression. The modified plasmid is referred to as pCR2.1 CD40L WT Delta X-E.

Figure 18:
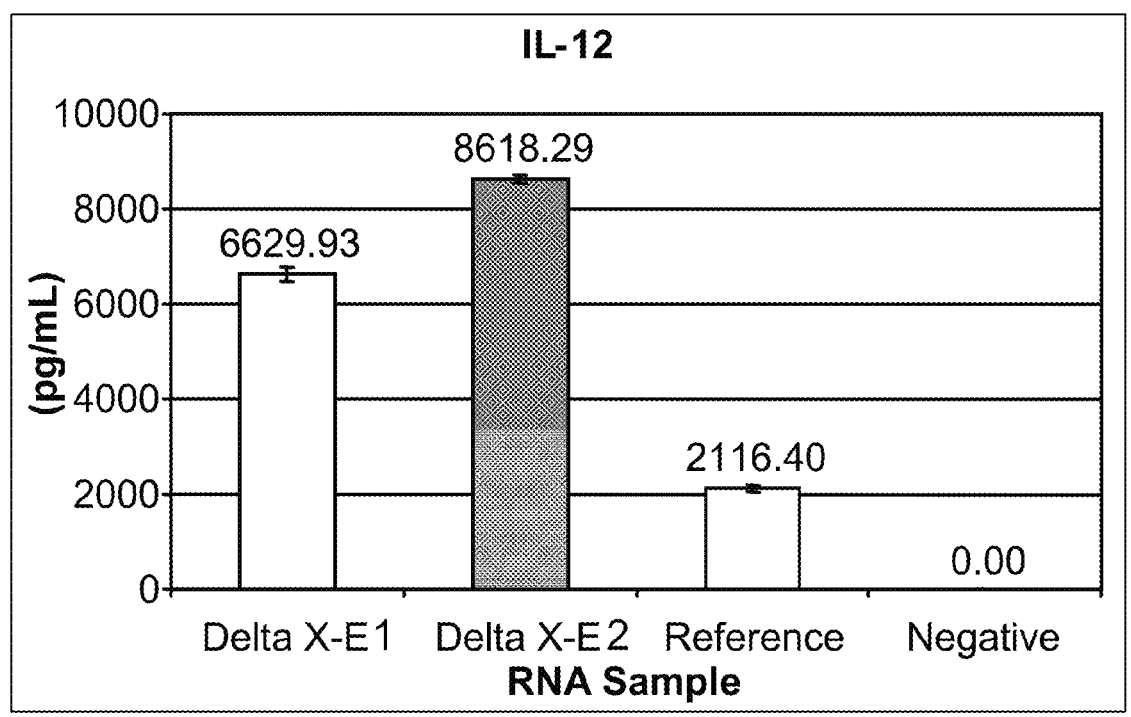
FIG. 18 shows the level of IL-12 expression by DC transfected with mRNA transcribed from pCR2.1 CD40L WT Delta X-E plasmid in 100 ug scale (Delta X-E1) or 1 mg scale (Delta X-E2) transcription reactions using mMessage mMachine T7 Ultra kit (Ambion). Reference RNA was transcribed from plasmid pCR2.1 CD40L WT. The transcribed CD40L RNAs were modified by addition of polyA tail using polyA plus kit (Epicentre). RNAs were transfected into DCs. Approximately 20 hrs post transfection the amount of IL-12 was measured in the supernatant of the matured DCs using Elisa. Negative: IL-12 expression measure in supernatant of DCs electroporated without any CD40L RNA.

In addition we wished to determine whether expression of the CD40L RNA can be further optimized by placing the CD40L 5' untranslated region directly upstream of the CD40L initiator codon. The pCR2.1 CD40L WT Delta X-E plasmid was further modified by the insertion of 39 bp CD40L 5' untranslated sequence located immediately upstream of the CD40L translation start site. RNA transcribed from this plasmid did not perform as well as the RNA described from CD40L WT Delta X-E but rather, performed similarly to the current CD40L transcribed from pCR2.1 CD40L WT (FIG. 18). Therefore the pCR2.1 CD40L WT Delta X-E plasmid is the preferred plasmid. The DNA sequence corresponding to the CD40L RNA transcribed from the pCR2.1 CD40L WT Delta X-E plasmid is shown in SEQ ID NO:11. The ATG start codon begins at position 41.

What is claimed is:

1. A method for preparing CD83$^+$ CCR7$^+$ mature dendritic cells mDCs), comprising the sequential steps of:
   (a) culturing isolated immature dendritic cells (iDCs) in culture medium comprising an interferon gamma receptor (IFN-γR) agonist and a TNF-αR agonist to produce CD83$^+$ mDCs; and
   (b) cotransfecting said CD83$^+$ mDCs with mRNA encoding CD40L polypeptide and mRNA encoding an antigen approximately 12 to 30 hours after initiating step (a) to produce CD83$^+$ CCR7$^+$ mDCs; wherein the CD40L polypeptide comprises amino acid residues:
      (i) 51 through 261 of SEQ ID NO: 2, or
      (ii) 120 through 261 of SEQ ID NO: 2.

2. The method of claim 1, wherein said culture medium further comprises PGE$_2$.

3. The method of claim 1, wherein said CD83$^+$ mDCs are cotransfected using electroporation.

4. The method of claim 1, wherein said iDCs are generated by contacting isolated human monocytes with GM-CSF and at least one of IL-4 or IL-13.

5. The method of claim 1, wherein said iDCs are prepared from CD34$^+$ hematopoietic stem or progenitor cells.

6. The method of claim 1, wherein said IFN-γR agonist is IFN-γ.

7. The method of claim 1, wherein said TNF-αR agonist is TNF-α.

8. The method of claim 1, wherein said culturing is in the absence of an effective amount of IL-1β and IL-6.

9. The method of claim 6, wherein said IFN-γ comprises a polypeptide having at least 95% sequence identity with SEQ ID NO:6.

10. The method of claim 6, wherein said IFN-γ comprises the sequence of SEQ ID NO:6.

11. The method of claim 1, wherein said mRNA encoding said CD40L polypeptide is in vitro translated mRNA.

12. The method of claim 1, wherein said mRNA encoding an antigen is in vitro translated mRNA.

13. The method of claim 1, wherein said mRNA encoding said CD40L polypeptide and the mRNA encoding said antigen are in vitro translated mRNAs.

14. A method for preparing CD83$^+$ CCR7$^+$ mature dendritic cells (mDCs), comprising the sequential steps of:
   (a) culturing isolated immature dendritic cells (iDCs) in culture medium comprising an interferon gamma receptor (IFN-γR) agonist and a TNF-αR agonist to produce CD83$^+$ mDCs; and
   (b) cotransfecting said CD83$^+$ mDCs with mRNA encoding a CD40L polypeptide and mRNA encoding an antigen approximately 12 to 30 after initiating step (a) to produce CD83$^+$ CCR7$^+$ mDCs, wherein said mRNA encoding said CD40L polypeptide comprises:
      (i) a polynucleotide comprising nucleotides 190 to 822 of SEQ ID NO:1, or (ii) a polynucleotide comprising nucleotides 397 to 822 of SEQ ID NO:1.

15. The method of claim 1, further comprising cryopreserving said cotransfected CD83$^+$ CCR7$^+$ mDCs.

16. The method of claim 15, wherein said CD83$^+$ CCR7$^+$ mDCs are cryopreserved 4 hours post cotransfection.

17. The method of claim 1, wherein said isolated iDCs are cultured for approximately 12 to 30 hours.

18. The method of claim 1, wherein said mRNA encodes CD40L polypeptide consisting of amino acid residues 51 through 261 of SEQ ID NO: 2.

19. The method of claim 1, wherein said mRNA encodes CD40L polypeptide consisting of amino acid residues 120 through 261 of SEQ ID NO: 2.

* * * * *

SEQUENCE LISTING

```
<160> NUMBER OF SEQ ID NOS: 26

<210> SEQ ID NO 1
<211> LENGTH: 1816
<212> TYPE: DNA
<213> ORGANISM: Homo sapiens
<220> FEATURE:
<221> NAME/KEY: CDS
<222> LOCATION: (40)..(825)

<400> SEQUENCE: 1
cttctctgcc agaagatacc atttcaactt taacacagc atg atc gaa aca tac        54
                                            Met Ile Glu Thr Tyr
                                             1               5 aac caa act tct ccc cga tct gcg gcc act gga ctg ccc atc agc atg     102
Asn Gln Thr Ser Pro Arg Ser Ala Ala Thr Gly Leu Pro Ile Ser Met
             10                  15                  20 aaa att ttt atg tat tta ctt act gtt ttt ctt atc acc cag atg att    150
Lys Ile Phe Met Tyr Leu Leu Thr Val Phe Leu Ile Thr Gln Met Ile
         25                  30                  35 ggg tca gca ctt ttt gct gtg tat ctt cat aga agg ttg gac aag ata    198
Gly Ser Ala Leu Phe Ala Val Tyr Leu His Arg Arg Leu Asp Lys Ile
     40                  45                  50 gaa gat gaa agg aat ctt cat gaa gat ttt gta ttc atg aaa acg ata    246
Glu Asp Glu Arg Asn Leu His Glu Asp Phe Val Phe Met Lys Thr Ile
 55                  60                  65 cag aga tgc aac aca gga gaa aga tcc tta tcc tta ctg aac tgt gag    294
Gln Arg Cys Asn Thr Gly Glu Arg Ser Leu Ser Leu Leu Asn Cys Glu
 70                  75                  80                  85 gag att aaa agc cag ttt gaa ggc ttt gtg aag gat ata atg tta aac    342
Glu Ile Lys Ser Gln Phe Glu Gly Phe Val Lys Asp Ile Met Leu Asn
             90                  95                 100
```

| | | | | | | | | | | | | | | | | |
|---|---|---|---|---|---|---|---|---|---|---|---|---|---|---|---|---|
| aaa | gag | gag | acg | aag | aaa | gaa | aac | agc | ttt | gaa | atg | caa | aaa | ggt | gat | 390 |
| Lys | Glu | Glu | Thr | Lys | Lys | Glu | Asn | Ser | Phe | Glu | Met | Gln | Lys | Gly | Asp | |
| | | | 105 | | | | 110 | | | | 115 | | | | | |
| cag | aat | cct | caa | att | gcg | gca | cat | gtc | ata | agt | gag | gcc | agc | agt | aaa | 438 |
| Gln | Asn | Pro | Gln | Ile | Ala | Ala | His | Val | Ile | Ser | Glu | Ala | Ser | Ser | Lys | |
| | | 120 | | | | | 125 | | | | | 130 | | | | |
| aca | aca | tct | gtg | tta | cag | tgg | gct | gaa | aaa | gga | tac | tac | acc | atg | agc | 486 |
| Thr | Thr | Ser | Val | Leu | Gln | Trp | Ala | Glu | Lys | Gly | Tyr | Tyr | Thr | Met | Ser | |
| 135 | | | | | 140 | | | | | 145 | | | | | | |
| aac | aac | ttg | gta | acc | ctg | gaa | aat | ggg | aaa | cag | ctg | acc | gtt | aaa | aga | 534 |
| Asn | Asn | Leu | Val | Thr | Leu | Glu | Asn | Gly | Lys | Gln | Leu | Thr | Val | Lys | Arg | |
| 150 | | | | | 155 | | | | | 160 | | | | | 165 | |
| caa | gga | ctc | tat | tat | atc | tat | gcc | caa | gtc | acc | ttc | tgt | tcc | aat | cgg | 582 |
| Gln | Gly | Leu | Tyr | Tyr | Ile | Tyr | Ala | Gln | Val | Thr | Phe | Cys | Ser | Asn | Arg | |
| | | | | 170 | | | | | 175 | | | | | 180 | | |
| gaa | gct | tcg | agt | caa | gct | cca | ttt | ata | gcc | agc | ctc | tgc | cta | aag | tcc | 630 |
| Glu | Ala | Ser | Ser | Gln | Ala | Pro | Phe | Ile | Ala | Ser | Leu | Cys | Leu | Lys | Ser | |
| | | | 185 | | | | | 190 | | | | | 195 | | | |
| ccc | ggt | aga | ttc | gag | aga | atc | tta | ctc | aga | gct | gca | aat | acc | cac | agt | 678 |
| Pro | Gly | Arg | Phe | Glu | Arg | Ile | Leu | Leu | Arg | Ala | Ala | Asn | Thr | His | Ser | |
| | | 200 | | | | | 205 | | | | | 210 | | | | |
| tcc | gcc | aaa | cct | tgc | ggg | caa | caa | tcc | att | cac | ttg | gga | gga | gta | ttt | 726 |
| Ser | Ala | Lys | Pro | Cys | Gly | Gln | Gln | Ser | Ile | His | Leu | Gly | Gly | Val | Phe | |
| 215 | | | | | 220 | | | | | 225 | | | | | | |
| gaa | ttg | caa | cca | ggt | gct | tcg | gtg | ttt | gtc | aat | gtg | act | gat | cca | agc | 774 |
| Glu | Leu | Gln | Pro | Gly | Ala | Ser | Val | Phe | Val | Asn | Val | Thr | Asp | Pro | Ser | |
| 230 | | | | | 235 | | | | | 240 | | | | | 245 | |
| caa | gtg | agc | cat | ggc | act | ggc | ttc | acg | tcc | ttt | ggc | tta | ctc | aaa | ctc | 822 |
| Gln | Val | Ser | His | Gly | Thr | Gly | Phe | Thr | Ser | Phe | Gly | Leu | Leu | Lys | Leu | |
| | | | | 250 | | | | | 255 | | | | | 260 | | |

| | |
|---|---|
| tga acagtgtcac cttgcaggct gtggtggagc tgacgctggg agtcttcata | 875 |
| atacagcaca gcggttaagc ccaccccctg ttaactgcct atttataacc ctaggatcct | 935 |
| ccttatggag aactatttat tatacactcc aaggcatgta gaactgtaat aagtgaatta | 995 |
| caggtcacat gaaaccaaaa cgggccctgc tccataagag cttatatatc tgaagcagca | 1055 |
| accccactga tgcagacatc cagagagtcc tatgaaaaga caaggccatt atgcacaggt | 1115 |
| tgaattctga gtaaacagca gataacttgc caagttcagt tttgtttctt tgcgtgcagt | 1175 |
| gtctttccat ggataatgca tttgatttat cagtgaagat gcagaaggga aatggggagc | 1235 |
| ctcagctcac attcagttat ggttgactct gggttcctat ggccttgttg gagggggcca | 1295 |
| ggctctagaa cgtctaacac agtggagaac cgaaaccccc cccccccccc cgccaccct | 1355 |
| ctcggacagt tattcattct ctttcaatct ctctctctcc atctctctct ttcagtctct | 1415 |
| ctctctcaac ctctttcttc caatctctct ttctcaatct ctctgtttcc ctttgtcagt | 1475 |
| ctcttccctc ccccagtctc tcttctcaat cccccttctt aacacacaca cacacacaca | 1535 |
| cacacacaca cacacacaca cacacacaca cacacacaca cacacagagt caggccgttg | 1595 |
| ctagtcagtt ctcttctttc caccctgtcc ctatctctac cactatagat gagggtgagg | 1655 |
| agtagggagt gcagccctga gcctgcccac tcctcattac gaaatgactg tatttaaagg | 1715 |
| aaatctattg tatctacctg cagtctccat tgtttccaga gtgaacttgt aattatcttg | 1775 |
| ttatttattt tttgaataat aaagacctct taacattaaa a | 1816 |

<210> SEQ ID NO 2
<211> LENGTH: 261
<212> TYPE: PRT
<213> ORGANISM: Homo sapiens

<400> SEQUENCE: 2

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

<210> SEQ ID NO 3
<211> LENGTH: 1570
<212> TYPE: DNA
<213> ORGANISM: Homo sapiens
<220> FEATURE:
<221> NAME/KEY: CDS
<222> LOCATION: (67)..(522)

<400> SEQUENCE: 3

```
ggcaggggag tcagcagagg cctcgctcgg gcgcccagtg gtcctgccgc ctggtctcac    60 ctcgcc atg gtt cgt ctg cct ctg cag tgc gtc ctc tgg ggc tgc ttg      108
       Met Val Arg Leu Pro Leu Gln Cys Val Leu Trp Gly Cys Leu
       1               5                   10 ctg acc gct gtc cat cca gaa cca ccc act gca tgc aga gaa aaa cag    156
Leu Thr Ala Val His Pro Glu Pro Pro Thr Ala Cys Arg Glu Lys Gln
15                  20                  25                  30 tac cta ata aac agt cag tgc tgt tct ttg tgc cag cca gga cag aaa    204
Tyr Leu Ile Asn Ser Gln Cys Cys Ser Leu Cys Gln Pro Gly Gln Lys
                35                  40                  45
```

```
ctg gtg agt gac tgc aca gag ttc act gaa acg gaa tgc ctt cct tgc      252
Leu Val Ser Asp Cys Thr Glu Phe Thr Glu Thr Glu Cys Leu Pro Cys
         50                  55                  60 ggt gaa agc gaa ttc cta gac acc tgg aac aga gag aca cac ttc cac      300
Gly Glu Ser Glu Phe Leu Asp Thr Trp Asn Arg Glu Thr His Phe His
 65                  70                  75 cag cac aaa tac tgc gac ccc aac cta ggg ctt cgg gtc cag cag aag      348
Gln His Lys Tyr Cys Asp Pro Asn Leu Gly Leu Arg Val Gln Gln Lys
         80                  85                  90 ggc acc tca gaa aca gac acc atc tgc acc tgt gaa gaa ggc tgg cac      396
Gly Thr Ser Glu Thr Asp Thr Ile Cys Thr Cys Glu Glu Gly Trp His
 95                 100                 105                 110 tgt acg agt gag gcc tgt gag agc tgt gtc ctg cac cgc tca tgc tcg      444
Cys Thr Ser Glu Ala Cys Glu Ser Cys Val Leu His Arg Ser Cys Ser
                115                 120                 125 ccc ggc ttt ggg gtc aag cag att gac atc tgc cag cca cat ttc ccc      492
Pro Gly Phe Gly Val Lys Gln Ile Asp Ile Cys Gln Pro His Phe Pro
        130                 135                 140 aag gac cgc ggt ttg aac ctt ctg atg tag atgagctctg acattggaag        542
Lys Asp Arg Gly Leu Asn Leu Leu Met
        145                 150 attctggagt ctgacaagtc acagcaggtt gagggtaggg agaaactgca ggtgagggt    602
gcatgctgaa gtcctgattt ctccaggtcc ccaggatcgg ctgagagccc tggtggtgat    662
ccccatcatc ttcgggatcc tgtttgccat cctcttggtg ctggtcttta tcaaaaaggt    722
ggccaagaag ccaaccaata aggcccccca ccccaagcag gaaccccagg agatcaattt    782
tcccgacgat cttcctggct ccaacactgc tgctccagtg caggagactt acatggatg     842
ccaaccggtc acccaggagg atggcaaaga gagtcgcatc tcagtgcagg agagacagtg    902
aggctgcacc cacccaggag tgtggccacg tgggcaaaca ggcagttggc cagagagcct    962
ggtgctgctg ctgctgtggc gtgagggtga ggggctggca ctgactgggc atagctcccc   1022
gcttctgcct gcacccctgc agtttagaca ggagacctgg cactggatgc agaaacagtt   1082
caccttgaag aacctctcac ttcaccctgg agccatcca gtctcccaac ttgtattaaa    1142
gacagaggca gaagtttggt ggtggtggtg ttggggtatg gtttagtaat atccaccaga   1202
ccttccgatc cagcagtttg gtgcccagag aggcatcatg gtggcttccc tgcgcccagg   1262
aagccatata cacagatgcc cattgcagca ttgtttgtga tagtgaacaa ctggaagctg   1322
cttaactgtc catcagcagg agactggcta aataaaatta gaatatattt atacaacaga   1382
atctcaaaaa cactgttgag taaggaaaaa aaggcatgct gctgaatgat gggtatggaa   1442
ctttttaaaa aagtacatgc ttttatgtat gtatattgcc tatggatata tgtataaata   1502
caatatgcat catatattga taaaaaaaaa aaaaaaaaaa aaaaaaaaaa aaaaaaaaaa   1562
aaaaaaaa                                                            1570

<210> SEQ ID NO 4
<211> LENGTH: 151
<212> TYPE: PRT
<213> ORGANISM: Homo sapiens

<400> SEQUENCE: 4

Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
```

```
                 35                  40                  45
Ser Asp Cys Thr Glu Phe Thr Glu Thr Glu Cys Leu Pro Cys Gly Glu
 50                  55                  60

Ser Glu Phe Leu Asp Thr Trp Asn Arg Glu Thr His Phe His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
                115                 120                 125

Phe Gly Val Lys Gln Ile Asp Ile Cys Gln Pro His Phe Pro Lys Asp
130                 135                 140

Arg Gly Leu Asn Leu Leu Met
145                 150

<210> SEQ ID NO 5
<211> LENGTH: 1193
<212> TYPE: DNA
<213> ORGANISM: Homo sapiens
<220> FEATURE:
<221> NAME/KEY: CDS
<222> LOCATION: (109)..(609)

<400> SEQUENCE: 5
tgaagatcag ctattagaag agaaagatca gttaagtcct ttggacctga tcagcttgat      60
acaagaacta ctgatttcaa cttctttggc ttaattctct cggaaacg atg aaa tat     117
                                                    Met Lys Tyr
                                                      1 aca agt tat atc ttg gct ttt cag ctc tgc atc gtt ttg ggt tct ctt     165
Thr Ser Tyr Ile Leu Ala Phe Gln Leu Cys Ile Val Leu Gly Ser Leu
  5                  10                  15 ggc tgt tac tgc cag gac cca tat gta aaa gaa gca gaa aac ctt aag     213
Gly Cys Tyr Cys Gln Asp Pro Tyr Val Lys Glu Ala Glu Asn Leu Lys
 20                  25                  30                  35 aaa tat ttt aat gca ggt cat tca gat gta gcg gat aat gga act ctt     261
Lys Tyr Phe Asn Ala Gly His Ser Asp Val Ala Asp Asn Gly Thr Leu
                 40                  45                  50 ttc tta ggc att ttg aag aat tgg aaa gag gag agt gac aga aaa ata     309
Phe Leu Gly Ile Leu Lys Asn Trp Lys Glu Glu Ser Asp Arg Lys Ile
             55                  60                  65 atg cag agc caa att gtc tcc ttt tac ttc aaa ctt ttt aaa aac ttt     357
Met Gln Ser Gln Ile Val Ser Phe Tyr Phe Lys Leu Phe Lys Asn Phe
         70                  75                  80 aaa gat gac cag agc atc caa aag agt gtg gag acc atc aag gaa gac     405
Lys Asp Asp Gln Ser Ile Gln Lys Ser Val Glu Thr Ile Lys Glu Asp
 85                  90                  95 atg aat gtc aag ttt ttc aat agc aac aaa aag aaa cga gat gac ttc     453
Met Asn Val Lys Phe Phe Asn Ser Asn Lys Lys Lys Arg Asp Asp Phe
100                 105                 110                 115 gaa aag ctg act aat tat tcg gta act gac ttg aat gtc caa cgc aaa     501
Glu Lys Leu Thr Asn Tyr Ser Val Thr Asp Leu Asn Val Gln Arg Lys
                120                 125                 130 gca ata cat gaa ctc atc caa gtg atg gct gaa ctg tcg cca gca gct     549
Ala Ile His Glu Leu Ile Gln Val Met Ala Glu Leu Ser Pro Ala Ala
            135                 140                 145 aaa aca ggg aag cga aaa agg agt cag atg ctg ttt caa ggt cga aga     597
Lys Thr Gly Lys Arg Lys Arg Ser Gln Met Leu Phe Gln Gly Arg Arg
        150                 155                 160
```

```
gca tcc cag taa tggttgtcct gcctgcaata tttgaattt aaatctaaat         649
Ala Ser Gln
    165 ctatttatta atatttaaca ttatttatat ggggaatata ttttagact catcaatcaa   709 ataagtattt ataatagcaa cttttgtgta atgaaaatga atatctatta atatatgtat  769 tatttataat tcctatatcc tgtgactgtc tcacttaatc ctttgttttc tgactaatta  829 ggcaaggcta tgtgattaca aggctttatc tcagggcca actaggcagc caacctaagc   889 aagatcccat gggttgtgtg tttatttcac ttgatgatac aatgaacact tataagtgaa  949 gtgatactat ccagttactg ccggtttgaa aatatgcctg caatctgagc cagtgcttta  1009 atggcatgtc agacagaact tgaatgtgtc aggtgaccct gatgaaaaca tagcatctca  1069 ggagatttca tgcctggtgc ttccaaatat tgttgacaac tgtgactgta cccaaatgga  1129 aagtaactca tttgttaaaa ttatcaatat ctaatatata tgaataaagt gtaagttcac  1189 aact                                                                1193
```

```
<210> SEQ ID NO 6
<211> LENGTH: 166
<212> TYPE: PRT
<213> ORGANISM: Homo sapiens

<400> SEQUENCE: 6

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Gln
145                 150                 155                 160

Gly Arg Arg Ala Ser Gln
                165
```

```
<210> SEQ ID NO 7
<211> LENGTH: 1669
<212> TYPE: DNA
<213> ORGANISM: Homo sapiens
<220> FEATURE:
<221> NAME/KEY: CDS
<222> LOCATION: (170)..(871)

<400> SEQUENCE: 7
ctccctcagc aaggacagca gaggaccagc taagagggag agaagcaact acagaccccc   60
```

```
cctgaaaaca accctcagac gccacatccc ctgacaagct gccaggcagg ttctcttcct      120
ctcacatact gacccacggc tccaccctct ctccctgga aaggacacc atg agc act       178
                                                     Met Ser Thr
                                                       1 gaa agc atg atc cgg gac gtg gag ctg gcc gag gag gcg ctc ccc aag        226
Glu Ser Met Ile Arg Asp Val Glu Leu Ala Glu Glu Ala Leu Pro Lys
  5              10                  15 aag aca ggg ggg ccc cag ggc tcc agg cgg tgc ttg ttc ctc agc ctc        274
Lys Thr Gly Gly Pro Gln Gly Ser Arg Arg Cys Leu Phe Leu Ser Leu
 20              25                  30                  35 ttc tcc ttc ctg atc gtg gca ggc gcc acc acg ctc ttc tgc ctg ctg        322
Phe Ser Phe Leu Ile Val Ala Gly Ala Thr Thr Leu Phe Cys Leu Leu
                 40                  45                  50 cac ttt gga gtg atc ggc ccc cag agg gaa gag ttc ccc agg gac ctc        370
His Phe Gly Val Ile Gly Pro Gln Arg Glu Glu Phe Pro Arg Asp Leu
             55                  60                  65 tct cta atc agc cct ctg gcc cag gca gtc aga tca tct tct cga acc        418
Ser Leu Ile Ser Pro Leu Ala Gln Ala Val Arg Ser Ser Ser Arg Thr
         70                  75                  80 ccg agt gac aag cct gta gcc cat gtt gta gca aac cct caa gct gag        466
Pro Ser Asp Lys Pro Val Ala His Val Val Ala Asn Pro Gln Ala Glu
     85                  90                  95 ggg cag ctc cag tgg ctg aac cgc cgg gcc aat gcc ctc ctg gcc aat        514
Gly Gln Leu Gln Trp Leu Asn Arg Arg Ala Asn Ala Leu Leu Ala Asn
100                 105                 110                 115 ggc gtg gag ctg aga gat aac cag ctg gtg gtg cca tca gag ggc ctg        562
Gly Val Glu Leu Arg Asp Asn Gln Leu Val Val Pro Ser Glu Gly Leu
                    120                 125                 130 tac ctc atc tac tcc cag gtc ctc ttc aag ggc caa ggc tgc ccc tcc        610
Tyr Leu Ile Tyr Ser Gln Val Leu Phe Lys Gly Gln Gly Cys Pro Ser
                135                 140                 145 acc cat gtg ctc ctc acc cac acc atc agc cgc atc gcc gtc tcc tac        658
Thr His Val Leu Leu Thr His Thr Ile Ser Arg Ile Ala Val Ser Tyr
            150                 155                 160 cag acc aag gtc aac ctc ctc tct gcc atc aag agc ccc tgc cag agg        706
Gln Thr Lys Val Asn Leu Leu Ser Ala Ile Lys Ser Pro Cys Gln Arg
165                 170                 175 gag acc cca gag ggg gct gag gcc aag ccc tgg tat gag ccc atc tat        754
Glu Thr Pro Glu Gly Ala Glu Ala Lys Pro Trp Tyr Glu Pro Ile Tyr
180                 185                 190                 195 ctg gga ggg gtc ttc cag ctg gag aag ggt gac cga ctc agc gct gag        802
Leu Gly Gly Val Phe Gln Leu Glu Lys Gly Asp Arg Leu Ser Ala Glu
                    200                 205                 210 atc aat cgg ccc gac tat ctc gac ttt gcc gag tct ggg cag gtc tac        850
Ile Asn Arg Pro Asp Tyr Leu Asp Phe Ala Glu Ser Gly Gln Val Tyr
                215                 220                 225 ttt ggg atc att gcc ctg tga ggaggacgaa catccaacct tcccaaacgc          901
Phe Gly Ile Ile Ala Leu
            230 ctcccctgcc ccaatcccttt tattaccccc tccttcagac accctcaacc tcttctggct    961 caaaaagaga attgggggct tagggtcgga acccaagctt agaactttaa gcaacaagac    1021 caccacttcg aaacctggga ttcaggaatg tgtggcctgc acagtgaagt gctggcaacc    1081 actaagaatt caaactgggg cctccagaac tcactggggc ctacagcttt gatccctgac    1141 atctggaatc tggagaccag ggagcctttg gttctggcca gaatgctgca ggacttgaga    1201 agacctcacc tagaaattga cacaagtgga ccttaggcct tcctctctcc agatgtttcc    1261 agacttcctt gagacacgga gcccagccct ccccatggag ccagctccct ctatttatgt    1321
```
ttgcacttgt gattatttat tatttattta ttatttattt atttacagat gaatgtattt    1381
atttgggaga ccggggtatc ctgggggacc caatgtagga gctgccttgg ctcagacatg    1441
ttttccgtga aaacggagct gaacaatagg ctgttcccat gtagccccct ggcctctgtg    1501
ccttcttttg attatgtttt ttaaaatatt tatctgatta agttgtctaa acaatgctga    1561
tttggtgacc aactgtcact cattgctgag cctctgctcc ccaggggagt tgtgtctgta    1621
atcgccctac tattcagtgg cgagaaataa agtttgctta gaaaagaa                 1669

<210> SEQ ID NO 8
<211> LENGTH: 233
<212> TYPE: PRT
<213> ORGANISM: Homo sapiens

<400> SEQUENCE: 8

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 9
<211> LENGTH: 1250
<212> TYPE: DNA
<213> ORGANISM: Mus musculus
<220> FEATURE:
<221> NAME/KEY: CDS
<222> LOCATION: (13)..(795)

<400> SEQUENCE: 9
ctttcagtca gc atg ata gaa aca tac agc caa cct tcc ccc aga tcc gtg    51
           Met Ile Glu Thr Tyr Ser Gln Pro Ser Pro Arg Ser Val
             1               5                  10

|     | 1 |     |     |     | 5 |     |     |     | 10 |     |     |     |     |     |
|-----|---|-----|-----|-----|---|-----|-----|-----|----|-----|-----|-----|-----|-----|
| gca | act | gga | ctt | cca | gcg | agc | atg | aag | att | ttt | atg | tat | tta | ctt | act | 99 |
| Ala | Thr | Gly | Leu | Pro | Ala | Ser | Met | Lys | Ile | Phe | Met | Tyr | Leu | Leu | Thr |
| 15  |     |     |     | 20  |     |     |     |     | 25  |     |     |     |     |     |

```
gca act gga ctt cca gcg agc atg aag att ttt atg tat tta ctt act       99
Ala Thr Gly Leu Pro Ala Ser Met Lys Ile Phe Met Tyr Leu Leu Thr
 15              20                  25 gtt ttc ctt atc acc caa atg att gga tct gtg ctt ttt gct gtg tat      147
Val Phe Leu Ile Thr Gln Met Ile Gly Ser Val Leu Phe Ala Val Tyr
 30              35                  40                  45 ctt cat aga aga ttg gat aag gtc gaa gag gaa gta aac ctt cat gaa      195
Leu His Arg Arg Leu Asp Lys Val Glu Glu Glu Val Asn Leu His Glu
                 50                  55                  60 gat ttt gta ttc ata aaa aag cta aag aga tgc aac aaa gga gaa gga      243
Asp Phe Val Phe Ile Lys Lys Leu Lys Arg Cys Asn Lys Gly Glu Gly
             65                  70                  75 tct tta tcc ttg ctg aac tgt gag gag atg aga agg caa ttt gaa gac      291
Ser Leu Ser Leu Leu Asn Cys Glu Glu Met Arg Arg Gln Phe Glu Asp
         80                  85                  90 ctt gtc aag gat ata acg tta aac aaa gaa gag aaa aaa gaa aac agc      339
Leu Val Lys Asp Ile Thr Leu Asn Lys Glu Glu Lys Lys Glu Asn Ser
     95                 100                 105 ttt gaa atg caa aga ggt gat gag gat cct caa att gca gca cac gtt      387
Phe Glu Met Gln Arg Gly Asp Glu Asp Pro Gln Ile Ala Ala His Val
110                 115                 120                 125 gta agc gaa gcc aac agt aat gca gca tcc gtt cta cag tgg gcc aag      435
Val Ser Glu Ala Asn Ser Asn Ala Ala Ser Val Leu Gln Trp Ala Lys
                130                 135                 140 aaa gga tat tat acc atg aaa agc aac ttg gta atg ctt gaa aat ggg      483
Lys Gly Tyr Tyr Thr Met Lys Ser Asn Leu Val Met Leu Glu Asn Gly
            145                 150                 155 aaa cag ctg acg gtt aaa aga gaa gga ctc tat tat gtc tac act caa      531
Lys Gln Leu Thr Val Lys Arg Glu Gly Leu Tyr Tyr Val Tyr Thr Gln
        160                 165                 170 gtc acc ttc tgc tct aat cgg gag cct tcg agt caa cgc cca ttc atc      579
Val Thr Phe Cys Ser Asn Arg Glu Pro Ser Ser Gln Arg Pro Phe Ile
    175                 180                 185 gtc ggc ctc tgg ctg aag ccc agc agt gga tct gag aga atc tta ctc      627
Val Gly Leu Trp Leu Lys Pro Ser Ser Gly Ser Glu Arg Ile Leu Leu
190                 195                 200                 205 aag gcg gca aat acc cac agt tcc tcc cag ctt tgc gag cag cag tct      675
Lys Ala Ala Asn Thr His Ser Ser Ser Gln Leu Cys Glu Gln Gln Ser
                210                 215                 220 gtt cac ttg ggc gga gtg ttt gaa tta caa gct ggt gct tct gtg ttt      723
Val His Leu Gly Gly Val Phe Glu Leu Gln Ala Gly Ala Ser Val Phe
            225                 230                 235 gtc aac gtg act gaa gca agc caa gtg atc cac aga gtt ggc ttc tca      771
Val Asn Val Thr Glu Ala Ser Gln Val Ile His Arg Val Gly Phe Ser
        240                 245                 250 tct ttt ggc tta ctc aaa ctc tga acagtgcgct gtcctaggct gcagcagggc    825
Ser Phe Gly Leu Leu Lys Leu
    255                 260 tgatgctggc agtcttccct atacagcaag tcagttagga cctgccctgt gttgaactgc    885
ctatttataa ccctaggatc tcctcatgg agaactattt attatgtacc cccaaggcac     945
atagagctgg aataagagaa ttacagggca ggcaaaaatc ccaagggacc ctgctcccta   1005
agaacttaca atctgaaaca gcaaccccac tgattcagac aaccagaaaa gacaaagcca   1065
taatacacag atgacagagc tctgatgaaa caacagataa ctaatgagca cagttttgtt   1125
gttttatggg tgtgtcgttc aatggacagt gtacttgact taccagggaa gatgcagaag   1185
ggcaactgtg agcctcagct cacaatctgt tatggttgac ctgggctccc tgcggcccta   1245
``` gtagg                                                              1250

<210> SEQ ID NO 10
<211> LENGTH: 260
<212> TYPE: PRT
<213> ORGANISM: Mus musculus

<400> SEQUENCE: 10

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
        260

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
gcatgatcga aacatacaac c                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
ctattatgaa gactcccagc g                                          21

<210> SEQ ID NO 13
<211> LENGTH: 915
<212> TYPE: DNA
<213> ORGANISM: Artificial Sequence
<220> FEATURE:
<223> OTHER INFORMATION: Optimized human CD40L

<400> SEQUENCE: 13
gggcgaattg ggccctctag atctgcagaa ttcggcttgc atgatcgaaa catacaacca    60
aacttctccc cgatctgcgg ccactggact gcccatcagc atgaaaattt ttatgtattt   120
acttactgtt tttcttatca cccagatgat tgggtcagca cttttgctg tgtatcttca    180 tagaaggttg gacaagatag aagatgaaag gaatcttcat gaagattttg tattcatgaa   240
aacgatacag agatgcaaca caggagaaag atccttatcc ttactgaact gtgaggagat   300
taaaagccag tttgaaggct tgtgtaagga tataatgtta aacaaagagg agacgaagaa   360
agaaaacagc tttgaaatgc aaaaaggtga tcagaatcct caaattgcgg cacatgtcat   420
aagtgaggcc agcagtaaaa caacatctgt gttacagtgg gctgaaaaag gatactacac   480
catgagcaac aacttggtaa ccctggaaaa tgggaaacag ctgaccgtta aaagacaagg   540
actctattat atctatgccc aagtcacctt ctgttccaat cgggaagctt cgagtcaagc   600
tccatttata gccagcctct gcctaaagtc ccccggtaga ttcgagagaa tcttactcag   660
agctgcaaat acccacagtt ccgccaaacc ttgcgggcaa caatccattc acttgggagg   720
agtatttgaa ttgcaaccag gtgcttcggt gtttgtcaat gtgactgatc caagccaagt   780
gagccatggc actggcttca cgtcctttgg cttactcaaa ctctgaacag tgtcaccttg   840
caggctgtgg tggagctgac gctgggagtc ttcataatac aagccgaatt ccagcacact   900
ggcggccgtt actag                                                   915

<210> SEQ ID NO 14
<211> LENGTH: 251
<212> TYPE: DNA
<213> ORGANISM: Artificial Sequence
<220> FEATURE:
<223> OTHER INFORMATION: CD40 Receptor 3'UTR

<400> SEQUENCE: 14
ggctgcaccc acccaggagt gtggccacgt gggcaaacag gcagttggcc agagagcctg    60
gtgctgctgc tgctgtggcg tgagggtgag gggctggcac tgactgggca tagctccccg   120
cttctgcctg caccccctgca gtttgagaca ggagacctgg cactggatgc agaaacagtt   180
caccttgaag aacctctcac ttcaccctgg agcccatcca gtctcccaac ttgtattaaa   240
gacagaggca g                                                        251

<210> SEQ ID NO 15
<211> LENGTH: 597
<212> TYPE: DNA
<213> ORGANISM: Homo sapiens

<400> SEQUENCE: 15
gcggactatg acttagttgc gttacaccct ttcttgacaa aacctaactt gcgcagaaaa    60

-continued

```
caagatgaga ttggcatggc tttatttgtt ttttttgttt tgttttggtt tttttttttt    120
ttttggcttg actcaggatt taaaaactgg aacggtgaag gtgacagcag tcggttggag    180
cgagcatccc ccaaagttca caatgtggcc gaggactttg attgcacatt gttgtttttt    240
taatagtcat tccaaatatg agatgcgttg ttacaggaag tcccttgcca tcctaaaagc    300
caccccactt ctctctaagg agaatggccc agtcctctcc caagtccaca caggggaggt    360
gatagcattg ctttcgtgta aattatgtaa tgcaaaattt ttttaatctt cgccttaata    420 ctttttttatt ttgttttatt ttgaatgatg agccttcgtg cccccccttc ccccttttttt    480 gtcccccaac ttgagatgta tgaaggcttt tggtctccct gggagtgggt ggaggcagcc    540
agggcttacc tgtacactga cttgagacca gttgaataaa agtgcacacc ttaaaaa       597
```

```
<210> SEQ ID NO 16
<211> LENGTH: 381
<212> TYPE: DNA
<213> ORGANISM: Homo sapiens

<400> SEQUENCE: 16
tttgattgca cattgttgtt tttttaatag tcattccaaa tatgagatgc gttgttacag     60
gaagtccctt gccatcctaa aagccacccc acttctctct aaggagaatg gcccagtcct    120
ctcccaagtc cacacagggg aggtgatagc attgctttcg tgtaaattat gtaatgcaaa    180 attttttttaa tcttcgcctt aatacttttt tattttgttt tattttgaat gatgagcctt    240
cgtgcccccc cttccccctt ttttgtcccc caacttgaga tgtatgaagg cttttggtct    300
ccctgggagt gggtggaggc agccagggct tacctgtaca ctgacttgag accagttgaa    360
taaaagtgca caccttaaaa a                                               381

<210> SEQ ID NO 17
<211> LENGTH: 139
<212> TYPE: DNA
<213> ORGANISM: Simian rotavirus

<400> SEQUENCE: 17
gaccaagcta acaacttggt atccaacttt ggtgagtatg tagctatatc aagctgtttg     60
aactctgtaa gtaaggatgc gtatacgcat tcgctacact gagttaatca ctctgatggt    120
atagtgagag gatgtgacc                                                 139

<210> SEQ ID NO 18
<211> LENGTH: 65
<212> TYPE: DNA
<213> ORGANISM: Simian rotavirus

<400> SEQUENCE: 18
gaccaagcta acaacttggt atccaacttt ggtgagtatg tagctatatc aagctgtttg     60
aactc                                                                 65

<210> SEQ ID NO 19
<211> LENGTH: 179
<212> TYPE: DNA
<213> ORGANISM: Homo sapiens

<400> SEQUENCE: 19 taccttttc gagagtgact cccgttgtcc caaggcttcc cagagcgaac ctgtgcggct     60
gcaggcaccg gcgcgtcgag tttccggcgt ccggaaggac cgagctcttc tcgcggatcc    120
agtgttccgt ttccagcccc caatctcaga gcggagccga cagagagcag ggaaccggc     179
```

<210> SEQ ID NO 20
<211> LENGTH: 1014
<212> TYPE: DNA
<213> ORGANISM: Mus musculus

<400> SEQUENCE: 20

| | | | | | | |
|---|---|---|---|---|---|---|
| agcgcagagg | cttggggcag | ccgagctgca | gcgagcgcgc | ggcactgggg | gcgagctgag | 60 |
| cggcggcagc | ggagctctgt | cgcgagacgc | agcgacaagg | cagactatca | gcggactcac | 120 |
| cagcccggga | gtctgtgctc | tgggatttga | tattcaaacc | tcttaatttt | tttttcttaa | 180 |
| actgtattgt | tttacgcttt | aatttatttt | tgcttcctat | tccctctta | aatcgtgcca | 240 |
| acggtttgag | gaggttggtt | cttcactccc | tcaaatcact | tcggattgtg | gaaatcagca | 300 |
| gacgaaagag | gtatcaagag | ctccagagag | aagtcaagga | agagagagag | agaccggtca | 360 |
| gagagagcgc | gctggcgagc | gaacagagag | agggacaggg | gcaaagttga | cttgaccttg | 420 |
| cttttggggg | tgaccgccag | agcgcggcgt | gacctccccc | ttcgatcttg | catcggacca | 480 |
| gtcgcgctga | cggacagaca | gacagacacc | gcccccagcc | ccagcgccca | cctcctcgcc | 540 |
| ggcgggctgc | cgacggtgga | cgcggcggcg | agccgagaaa | ccgaagcccg | cgcccggagg | 600 |
| cgggtggagg | gggtcgggc | tcgcgggatt | gcacggaaac | ttttcgtcca | acttctgggc | 660 |
| tcttctcgct | ccgtagtagc | cgtggtctgc | gccgcaggag | acaaaccgat | ccggagctgg | 720 |
| gagaaggcta | gctcggccct | ggagaggccg | gggcccgaga | agagagggga | ggaaggaaga | 780 |
| ggagaggggg | ccacagtggg | cgctcggctc | tcaggagccg | agctcatgga | cgggtgaggc | 840 |
| ggccgtgtgc | gcagacagtg | ctccagccgc | gcgcgcgccc | caggccccgg | cccgggcctc | 900 |
| ggttccagaa | gggagaggag | cccgccaagg | cgcgcaagag | agcgggctgc | ctcgcagtcc | 960 |
| ggagccggag | agagggagcg | cgagccgccg | cggccccgga | cggcctccga | aacc | 1014 |

<210> SEQ ID NO 21
<211> LENGTH: 163
<212> TYPE: DNA
<213> ORGANISM: Mus musculus

<400> SEQUENCE: 21

| | | | | | | |
|---|---|---|---|---|---|---|
| agcgcagagg | cttggggcag | ccgagcggca | gccaggcccc | ggcccgggcc | tcggttccag | 60 |
| aagggagagg | agcccgccaa | ggcgcgcaag | agagcgggct | gcctcgcagt | ccgagccgga | 120 |
| gagggagcgc | gagccgcgcc | ggccccggac | ggcctccgaa | acc | | 163 |

<210> SEQ ID NO 22
<211> LENGTH: 180
<212> TYPE: DNA
<213> ORGANISM: Spleen necrosis virus

<400> SEQUENCE: 22

| | | | | | | |
|---|---|---|---|---|---|---|
| ttgctcggcc | tcgaggtcgg | ggtcgccgtc | ctacacattg | ttgttgtgac | gtgcggccca | 60 |
| gattcgaatc | tgtaataaaa | cttttttttt | tctgaatcct | cagattggca | gtgagaggag | 120 |
| attttgttcg | tggtgttggc | tggcctactg | ggtgggcgca | gggatcttgg | tggcgtgaaa | 180 |

<210> SEQ ID NO 23
<211> LENGTH: 143
<212> TYPE: DNA
<213> ORGANISM: Tobacco etch virus

<400> SEQUENCE: 23

```
aaataacaaa tctcaacaca acatatacaa aacaaacgaa tctcaagcaa tcaagcattc        60
tacttctatt gcagcaattt aaatcatttc ttttaaagca aaagcaattt tctgaaaatt       120
ttcaccattt acgaacgata gca                                               143
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Leu Ala Gly Ile Gly Ile Leu Thr Val
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Ala Ala Gly Ile Gly Ile Leu Thr Val
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Phe Leu Thr Pro Lys Lys Leu Gln Cys Val
1               5                   10
```